United States Patent
Hoffman et al.

(10) Patent No.: US 12,421,241 B2
(45) Date of Patent: Sep. 23, 2025

(54) SUBSTITUTED PYRIDINES AS PARP1 INHIBITORS

(71) Applicant: XinThera, Inc., Foster City, CA (US)

(72) Inventors: Robert L. Hoffman, San Diego, CA (US); Porino Jinjo Va, San Diego, CA (US); Joseph Robert Pinchman, San Diego, CA (US); Qing Dong, San Diego, CA (US); Stephen W. Kaldor, San Diego, CA (US)

(73) Assignee: XinThera, Inc., Foster City, CA (US)

( * ) Notice: Subject to any disclaimer, the term of this patent is extended or adjusted under 35 U.S.C. 154(b) by 0 days.

(21) Appl. No.: 18/653,538

(22) Filed: May 2, 2024

(65) Prior Publication Data

US 2024/0400569 A1   Dec. 5, 2024

Related U.S. Application Data

(63) Continuation of application No. 18/471,250, filed on Sep. 20, 2023, now Pat. No. 12,006,322, which is a continuation of application No. 18/449,569, filed on Aug. 14, 2023, now abandoned, which is a continuation of application No. 18/140,370, filed on Apr. 27, 2023, now Pat. No. 11,795,173.

(60) Provisional application No. 63/336,078, filed on Apr. 28, 2022, provisional application No. 63/381,482, filed on Oct. 28, 2022.

(51) Int. Cl.
*A61K 31/4985* (2006.01)
*C07D 487/04* (2006.01)
*C07D 491/04* (2006.01)

(52) U.S. Cl.
CPC ......... *C07D 487/04* (2013.01); *C07D 491/04* (2013.01)

(58) Field of Classification Search
CPC .................. A61K 31/4985; C07D 487/04
USPC .......................................... 514/354; 544/346
See application file for complete search history.

(56) References Cited

U.S. PATENT DOCUMENTS

| | | | |
|---|---|---|---|
| 8,404,713 B2 | 3/2013 | Angibaud et al. |
| 8,541,417 B2 | 9/2013 | Brown et al. |
| 10,464,919 B2 | 11/2019 | Lee et al. |
| 11,325,906 B2 | 5/2022 | Johannes et al. |
| 11,591,331 B2 | 2/2023 | Trzoss et al. |
| 11,795,173 B1 | 10/2023 | Hoffman et al. |
| 11,802,128 B2 | 10/2023 | Hoffman et al. |
| 11,939,329 B2 | 3/2024 | Hoffman et al. |
| 12,006,322 B2 | 6/2024 | Hoffman et al. |
| 2021/0009577 A1 | 1/2021 | Lanman et al. |
| 2021/0040084 A1 | 2/2021 | Johannes et al. |
| 2022/0015338 A1 | 1/2022 | Zhang et al. |
| 2022/0348574 A1 | 11/2022 | Trzoss et al. |
| 2023/0128041 A1 | 4/2023 | Trzoss et al. |
| 2023/0159525 A1 | 5/2023 | Hoffman et al. |
| 2023/0203033 A1 | 6/2023 | Hoffman et al. |
| 2023/0234952 A1 | 7/2023 | Hoffman et al. |
| 2023/0348473 A1 | 11/2023 | Hoffman et al. |
| 2024/0109904 A1 | 4/2024 | Hoffman et al. |
| 2024/0174669 A1 | 5/2024 | Reddy et al. |
| 2024/0317746 A1 | 9/2024 | Liu et al. |
| 2024/0368162 A1 | 11/2024 | Dong et al. |

FOREIGN PATENT DOCUMENTS

| | | |
|---|---|---|
| AU | 2016276806 B2 | 2/2019 |
| CN | 104370898 A | 2/2015 |
| CN | 115232129 A | 10/2022 |
| CN | 115403595 A | 11/2022 |
| CN | 116143776 A | 5/2023 |
| CN | 116535401 A | 8/2023 |
| CN | 116987066 A | 11/2023 |
| CN | 117017962 A | 11/2023 |
| CN | 117447449 A | 1/2024 |
| CN | 118084916 A | 5/2024 |
| JP | 2011-500758 | 1/2011 |
| JP | 2018-523679 | 8/2018 |
| JP | 2022-541483 | 9/2022 |
| JP | 2023-506368 | 2/2023 |
| WO | WO 2003/080581 A1 | 10/2003 |
| WO | WO 2009/053373 A1 | 4/2009 |
| WO | WO 2009/076512 A1 | 6/2009 |
| WO | WO 2010/085570 A1 | 7/2010 |
| WO | WO 2011/014681 A1 | 2/2011 |
| WO | 2011035019 A1 | 3/2011 |
| WO | WO 2014/064149 A1 | 5/2014 |
| WO | WO 2015/134973 A1 | 9/2015 |
| WO | WO 2016/107603 A1 | 7/2016 |
| WO | WO 2016/200101 A2 | 12/2016 |
| WO | WO 2020/098630 A1 | 5/2020 |
| WO | WO 2021/013735 A1 | 1/2021 |
| WO | WO 2021/260092 A1 | 12/2021 |
| WO | WO 2022/222921 A1 | 10/2022 |
| WO | WO 2022/222964 A1 | 10/2022 |
| WO | WO 2022/222965 A1 | 10/2022 |
| WO | WO 2022/222966 A1 | 10/2022 |

(Continued)

OTHER PUBLICATIONS

Boehler et al. Poly(ADP-ribose) polymerase 3 (PARP3), a newcomer in cellular response to DNA damage and mitotic progression. PNAS USA 108(7):2783-2788 (2011).

(Continued)

*Primary Examiner* — Douglas M Willis

(74) *Attorney, Agent, or Firm* — Sheppard Mullin Richter & Hampton LLP

(57) ABSTRACT

Described herein are tricyclic PARP1 inhibitors and pharmaceutical compositions comprising said inhibitors. The subject compounds and compositions are useful for the treatment of cancer.

4 Claims, No Drawings

(56) References Cited

FOREIGN PATENT DOCUMENTS

| | | |
|---|---|---|
| WO | WO 2022/222995 A1 | 10/2022 |
| WO | WO 2022/223025 A1 | 10/2022 |
| WO | WO 2022/225934 A1 | 10/2022 |
| WO | WO 2022/228387 A1 | 11/2022 |
| WO | WO 2022/247816 A1 | 12/2022 |
| WO | WO 2022/261777 A1 | 12/2022 |
| WO | WO 2023/025307 A1 | 3/2023 |
| WO | WO 2023/036285 A1 | 3/2023 |
| WO | WO 2023/046034 A1 | 3/2023 |
| WO | WO 2023/046149 A1 | 3/2023 |
| WO | WO 2023/046158 A1 | 3/2023 |
| WO | WO 2023/051716 A1 | 4/2023 |
| WO | WO 2023/051807 A1 | 4/2023 |
| WO | WO 2023/051812 A1 | 4/2023 |
| WO | WO 2023/056039 A1 | 4/2023 |
| WO | WO 2023/061406 A1 | 4/2023 |
| WO | WO 2023/088408 A1 | 5/2023 |
| WO | WO 2023/109521 A1 | 6/2023 |
| WO | 2023134647 A1 | 7/2023 |
| WO | WO 2023/133413 A1 | 7/2023 |
| WO | WO 2023/138541 A1 | 7/2023 |
| WO | WO 2023/143236 A1 | 8/2023 |
| WO | WO 2023/144450 A1 | 8/2023 |
| WO | WO 2023/146294 A1 | 8/2023 |
| WO | WO 2023/146957 A1 | 8/2023 |
| WO | WO 2023/146960 A1 | 8/2023 |
| WO | WO 2023/147009 A1 | 8/2023 |
| WO | WO 2023/156386 A1 | 8/2023 |
| WO | WO 2023/169226 A1 | 9/2023 |
| WO | WO 2023/207283 A1 | 11/2023 |
| WO | WO 2023/207284 A1 | 11/2023 |
| WO | WO 2023/217045 A1 | 11/2023 |
| WO | WO 2023/227052 A1 | 11/2023 |
| WO | WO 2023/232069 A1 | 12/2023 |
| WO | WO 2024/041643 A1 | 2/2024 |
| WO | WO 2024/046366 A1 | 3/2024 |
| WO | WO 2024/046420 A1 | 3/2024 |
| WO | WO 2024/050370 A1 | 3/2024 |
| WO | 2024077137 A1 | 4/2024 |
| WO | WO2024/067691 A1 | 4/2024 |
| WO | WO2024/067694 A1 | 4/2024 |
| WO | WO2024/082654 A1 | 4/2024 |
| WO | WO2024/083201 A1 | 4/2024 |
| WO | WO2024/083211 A1 | 4/2024 |
| WO | WO2024/083218 A1 | 4/2024 |
| WO | WO2024/099364 A2 | 5/2024 |
| WO | WO2024/099416 A1 | 5/2024 |
| WO | WO2024/109871 A1 | 5/2024 |
| WO | 2024206172 A1 | 10/2024 |

OTHER PUBLICATIONS

Gill et al. The novel PARP1-selective inhibitor AZD5305 has reduced haematological toxicity when compared to PARP1/2 inhibitors in pre-clinical models. Poster# 1374 AACR 2021 Annual Apr. 10-19, 2020.

Gozgit et al. PARP7 negatively regulates the type I interferon response in cancer cells and its inhibition triggers antitumor immunity. Cancer Cell 39(9):1214-1226 (2021).

Hande et al. Structure-based and property-based drug design of AZD5305, a highly selective PARP1 inhibitor and trapper. Poster #296 AACR 2021. Apr. 10-15, 2021.

Illuzzi et al. In vitro cellular profiling of AZD5305, novel PARP1-selective inhibitor and trapper. Poster #1272 AACR2021, Apr. 10-15, 2021.

Johannes et al., "Discovery of 5-{4-[(7-Ethyl-6-oxo-5,6-dihydro-1,5-naphthyridin-3-yl)methyl]piperazin-1-yl}-N-methylpyridine-2-carboxamide (AZD5305): a PARP1-DNA Trapper with High Selectivity for PARP1 over PARP2 and Other PARPs," Journal of Medicinal Chemistry, 2021, vol. 64, pp. 14498-14512.

Johannes et al. Discovery and first structural disclosure of AZD5305, a next generation, highly selective PARP1 inhibitor and trapper. AstraZeneca—AZD5305—a best in class highly selective PARP1 inhibitor. Presentation at AACR 2021 Apr. 10, 2021.

Krug et al., "Inhibition of host PARP1 contributes to the anti-inflammatory and antitubercular activity of pyrazinamide," Nature Communications, Dec. 2023, 15 pages.

Kulak et al. Disruption of Wnt/β-Catenin Signaling and Telomeric Shortening Are Inextricable Consequences of Tankyrase Inhibition in Human Cells. Mol Cell Biol. 35(14):2425-2435 (2015).

PCT/US2022/025357 International Search Report and Written Opinion dated Jun. 30, 2022.

PCT/US2022/045415 International Search Report and Written Opinion dated Nov. 25, 2022.

PCT/US2023/011268 International Search Report and Written Opinion dated Apr. 4, 2023.

PCT/US2023/011609 International Search Report and Written Opinion dated Mar. 29, 2023.

PCT/US2023/011613 International Search Report and Written Opinion dated Apr. 11, 2023.

PCT/US2023/076075 International Search Report and Written Opinion dated Jan. 25, 2024.

PCT/US2024/021201 International Search Report and Written Opinion dated Jun. 26, 2024.

Ren et al. Synthesis and in vitro biological evaluation of 3-ethyl-1,5-naphthyridin-2 (1H)-one derivatives as potent PARP-1 selective inhibitors and PARP-1 DNA trappers. Bioorg Med Chem Lett. 129046 (2022).

Staniszewska et al. The novel PARP1-selective inhibitor, AZD5305, is efficacious as monotherapy and in combination with standard of care chemotherapy in in vivo preclinical models. Poster#1270 AACR 2021. Apr. 10-15, and May 17-21, 2021.

U.S. Appl. No. 17/957,584 Office Action dated Feb. 15, 2023.

U.S. Appl. No. 18/099,770 Office Action dated Apr. 26, 2023.

U.S. Appl. No. 18/115,314 Office Action dated May 30, 2023.

Vermehren-Schmaedick et al. Characterization of PARP6 Function in Knockout Mice and Patients with Developmental Delay. Cells 10(6):1289 (2021).

Vyas et al. A Systematic Analysis of the PARP Protein Family Identifies New Functions Critical for Cell Physiology. Nat. Commun. 4(1):2240 (2013).

Yu et al. PARP-10, a novel Myc-interacting protein with poly(ADP-ribose) polymerase activity, inhibits transformation. Oncogene 24:1982-1993 (2005).

Loryan et al., "Unbound Brain-to-Plasma Partition Coefficient, Kp,uu,brain—a Game Changing Parameter for CNS Drug Discovery and Development," Pharmaceutical Research, 2022, vol. 39, pp. 1321-1341.

Zefirova et al., "About the History and Development of the Concept of Bioisosterism," Bulletin of Moscow University. SER.2. Chemistry. 2002, vol. 43, No. 4, 14 pages with English translation.

SUBSTITUTED PYRIDINES AS PARP1 INHIBITORS

CROSS-REFERENCE

This application is a continuation of U.S. patent application Ser. No. 18/471,250 filed Sep. 20, 2023, now U.S. Pat. No. 12,006,322, which is a continuation of U.S. patent application Ser. No. 18/449,569, filed Aug. 14, 2023, now abandoned, which is a continuation of U.S. patent application Ser. No. 18/140,370, filed Apr. 27, 2023, now U.S. Pat. No. 11,795,173, which claims the benefit of U.S. Provisional Application Ser. No. 63/336,078 filed Apr. 28, 2022 and U.S. Provisional Application Ser. No. 63/381,482 filed Oct. 28, 2022 which are hereby incorporated by reference in their entirety.

BACKGROUND OF THE INVENTION

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytotoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut, and skeletal muscle. Inhibitors have been efficacious in inflammatory diseases such as arthritis, gout, inflammatory bowel disease, CNS inflammation such as MS and allergic encephalitis, sepsis, septic shock, hemorrhagic shock, pulmonary fibrosis, and uveitis. PARP inhibitors have also shown benefit in several models of degenerative disease including diabetes (as well as complications) and Parkinson's disease. PARP inhibitors can ameliorate the liver toxicity following acetaminophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

PARP1 and PARP2 are the most extensively studied PARPs for their role in DNA damage repair. PARP1 is activated by DNA damage breaks and functions to catalyze the addition of poly (ADP-ribose) (PAR) chains to target proteins. This post-translational modification, known as PARylation, mediates the recruitment of additional DNA repair factors to DNA lesions.

Following completion of this recruitment role, PARP auto-PARylation triggers the release of bound PARP from DNA to allow access to other DNA repair proteins to complete repair. Thus, the binding of PARP to damaged sites, its catalytic activity, and its eventual release from DNA are all important steps for a cancer cell to respond to DNA damage caused by chemotherapeutic agents and radiation therapy.

Inhibition of PARP family enzymes has been exploited as a strategy to selectively kill cancer cells by inactivating complementary DNA repair pathways. A number of pre-clinical and clinical studies have demonstrated that tumor cells bearing deleterious alterations of BRCA1 or BRCA2, key tumor suppressor proteins involved in double-strand DNA break (DSB) repair by homologous recombination (HR), are selectively sensitive to small molecule inhibitors of the PARP family of DNA repair enzymes. Such tumors have deficient homologous recombination repair (HRR) pathways and are dependent on PARP enzymes function for survival. Although PARP inhibitor therapy has predominantly targeted SRCA-mutated cancers, PARP inhibitors have been tested clinically in non-SRCA-mutant tumors, those which exhibit homologous recombination deficiency (HRD).

It is believed that PARP inhibitors having improved selectivity for PARP1 may possess improved efficacy and reduced toxicity compared to other clinical PARP1/2 inhibitors. It is believed also that selective strong inhibition of PARP1 would lead to trapping of PARP1 on DNA, resulting in DNA double strand breaks (DSBs) through collapse of replication forks in S-phase. It is believed also that PARP1-DNA trapping is an effective mechanism for selectively killing tumor cells having HRD. An unmet medical need therefore exists for effective and safe PARP inhibitors. Especially PARP inhibitors having selectivity for PARP1.

SUMMARY OF THE INVENTION

Disclosed herein is a compound of Formula (I), or a pharmaceutically acceptable salt, solvate, or stereoisomer thereof:

Disclosed herein is a compound of Formula (I), or a pharmaceutically acceptable salt, solvate, or stereoisomer thereof:

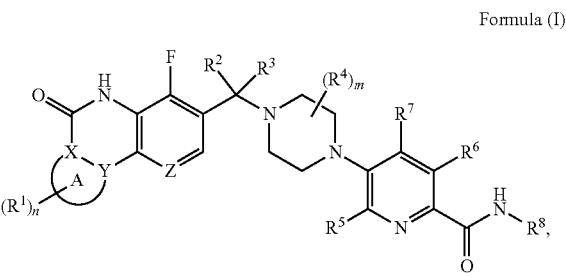

Formula (I)

wherein:
Ring A taken with X and Y is a 5-membered heterocycloalkyl or a 5-membered heteroaryl;
X is C, CH, or N;
Y is C, CH, or N;
each $R^1$ is independently deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;
or two $R^1$ on the same carbon are taken together to form an oxo;
n is 0-6;
Z is N or $CR^Z$;
$R^Z$ is hydrogen, deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;

$R^2$ is hydrogen, deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;

$R^3$ is hydrogen, deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;

or $R^2$ and $R^3$ are taken together to form a cycloalkyl or a heterocycloalkyl; each optionally substituted with one or more R;

each $R^4$ is independently deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, or $C_2$-$C_6$alkynyl;

or two $R^4$ on the same carbon are taken together to form an oxo;

or two $R^4$ on the same carbon or different carbons are taken together to form a cycloalkyl or heterocycloalkyl; each optionally substituted with one or more R;

m is 0-4;

$R^5$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^6$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^7$ is hydrogen, deuterium, halogen, —CN, —OH, —$OR^a$, —$NR^cR^d$, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^8$ is hydrogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

each $R^a$ is independently $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein each alkyl, alkenyl, alkynyl, cycloalkyl, and heterocycloalkyl is independently optionally substituted with one or more R;

each $R^c$ and $R^d$ are independently hydrogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein each alkyl, alkenyl, alkynyl, cycloalkyl, and heterocycloalkyl is independently optionally substituted with one or more R;

or $R^c$ and $R^d$ are taken together with the atom to which they are attached to form a heterocycloalkyl optionally substituted with one or more R; and each R is independently halogen, —CN, —OH, —$OC_1$-$C_3$alkyl, —$OC_1$-$C_3$haloalkyl, —$SC_1$-$C_3$alkyl, —S(=O)$C_1$-$C_3$alkyl, —S(=O)$_2C_1$-$C_3$alkyl, —S(=O)$_2NH_2$, —S(=O)$_2NHC_1$-$C_3$alkyl, —S(=O)$_2N(C_1$-$C_3$alkyl)$_2$, —$NH_2$, —NHC—$C_3$alkyl, —N($C_1$-$C_3$alkyl)$_2$, —C(=O)$C_1$-$C_3$alkyl, —C(=O)OH, —C(=O)$OC_1$-$C_3$alkyl, —C(=O)$NH_2$, —C(=O)NHC$_1$-$C_3$alkyl, —C(=O)N($C_1$-$C_3$alkyl)$_2$, $C_1$-$C_3$alkyl, $C_1$-$C_3$haloalkyl, $C_1$-$C_3$ deuteroalkyl, $C_1$-$C_3$ hydroxyalkyl, $C_1$-$C_3$ aminoalkyl, $C_1$-$C_3$ heteroalkyl, or $C_3$-$C_6$cycloalkyl;

or two R on the same atom are taken together to form an oxo.

Also disclosed herein is a pharmaceutical composition comprising a compound disclosed herein, or a pharmaceutically acceptable salt, solvate, or stereoisomer thereof, and a pharmaceutically acceptable excipient.

Also disclosed herein is a method of treating a cancer comprising a BRCA1 and/or a BRCA2 mutation in a subject in need thereof, the method comprising administering a compound disclosed herein, or a pharmaceutically acceptable salt, solvate, or stereoisomer thereof. Also disclosed herein is a method of treating a cancer comprising a mutation in a gene conferring homologous repair deficiency in a subject in need thereof, the method comprising administering a compound disclosed herein, or a pharmaceutically acceptable salt, solvate, or stereoisomer thereof. In some embodiments, the mutation in a gene conferring homologous repair deficiency comprises ATM, BRCA1, BRCA2, BARD1, BRIP1, CDK12, CHEK1, CHEK2, FANCL, PALB2, RAD51B, RAD51C, RAD51D, or RAD54L, or any combinations thereof. In some embodiments, the cancer is bladder cancer, brain & CNS cancer, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer. In some embodiments, the cancer is metastatic cancer. In some embodiments, the cancer has metastasized in the brain.

Also disclosed herein is a method of treating a cancer that is present in the brain in a subject in need thereof, the method comprising administering a compound disclosed herein, or a pharmaceutically acceptable salt, solvate, or stereoisomer thereof.

Also disclosed herein is a method of treating brain cancer in a subject in need thereof, the method comprising administering a compound disclosed herein, or a pharmaceutically acceptable salt, solvate, or stereoisomer thereof. In some embodiments, the compound or a pharmaceutically acceptable salt, solvate, or stereoisomer thereof, is brain penetrant.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "some embodiments" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.
"Carboxyl" refers to —COOH.
"Cyano" refers to —CN.
"Alkyl" refers to a straight-chain or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_{1-10}$alkyl. In some embodiments, the alkyl is a $C_{1-6}$alkyl. In some embodiments, the alkyl is a $C_{1-5}$alkyl. In some embodiments, the alkyl is a $C_{1-4}$alkyl. In some embodiments, the alkyl is a $C_{1-3}$alkyl. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to a straight-chain, or branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "$C_2$-$C_6$ alkenyl" or "$C_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkylene is optionally substituted with oxo, halogen, —CN, —COOH, COOMe, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a partially or fully saturated, monocyclic, or poly cyclic carbocyclic ring, which may include fused (when fused with an aryl or a heteroaryl ring, the cycloalkyl is bonded through a non-aromatic ring atom) or bridged ring systems. In some embodiments, the cycloalkyl is fully saturated. Representative cycloalkyls include, but are not limited to, cycloalkyls having from three to fifteen carbon atoms ($C_3$-$C_{15}$ cycloalkyl or $C_3$-$C_{15}$ cycloalkenyl), from three to ten carbon atoms ($C_3$-$C_{10}$ cycloalkyl or $C_3$-$C_{10}$ cycloalkenyl), from three to eight carbon atoms ($C_3$-$C_8$ cycloalkyl or $C_3$-$C_8$ cycloalkenyl), from three to six carbon atoms ($C_3$-$C_6$ cycloalkyl or $C_3$-$C_6$ cycloalkenyl), from three to five carbon atoms ($C_3$-$C_5$ cycloalkyl or $C_3$-$C_5$ cycloalkenyl), or three to four carbon atoms ($C_3$-$C_4$ cycloalkyl or $C_3$-$C_4$ cycloalkenyl). In some embodiments, the cycloalkyl is a 3- to 10-membered cycloalkyl or a 3- to 10-membered cycloalkenyl. In some embodiments, the cycloalkyl is a 3- to 6-membered cycloalkyl or a 3- to 6-membered cycloalkenyl. In some embodiments, the cycloalkyl is a 5- to 6-membered cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1] heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl include, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl include, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous and sulfur. In some embodiments, the heterocycloalkyl is fully saturated. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms ($C_2$-$C_{15}$ heterocycloalkyl or $C_2$-$C_{15}$ heterocycloalkenyl), from two to ten carbon atoms ($C_2$-$C_{10}$ heterocycloalkyl or $C_2$-$C_{10}$ heterocycloalkenyl), from two to eight carbon atoms ($C_2$-$C_8$ heterocycloalkyl or $C_2$-$C_8$ heterocycloalkenyl), from two to seven carbon atoms ($C_2$-$C_7$ heterocycloalkyl or $C_2$-$C_7$ heterocycloalkenyl), from two to six carbon atoms ($C_2$-$C_6$ heterocycloalkyl or $C_2$-$C_6$ heterocycloalkenyl), from two to five carbon atoms ($C_2$-$C_5$ heterocycloalkyl or $C_2$-$C_5$ heterocycloalkenyl), or two to four carbon atoms ($C_2$-$C_4$ heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with oxo, halogen, methyl, ethyl, —CN, —COOH, COOMe, —$CF_3$, —OH, —OMe, —$NH_2$, or —$NO_2$. In some embodiments, the heterocycloalkyl is optionally substituted with halogen, methyl, ethyl, —CN, —$CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, I-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF₃, —OH, —OMe, —NH₂, or —NO₂. In some embodiments, the heteroaryl is optionally substituted with halogen, methyl, ethyl, —CN, —CF₃, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH₂CH₃), fully substituted (e.g., —CF₂CF₃), mono-substituted (e.g., —CH₂CH₂F) or substituted at a level anywhere in-between fully substituted and mono-substituted (e.g., —CH₂CHF₂, —CH₂CF₃, —CF₂CH₃, —CFHCHF₂, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

The term "one or more" when referring to an optional substituent means that the subject group is optionally substituted with one, two, three, four, or more substituents. In some embodiments, the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition.

"Synergy" or "synergize" refers to an effect of a combination that is greater than additive of the effects of each component alone at the same doses.

As used herein, a "disease or disorder associated with PARP" or, alternatively, "a PARP-mediated disease or disorder" means any disease or other deleterious condition in which PARP, or a mutant thereof, is known or suspected to play a role.

As used herein, a "disease or disorder associated with PARP" or, alternatively, "a PARP1-mediated disease or disorder" means any disease or other deleterious condition in which PARP1, or a mutant thereof, is known or suspected to play a role.

Compounds

Described herein are compounds, or a pharmaceutically acceptable salt, solvate, or stereoisomer thereof useful in the treatment of cancer.

Disclosed herein is a compound of Formula (I), or a pharmaceutically acceptable salt, solvate, or stereoisomer thereof:

Formula (I)

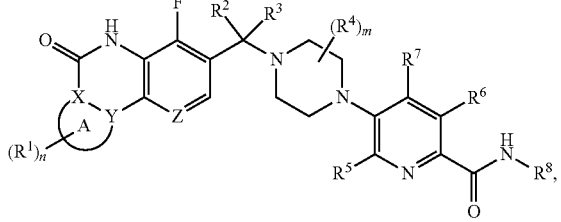

wherein:
Ring A taken with X and Y is a 5-membered heterocycloalkyl or a 5-membered heteroaryl;
X is C, CH, or N;
Y is C, CH, or N;
each R¹ is independently deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R; or two R¹ on the same carbon are taken together to form an oxo;
n is 0-6;
Z is N or $CR^Z$;
$R^Z$ is hydrogen, deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;
R² is hydrogen, deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;
R³ is hydrogen, deuterium, halogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R;
or R² and R³ are taken together to form a cycloalkyl or a heterocycloalkyl; each optionally substituted with one or more R;
each R⁴ is independently deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, or $C_2$-$C_6$alkynyl;
or two R⁴ on the same carbon are taken together to form an oxo;
or two R⁴ on the same carbon or different carbons are taken together to form a cycloalkyl or heterocycloalkyl; each optionally substituted with one or more R;
m is 0-4;
R⁵ is hydrogen, deuterium, halogen, —CN, —OH, —$OR^a$, —$NR^cR^d$, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^6$ is hydrogen, deuterium, halogen, —CN, —OH, —OR, —NR$^c$R$^d$, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^7$ is hydrogen, deuterium, halogen, —CN, —OH, —OR$^a$, —NR$^c$R$^d$, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

$R^8$ is hydrogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein the alkyl, alkenyl, alkynyl, cycloalkyl, and heterocycloalkyl is optionally substituted with one or more R;

each $R^a$ is independently $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein each alkyl, alkenyl, alkynyl, cycloalkyl, and heterocycloalkyl is independently optionally substituted with one or more R;

each $R^c$ and $R^d$ are independently hydrogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, $C_2$-$C_6$alkenyl, $C_2$-$C_6$alkynyl, cycloalkyl, or heterocycloalkyl; wherein each alkyl, alkenyl, alkynyl, cycloalkyl, and heterocycloalkyl is independently optionally substituted with one or more R;

or $R^c$ and $R^d$ are taken together with the atom to which they are attached to form a heterocycloalkyl optionally substituted with one or more R; and each R is independently halogen, —CN, —OH, —OC$_1$-C$_3$alkyl, —OC$_1$-C$_3$haloalkyl, —SC$_1$-C$_3$alkyl, —S(=O)C$_1$-C$_3$alkyl, —S(=O)$_2$C$_1$-C$_3$alkyl, —S(=O)$_2$NH$_2$, —S(=O)$_2$NHC$_1$-C$_3$alkyl, —S(=O)$_2$N(C$_1$-C$_3$alkyl)$_2$, —NH$_2$, —NHC$_1$-C$_3$alkyl, —N(C$_1$-C$_3$alkyl)$_2$, —C(=O)C$_1$-C$_3$alkyl, —C(=O)OH, —C(=O)OC$_1$-C$_3$alkyl, —C(=O)NH$_2$, —C(=O)NHC$_1$-C$_3$alkyl, —C(=O)N(C$_1$-C$_3$alkyl)$_2$, $C_1$-$C_3$alkyl, $C_1$-$C_3$haloalkyl, $C_1$-$C_3$ deuteroalkyl, $C_1$-$C_3$ hydroxyalkyl, $C_1$-$C_3$ aminoalkyl, $C_1$-$C_3$ heteroalkyl, or $C_3$-$C_6$cycloalkyl;

or two R on the same atom are taken together to form an oxo.

In some embodiments of a compound of Formula (I), Ring A taken with X and Y is a 5-membered heterocycloalkyl. In some embodiments of a compound of Formula (I), Ring A taken with X and Y is pyrrolidinyl or furanyl. In some embodiments of a compound of Formula (I), Ring A taken with X and Y is a 5-membered heteroaryl. In some embodiments of a compound of Formula (I), Ring A taken with X and Y is pyrrolyl, pyrazolyl, imidazolyl, or triazolyl.

In some embodiments of a compound of Formula (I), Ring A taken with X and Y is pyrazolyl or imidazolyl. In some embodiments of a compound of Formula (I), Ring A taken with X and Y is furanyl.

In some embodiments of a compound of Formula (I), X is C. In some embodiments of a compound of Formula (I), X is CH. In some embodiments of a compound of Formula (I), X is N.

In some embodiments of a compound of Formula (I), Y is C. In some embodiments of a compound of Formula (I), Y is CH. In some embodiments of a compound of Formula (I), Y is N.

In some embodiments of a compound of Formula (I), the compound is of Formula (Ia):

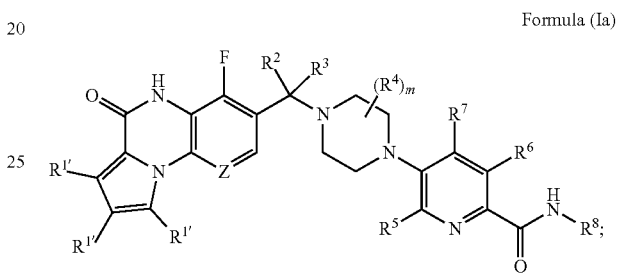

Formula (Ia)

wherein $R^{1'}$ is hydrogen or $R^1$.

In some embodiments of a compound of Formula (I), the compound is of Formula (Ib):

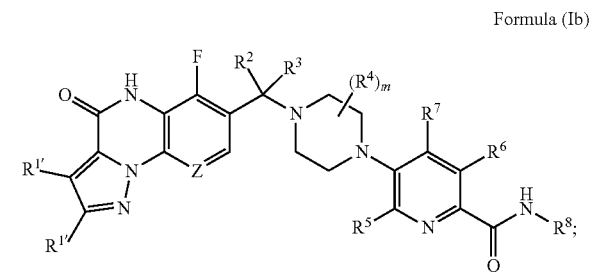

Formula (Ib)

wherein $R^{1'}$ is hydrogen or $R^1$.

In some embodiments of a compound of Formula (I), the compound is of Formula (Ic):

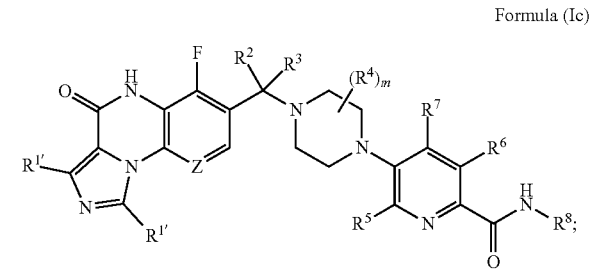

Formula (Ic)

wherein $R^{1'}$ is hydrogen or $R^1$.

In some embodiments of a compound of Formula (I), the compound is of Formula (Id):

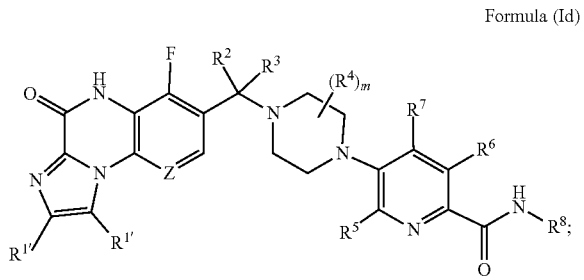

Formula (Id)

wherein R[1'] is hydrogen or R[1].

In some embodiments of a compound of Formula (I), the compound is of Formula (Ie):

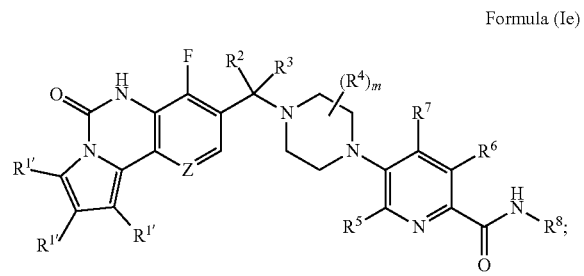

Formula (Ie)

wherein R[1'] is hydrogen or R[1].

In some embodiments of a compound of Formula (I), the compound is of Formula (If):

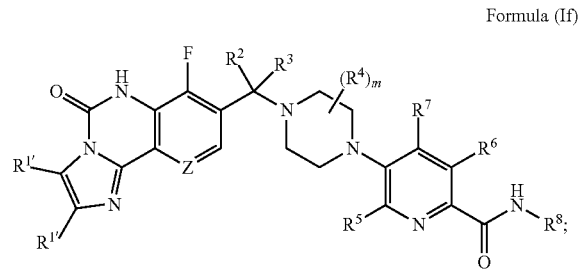

Formula (If)

wherein R[1'] is hydrogen or R[1].

In some embodiments of a compound of Formula (I), the compound is of Formula (Ig):

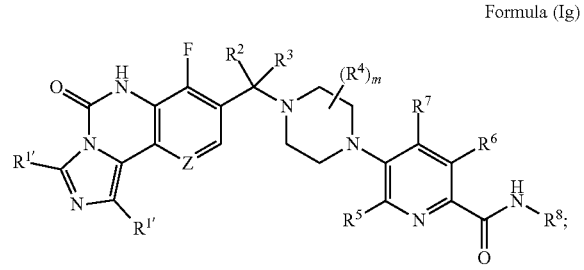

Formula (Ig)

wherein R[1'] is hydrogen or R[1].

In some embodiments of a compound of Formula (I), the compound is of Formula (Ih):

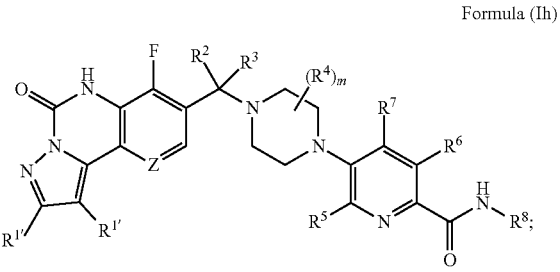

Formula (Ih)

wherein R[1'] is hydrogen or R[1].

In some embodiments of a compound of Formula (I), the compound is of Formula (Ii):

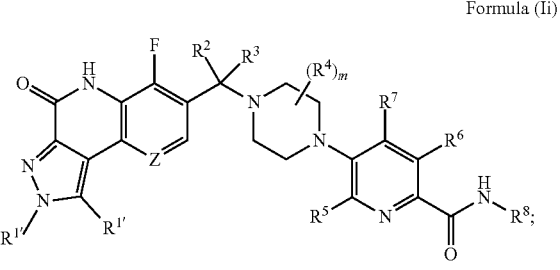

Formula (Ii)

wherein R[1'] is hydrogen or R[1].

In some embodiments of a compound of Formula (I), the compound is of Formula (Ij):

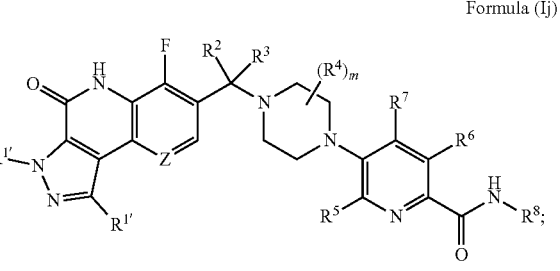

Formula (Ij)

wherein R[1'] is hydrogen or R[1].

In some embodiments of a compound of Formula (I), the compound is of Formula (Ik):

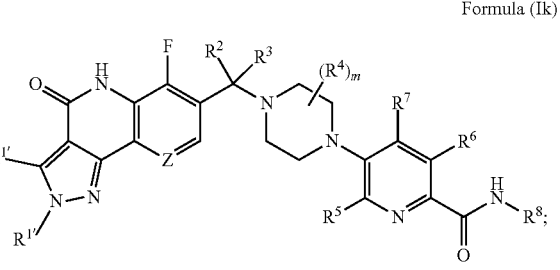

Formula (Ik)

wherein R[1'] is hydrogen or R[1].

In some embodiments of a compound of Formula (I), the compound is of Formula (II):

Formula (II)

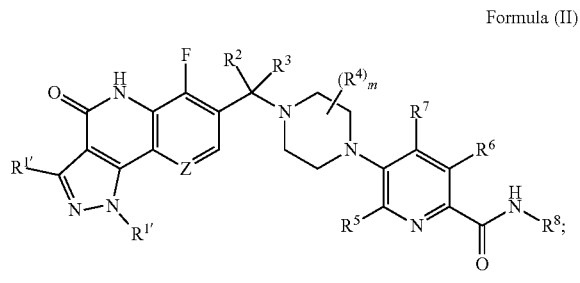

wherein R¹' is hydrogen or R¹.

In some embodiments of a compound of Formula (I), the compound is of Formula (Im):

(Formula Im)

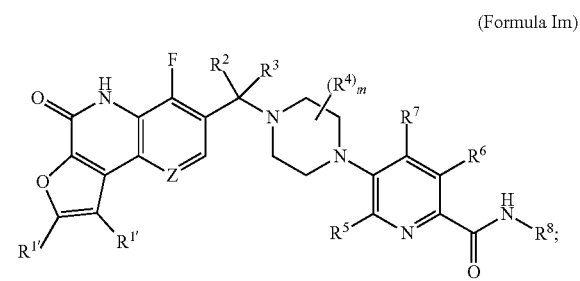

wherein R¹' is hydrogen or R¹.

In some embodiments of a compound of Formula (I), the compound is of Formula (In):

Formula (In)

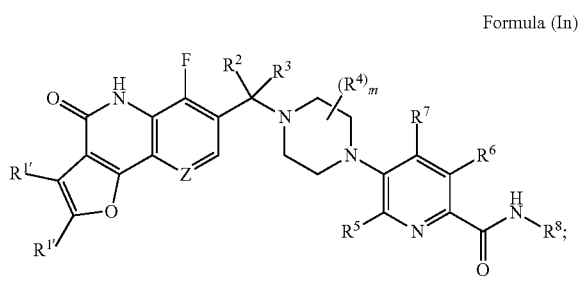

wherein R¹' is hydrogen or R¹.

In some embodiments of a compound of Formula (I), the compound is of Formula (Io):

Formula (Io)

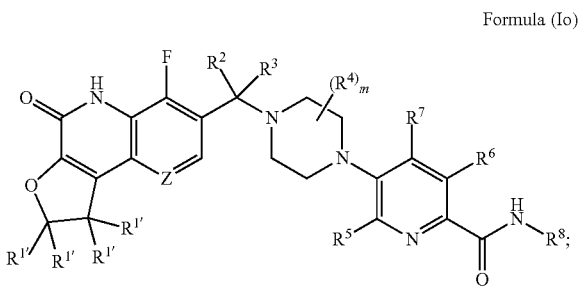

wherein R¹' is hydrogen or R¹.

In some embodiments of a compound of Formula (I), the compound is of Formula (Ip):

Formula (Ip)

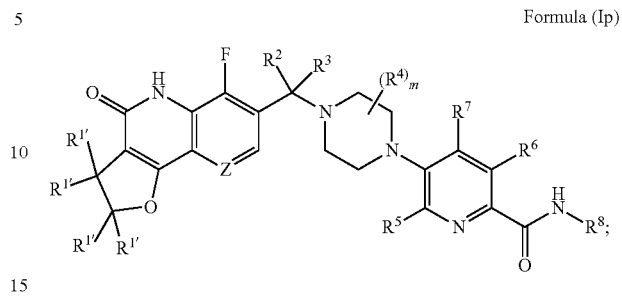

wherein R¹' is hydrogen or R¹.

In some embodiments of a compound of Formula (I), the compound is of Formula (Iq):

Formula (Iq)

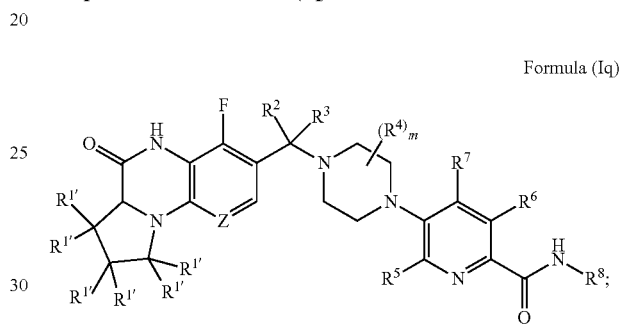

wherein R¹' is hydrogen or R¹.

In some embodiments of a compound of Formula (I), the compound is of Formula (Ir):

Formula (Ir)

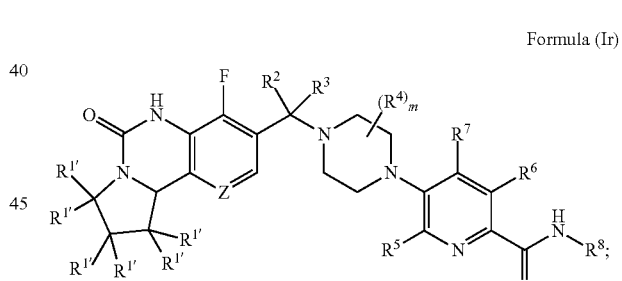

wherein R¹' is hydrogen or R¹.

In some embodiments of a compound of Formula (I), or a pharmaceutically acceptable salt, solvate, or stereoisomer thereof, the compound is of Formula (Ia)-(II):

Formula (Ia)

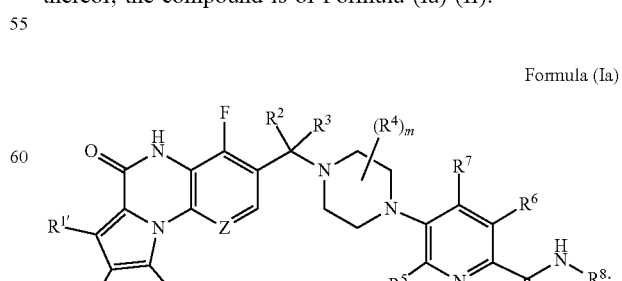

-continued
Formula (Ib)
Formula (Ic)
Formula (Id)
Formula (Ie)
Formula (If)
Formula (Ig)
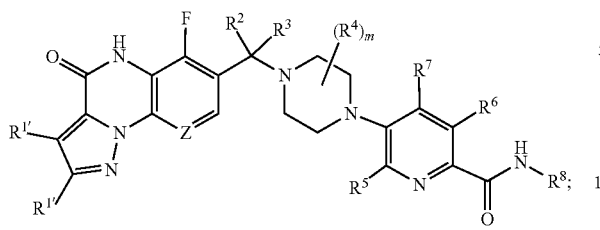
-continued
Formula (Ih)
Formula (Ii)
Formula (Ij)
Formula (Ik)
Formula (Il)
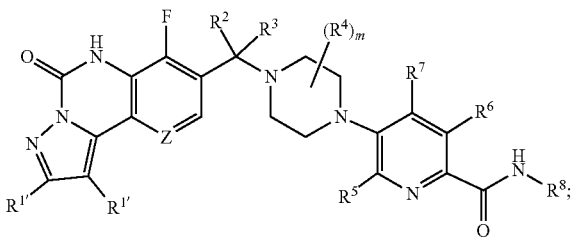
wherein $R^{1'}$ is hydrogen or $R^1$.
In some embodiments of a compound of Formula (I), or a pharmaceutically acceptable salt, solvate, or stereoisomer thereof, the compound is of Formula (Ia)-(Ih):

Formula (Ia)
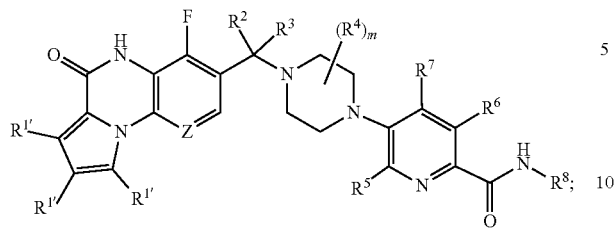
Formula (Ib)
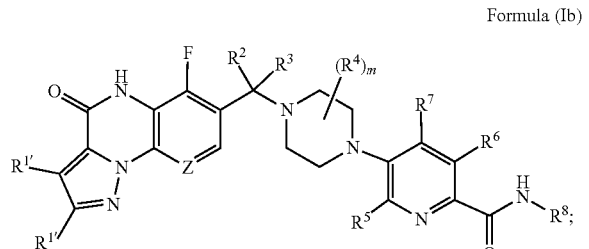
Formula (Ic)
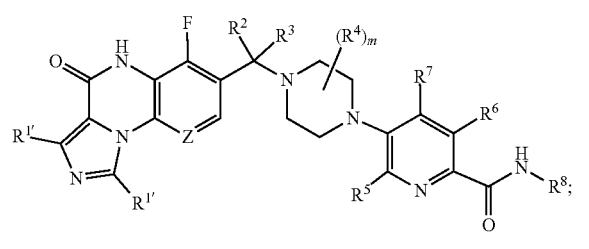
Formula (Id)
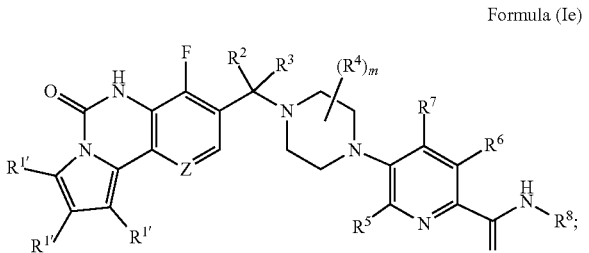
Formula (Ie)
Formula (If)
Formula (Ig)
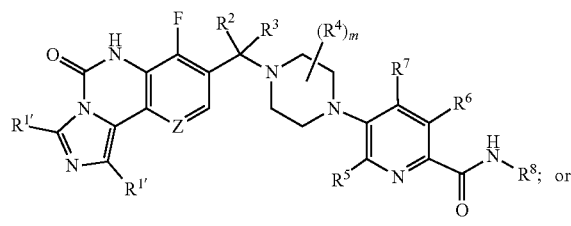
Formula (Ih)
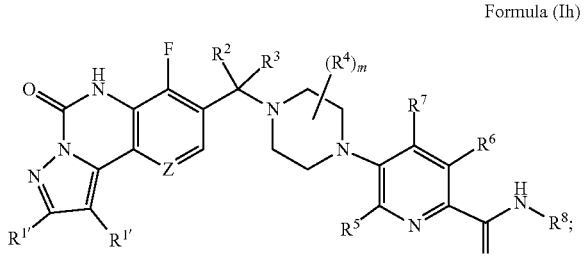
wherein $R^{1'}$ is hydrogen or $R^1$.
In some embodiments of a compound of Formula (I), or a pharmaceutically acceptable salt, solvate, or stereoisomer thereof, the compound is of Formula (Ii)-(Il):
Formula (Ii)
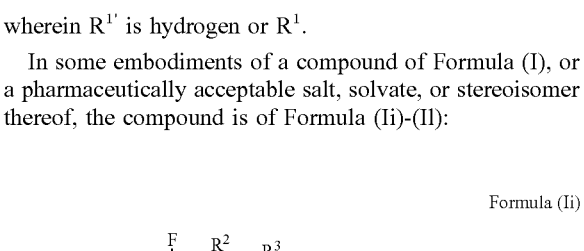
Formula (Ij)
Formula (Ik)

Formula (Il)

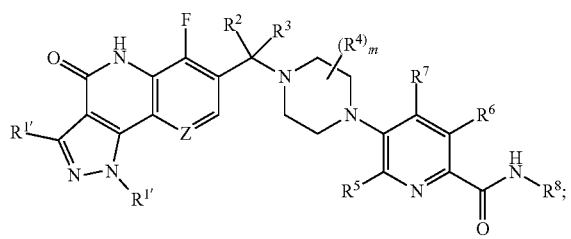

wherein R¹' is hydrogen or R¹.

In some embodiments of a compound of Formula (I), or a pharmaceutically acceptable salt, solvate, or stereoisomer thereof, the compound is of Formula (Im) or (In):

Formula (Im)

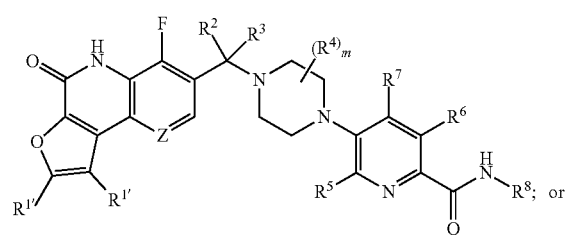

Formula (In)

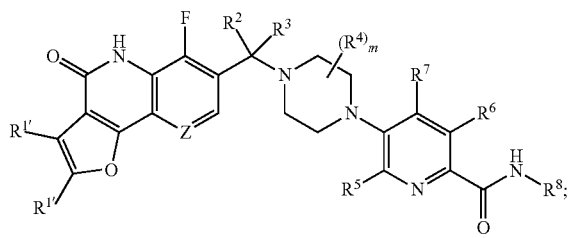

wherein R¹' is hydrogen or R¹.

In some embodiments of a compound of Formula (I), or a pharmaceutically acceptable salt, solvate, or stereoisomer thereof, the compound is of Formula (Io)-(Ir):

Formula (Io)

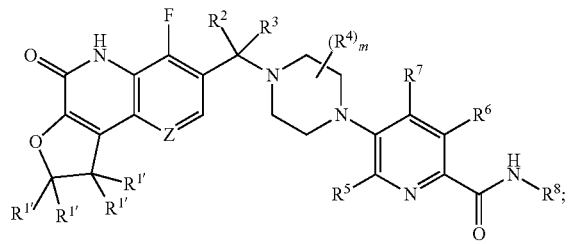

Formula (Ip)

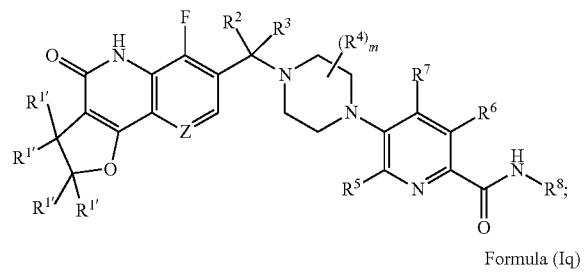

Formula (Iq)

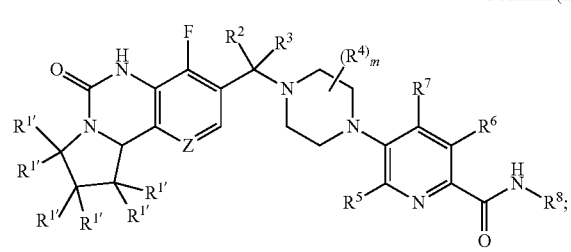

Formula (Ir)

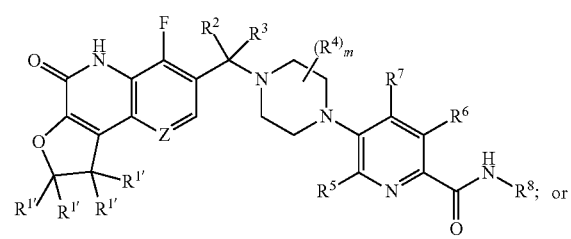

wherein R¹' is hydrogen or R¹.

In some embodiments of a compound of Formula (I), or a pharmaceutically acceptable salt, solvate, or stereoisomer thereof, the compound is of Formula (Io) or (Ip):

Formula (Io)

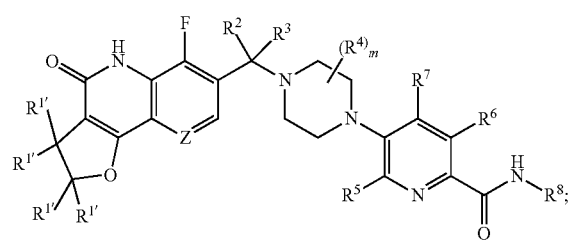

Formula (Ip)

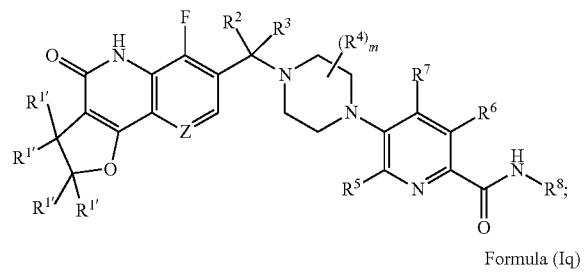

wherein R¹' is hydrogen or R¹.

In some embodiments of a compound of Formula (I), or a pharmaceutically acceptable salt, solvate, or stereoisomer thereof, the compound is of Formula (Iq) or (Ir):

(Formula (Iq))

[Chemical structure of Formula (Iq)]

Formula (Ir)

[Chemical structure of Formula (Ir)]

wherein $R^{1'}$ is hydrogen or $R^1$.

In some embodiments of a compound of Formula (I) or (Ia)-(Ir), each $R^1$ is independently deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R. In some embodiments of a compound of Formula (I) or (Ia)-(Ir), each $R^1$ is independently deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl. In some embodiments of a compound of Formula (I) or (Ia)-(Ir), each $R^1$ is independently deuterium, $C_1$-$C_6$alkyl, $C_1$-$C_6$haloalkyl, $C_1$-$C_6$ deuteroalkyl, $C_1$-$C_6$ heteroalkyl, cycloalkyl, or heterocycloalkyl. In some embodiments of a compound of Formula (I) or (Ia)-(Ir), each $R^1$ is independently deuterium, halogen, $C_1$-$C_6$alkyl, $C_1$-$C_6$haloalkyl, $C_1$-$C_6$ deuteroalkyl; wherein the alkyl is optionally substituted with one or more R In some embodiments of a compound of Formula (I) or (Ia)-(Ir), each $R^1$ is independently deuterium, halogen, or $C_1$-$C_6$alkyl. In some embodiments of a compound of Formula (I) or (Ia)-(Ir), each $R^1$ is independently halogen or $C_1$-$C_6$alkyl. In some embodiments of a compound of Formula (I) or (Ia)-(Ir), each $R^1$ is independently halogen. In some embodiments of a compound of Formula (I) or (Ia)-(Ir), each $R^1$ is independently $C_1$-$C_6$alkyl.

In some embodiments of a compound of Formula (I) or (Ia)-(Ir), each $R^{1'}$ is independently hydrogen, deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R. In some embodiments of a compound of Formula (I) or (Ia)-(Ir), $R^{1'}$ is independently hydrogen, deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl. In some embodiments of a compound of Formula (Ia)-(Ir), each $R^{1'}$ is independently hydrogen, deuterium, $C_1$-$C_6$alkyl, $C_1$-$C_6$haloalkyl, $C_1$-$C_6$ deuteroalkyl, $C_1$-$C_6$ heteroalkyl, cycloalkyl, or heterocycloalkyl. In some embodiments of a compound of Formula (Ia)-(Ir), each $R^{1'}$ is independently hydrogen, deuterium, halogen, $C_1$-$C_6$alkyl, $C_1$-$C_6$haloalkyl, $C_1$-$C_6$ deuteroalkyl; wherein the alkyl is optionally substituted with one or more R. In some embodiments of a compound of Formula (Ia)-(Ir), each $R^{1'}$ is independently hydrogen, deuterium, halogen, or $C_1$-$C_6$alkyl. In some embodiments of a compound of Formula (Ia)-(Ir), each $R^{1'}$ is independently hydrogen, halogen, or $C_1$-$C_6$alkyl. In some embodiments of a compound of Formula (Ia)-(Ir), each $R^{1'}$ is independently hydrogen or halogen. In some embodiments of a compound of Formula (Ia)-(Ir), each $R^{1'}$ is independently hydrogen or $C_1$-$C_6$alkyl. In some embodiments of a compound of Formula (Ia)-(Ir), each $R^{1'}$ is hydrogen. In some embodiments of a compound of Formula (Ia)-(Ir), each $R^{1'}$ is independently $C_1$-$C_6$alkyl.

In some embodiments of a compound of Formula (I) or (Ia)-(Ir), n is 0-4. In some embodiments of a compound of Formula (I) or (Ia)-(Ir), n is 0-3. In some embodiments of a compound of Formula (I) or (Ia)-(Ir), n is 0-2. In some embodiments of a compound of Formula (I) or (Ia)-(Ir), n is 0 or 1. In some embodiments of a compound of Formula (I) or (Ia)-(Ir), n is 0. In some embodiments of a compound of Formula (I) or (Ia)-(Ir), n is 1. In some embodiments of a compound of Formula (I) or (Ia)-(Ir), n is 2. In some embodiments of a compound of Formula (I) or (Ia)-(Ir), n is 3. In some embodiments of a compound of Formula (I) or (Ia)-(Ir), n is 4.

In some embodiments of a compound of Formula (I) or (Ia)-(Ir), Z is N. In some embodiments of a compound of Formula (I) or (Ia)-(Ir), Z is $CR^Z$.

In some embodiments of a compound of Formula (I) or (Ia)-(Ir), $R^Z$ is hydrogen, deuterium, halogen, $C_1$-$C_6$alkyl, $C_1$-$C_6$haloalkyl, or $C_1$-$C_6$ deuteroalkyl; wherein the alkyl heterocycloalkyl is optionally substituted with one or more R. In some embodiments of a compound of Formula (I) or (Ia)-(Ir), $R^Z$ is hydrogen, deuterium, halogen, or $C_1$-$C_6$alkyl. In some embodiments of a compound of Formula (I) or (Ia)-(Ir), $R^Z$ is hydrogen. In some embodiments of a compound of Formula (I) or (Ia)-(Ir), $R^Z$ is halogen. In some embodiments of a compound of Formula (I) or (Ia)-(Ir), $R^Z$ is $C_1$-$C_6$alkyl.

In some embodiments of a compound of Formula (I) or (Ia)-(Ir), $R^2$ is hydrogen, deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R. In some embodiments of a compound of Formula (I) or (Ia)-(Ir), $R^2$ is hydrogen, deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl. In some embodiments of a compound of Formula (I) or (Ia)-(Ir), $R^2$ is hydrogen, deuterium, $C_1$-$C_6$alkyl, $C_1$-$C_6$haloalkyl, $C_1$-$C_6$ deuteroalkyl, cycloalkyl, or heterocycloalkyl. In some embodiments of a compound of Formula (I) or (Ia)-(Ir), $R^2$ is hydrogen, deuterium, halogen, $C_1$-$C_6$alkyl, or $C_1$-$C_6$haloalkyl. In some embodiments of a compound of Formula (I) or (Ia)-(Ir), $R^2$ is hydrogen, deuterium, or $C_1$-$C_6$alkyl. In some embodiments of a compound of Formula (I) or (Ia)-(Ir), $R^2$ is hydrogen or deuterium. In some embodiments of a compound of Formula (I) or (Ia)-(Ir), $R^2$ is deuterium or $C_1$-$C_6$alkyl. In some embodiments of a compound of Formula (I) or (Ia)-(Ir), $R^2$ is hydrogen or $C_1$-$C_6$alkyl. In some embodiments of a compound of Formula (I) or (Ia)-(Ir), $R^2$ is hydrogen. In some embodiments of a compound of Formula (I) or (Ia)-(Ir), $R^2$ is deuterium. In some embodiments of a compound of Formula (I) or (Ia)-(Ir), $R^2$ is $C_1$-$C_6$alkyl.

In some embodiments of a compound of Formula (I) or (Ia)-(Ir), $R^3$ is hydrogen, deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein the alkyl, cycloalkyl, and heterocycloalkyl is optionally substituted with one or more R. In some embodiments of a compound of Formula (I) or (Ia)-(Ir), $R^3$ is hydrogen, deuterium, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl. In some embodiments of a compound of Formula (I) or (Ia)-(Ir), $R^3$ is hydrogen, deuterium, $C_1$-$C_6$alkyl, $C_1$-$C_6$haloalkyl, $C_1$-$C_6$ deuteroalkyl, cycloalkyl, or heterocycloalkyl. In some embodiments of a compound of Formula (I) or (Ia)-(Ir), $R^3$ is hydrogen, deuterium, halogen, $C_1$-$C_6$alkyl, or $C_1$-$C_6$haloalkyl. In some embodiments of a compound of Formula (I) or (Ia)-(Ir), $R^3$ is hydrogen, deuterium, or $C_1$-$C_6$alkyl. In some embodiments of a compound of Formula (I) or (Ia)-(Ir), $R^3$ is hydrogen or deuterium. In some embodiments of a compound of Formula (I) or (Ia)-(Ir), $R^3$ is deuterium or $C_1$-$C_6$alkyl. In some embodiments of a compound of Formula (I) or (Ia)-(Ir), $R^3$ is hydrogen or $C_1$-$C_6$alkyl. In some embodiments of a compound of Formula (I) or (Ia)-(Ir), $R^3$ is hydrogen. In some embodiments of a compound of Formula (I) or (Ia)-(Ir), $R^3$ is deuterium. In some embodiments of a compound of Formula (I) or (Ia)-(Ir), $R^3$ is $C_1$-$C_6$alkyl.

In some embodiments of a compound of Formula (I) or (Ia)-(Ir), $R^2$ is hydrogen and $R^3$ is hydrogen.

In some embodiments of a compound of Formula (I) or (Ia)-(Ir), $R^2$ and $R^3$ are taken together to form a cycloalkyl.

In some embodiments of a compound of Formula (I) or (Ia)-(Ir), each $R^4$ is independently deuterium, $C_1$-$C_6$alkyl, or $C_1$-$C_6$haloalkyl. In some embodiments of a compound of Formula (I) or (Ia)-(Ir), each $R^4$ is independently $C_1$-$C_6$alkyl.

In some embodiments of a compound of Formula (I) or (Ia)-(Ir), two $R^4$ on the same carbon or different carbons are taken together to form a cycloalkyl. In some embodiments of a compound of Formula (I) or (Ia)-(Ir), two $R^4$ on the same carbon are taken together to form a cycloalkyl. In some embodiments of a compound of Formula (I) or (Ia)-(Ir), two $R^4$ on different carbons are taken together to form a cycloalkyl.

In some embodiments of a compound of Formula (I) or (Ia)-(Ir), m is 0-2. In some embodiments of a compound of Formula (I) or (Ia)-(Ir), m is 0 or 1. In some embodiments of a compound of Formula (I) or (Ia)-(Ir), m is 0. In some embodiments of a compound of Formula (I) or (Ia)-(Ir), m is 1. In some embodiments of a compound of Formula (I) or (Ia)-(Ir), m is 2.

In some embodiments of a compound of Formula (I) or (Ia)-(Ir), $R^5$ is hydrogen, deuterium, halogen, —CN, $C_1$-$C_6$alkyl, $C_1$-$C_6$haloalkyl, or $C_1$-$C_6$ deuteroalkyl. In some embodiments of a compound of Formula (I) or (Ia)-(Ir), $R^5$ is hydrogen, deuterium, halogen, or $C_1$-$C_6$alkyl. In some embodiments of a compound of Formula (I) or (Ia)-(Ir), $R^5$ is hydrogen, halogen, or $C_1$-$C_6$alkyl.

In some embodiments of a compound of Formula (I) or (Ia)-(Ir), $R^5$ is hydrogen. In some embodiments of a compound of Formula (I) or (Ia)-(Ir), $R^5$ is halogen.

In some embodiments of a compound of Formula (I) or (Ia)-(Ir), $R^6$ is hydrogen, deuterium, halogen, —CN, $C_1$-$C_6$alkyl, $C_1$-$C_6$haloalkyl, or $C_1$-$C_6$ deuteroalkyl. In some embodiments of a compound of Formula (I) or (Ia)-(Ir), $R^6$ is hydrogen, deuterium, halogen, or $C_1$-$C_6$alkyl. In some embodiments of a compound of Formula (I) or (Ia)-(Ir), $R^6$ is hydrogen, halogen, or $C_1$-$C_6$alkyl. In some embodiments of a compound of Formula (I) or (Ia)-(Ir), $R^6$ is hydrogen. In some embodiments of a compound of Formula (I) or (Ia)-(Ir), $R^6$ is halogen.

In some embodiments of a compound of Formula (I) or (Ia)-(Ir), $R^7$ is hydrogen, deuterium, halogen, —CN, $C_1$-$C_6$alkyl, $C_1$-$C_6$haloalkyl, or $C_1$-$C_6$ deuteroalkyl. In some embodiments of a compound of Formula (I) or (Ia)-(Ir), $R^7$ is hydrogen, deuterium, halogen, or $C_1$-$C_6$alkyl. In some embodiments of a compound of Formula (I) or (Ia)-(Ir), $R^7$ is hydrogen, halogen, or $C_1$-$C_6$alkyl. In some embodiments of a compound of Formula (I) or (Ia)-(Ir), $R^7$ is hydrogen. In some embodiments of a compound of Formula (I) or (Ia)-(Ir), $R^7$ is halogen.

In some embodiments of a compound of Formula (I) or (Ia)-(Ir), $R^8$ is $C_1$-$C_6$alkyl, $C_1$-$C_6$haloalkyl, $C_1$-$C_6$ deuteroalkyl, cycloalkyl, or heterocycloalkyl; wherein the alkyl, cycloalkyl, and heterocycloalkyl is optionally substituted with one or more R. In some embodiments of a compound of Formula (I) or (Ia)-(Ir), $R^8$ is $C_1$-$C_6$alkyl, $C_1$-$C_6$haloalkyl, or cycloalkyl; wherein the alkyl and cycloalkyl is optionally substituted with one or more R. In some embodiments of a compound of Formula (I) or (Ia)-(Ir), $R^8$ is $C_1$-$C_6$alkyl, $C_1$-$C_6$haloalkyl, or cycloalkyl. In some embodiments of a compound of Formula (I) or (Ia)-(Ir), $R^8$ is $C_1$-$C_6$alkyl or cycloalkyl; wherein the alkyl and cycloalkyl is optionally substituted with one or more R. In some embodiments of a compound of Formula (I) or (Ia)-(Ir), $R^8$ is $C_1$-$C_6$alkyl or cycloalkyl. In some embodiments of a compound of Formula (I) or (Ia)-(Ir), $R^8$ is $C_1$-$C_6$alkyl. In some embodiments of a compound of Formula (I) or (Ia)-(Ir), $R^8$ is methyl. In some embodiments of a compound of Formula (I) or (Ia)-(Ir), $R^8$ is cycloalkyl. In some embodiments of a compound of Formula (I) or (Ia)-(Ir), $R^8$ is cyclopropyl.

In some embodiments of a compound disclosed herein, each $R^a$ is independently $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein each alkyl, cycloalkyl, and heterocycloalkyl is independently optionally substituted with one or more R. In some embodiments of a compound disclosed herein, each $R^a$ is independently $C_1$-$C_6$alkyl, $C_1$-$C_6$haloalkyl, $C_1$-$C_6$ deuteroalkyl, cycloalkyl, or heterocycloalkyl; wherein each alkyl, cycloalkyl, and heterocycloalkyl is independently optionally substituted with one or more R. In some embodiments of a compound disclosed herein, each $R^a$ is independently $C_1$-$C_6$alkyl, $C_1$-$C_6$haloalkyl, or $C_1$-$C_6$ deuteroalkyl; wherein each alkyl is independently optionally substituted with one or more R. In some embodiments of a compound disclosed herein, each $R^a$ is independently $C_1$-$C_6$alkyl, $C_1$-$C_6$haloalkyl, or $C_1$-$C_6$ deuteroalkyl. In some embodiments of a compound disclosed herein, each $R^a$ is independently $C_1$-$C_6$alkyl, or $C_1$-$C_6$haloalkyl. In some embodiments of a compound disclosed herein, each $R^a$ is independently $C_1$-$C_6$alkyl.

In some embodiments of a compound disclosed herein, each $R^c$ and $R^d$ are independently hydrogen, $C_1$-$C_6$alkyl, $C_1$-$C_6$haloalkyl, $C_1$-$C_6$ deuteroalkyl, $C_1$-$C_6$ hydroxyalkyl, $C_1$-$C_6$ aminoalkyl, $C_1$-$C_6$ heteroalkyl, cycloalkyl, or heterocycloalkyl; wherein each alkyl, cycloalkyl, and heterocycloalkyl is independently optionally substituted with one or more R. In some embodiments of a compound disclosed herein, each $R^c$ and $R^d$ are independently hydrogen, $C_1$-$C_6$alkyl, $C_1$-$C_6$haloalkyl, $C_1$-$C_6$ deuteroalkyl, cycloalkyl, or heterocycloalkyl; wherein each alkyl, cycloalkyl, and heterocycloalkyl is independently optionally substituted with one or more R. In some embodiments of a compound disclosed herein, each $R^c$ and $R^d$ are independently hydrogen, C₁-C₆alkyl, C₁-C₆haloalkyl, or C₁-C₆ deuteroalkyl; wherein each alkyl is independently optionally substituted with one or more R. In some embodiments of a compound disclosed herein, each $R^c$ and $R^d$ are independently hydrogen, C₁-C₆alkyl, C₁-C₆haloalkyl, or C₁-C₆ deuteroalkyl. In some embodiments of a compound disclosed herein, each $R^c$ and $R^d$ are independently hydrogen, C₁-C₆alkyl, or C₁-C₆haloalkyl. In some embodiments of a compound disclosed herein, each $R^c$ and $R^d$ are independently hydrogen or C₁-C₆alkyl. In some embodiments of a compound disclosed herein, each $R^c$ and $R^d$ are independently hydrogen. In some embodiments of a compound disclosed herein, each $R^c$ and $R^d$ are independently C₁-C₆alkyl.

In some embodiments of a compound disclosed herein, $R^c$ and $R^d$ are taken together with the atom to which they are attached to form a heterocycloalkyl optionally substituted with one or more R.

In some embodiments of a compound disclosed herein, each R is independently halogen, —CN, —OH, —OC₁-C₃alkyl, —OC₁-C₃haloalkyl, —NH₂, —NHC₁-C₃alkyl, —N(C₁-C₃alkyl)₂, —C(=O)C₁-C₃alkyl, —C(=O)OH, —C(=O)OC₁-C₃alkyl, —C(=O)NH₂, —C(=O)NHC₁-C₃alkyl, —C(=O)N(C₁-C₃alkyl)₂, C₁-C₃alkyl, C₁-C₃haloalkyl, C₁-C₃ deuteroalkyl, C₁-C₃ hydroxyalkyl, C₁-C₃ aminoalkyl, C₁-C₃ heteroalkyl, or C₃-C₆cycloalkyl; or two R on the same atom are taken together to form an oxo. In some embodiments of a compound disclosed herein, each R is independently halogen, —CN, —OH, —OC₁-C₃alkyl, —OC₁-C₃haloalkyl, —NH₂, C₁-C₃alkyl, C₁-C₃haloalkyl, C₁-C₃ deuteroalkyl, C₁-C₃ hydroxyalkyl, C₁-C₃ aminoalkyl, C₁-C₃ heteroalkyl, or C₃-C₆cycloalkyl; or two R on the same atom are taken together to form an oxo. In some embodiments of a compound disclosed herein, each R is independently halogen, —CN, —OH, —OC₁-C₃alkyl, —NH₂, C₁-C₃alkyl, or C₁-C₃haloalkyl; or two R on the same atom are taken together to form an oxo. In some embodiments of a compound disclosed herein, each R is independently halogen, —CN, —OH, —OC₁-C₃alkyl, —NH₂, C₁-C₃alkyl; or two R on the same atom are taken together to form an oxo. In some embodiments of a compound disclosed herein, each R is independently halogen or C₁-C₃alkyl.

Any combination of the groups described above for the various variables is contemplated herein. Throughout the specification, groups and substituents thereof are chosen by one skilled in the field to provide stable moieties and compounds.

In some embodiments, the compound disclosed herein, or a pharmaceutically acceptable salt, solvate, or stereoisomer thereof, is selected from a compound found in Table 1.

TABLE 1

| Ex. | Structure |
|---|---|
| 1 | 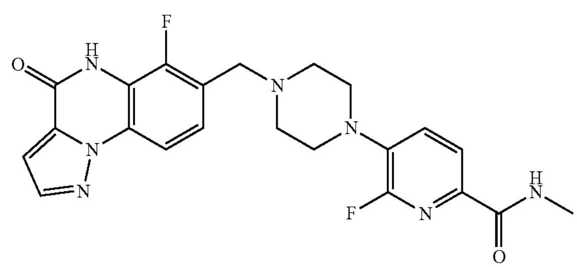 [SMILES: CNC(=O)c1ccc(N2CCN(Cc3ccc4c([nH]c(=O)c5ccnn54)c3F)CC2)c(F)n1] |
| 2 | 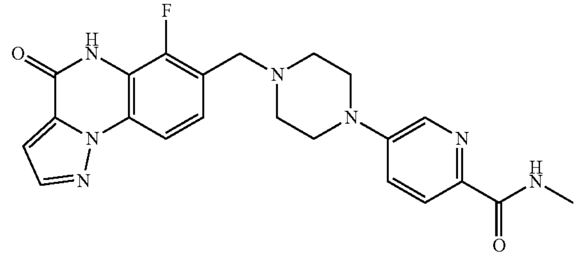 [SMILES: CNC(=O)c1ccc(N2CCN(Cc3ccc4c([nH]c(=O)c5ccnn54)c3F)CC2)cn1] |
| 3 | 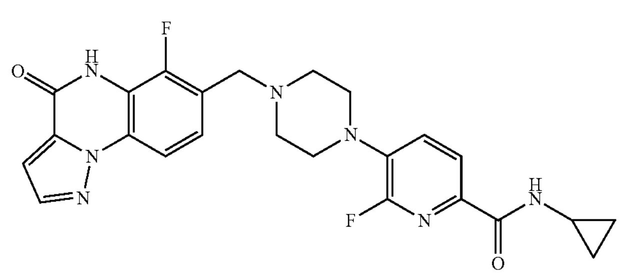 [SMILES: O=C(NC1CC1)c1ccc(N2CCN(Cc3ccc4c([nH]c(=O)c5ccnn54)c3F)CC2)c(F)n1] |

TABLE 1-continued
| Ex. | Structure |
|---|---|
| 4 | 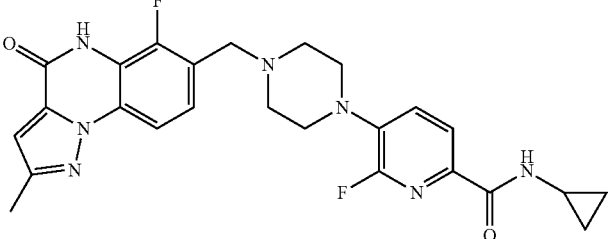 |
| 5 | 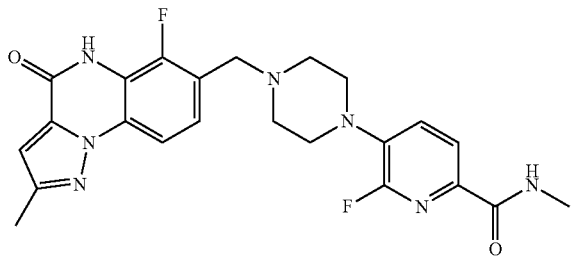 [SMILES: CNC(=O)c1ccc(N2CCN(Cc3ccc4c([nH]c(=O)c5cc(C)nn54)c3F)CC2)c(F)n1] |
| 6 | 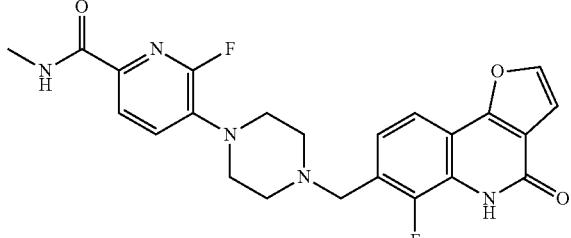 |
| 7 | 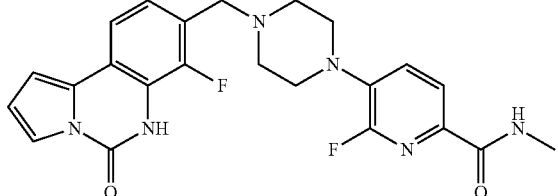 [SMILES: CNC(=O)c1ccc(N2CCN(Cc3ccc4c([nH]c(=O)n5cccc45)c3F)CC2)c(F)n1] |
| 8 | 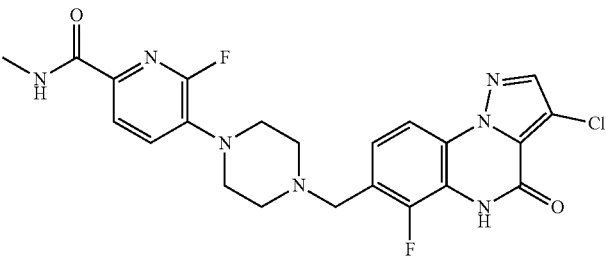 [SMILES: CNC(=O)c1ccc(N2CCN(Cc3ccc4c([nH]c(=O)c5c(Cl)cnn54)c3F)CC2)c(F)n1] |
| 9 | 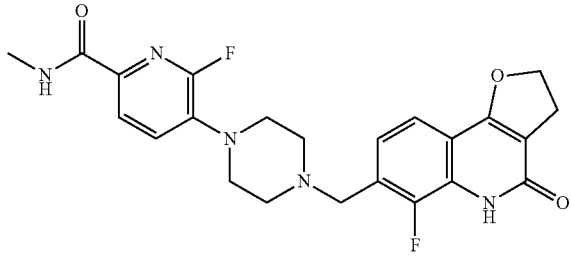 [SMILES: CNC(=O)c1ccc(N2CCN(Cc3ccc4c5c(c(=O)[nH]c4c3F)CCO5)CC2)c(F)n1] |

TABLE 1-continued

| Ex. | Structure |
|---|---|
| 10 | 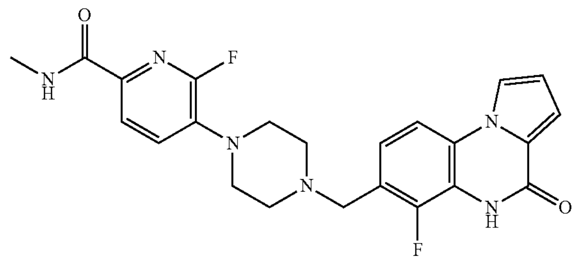 [SMILES: CNC(=O)c1ccc(N2CCN(Cc3ccc4c([nH]c(=O)c5cccn54)c3F)CC2)c(F)n1] |
| 11 | 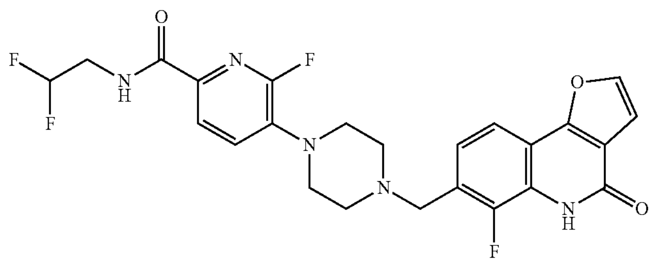 [SMILES: O=C(NCC(F)F)c1ccc(N2CCN(Cc3ccc4c([nH]c(=O)c5ccoc54)c3F)CC2)c(F)n1] |
| 12 | 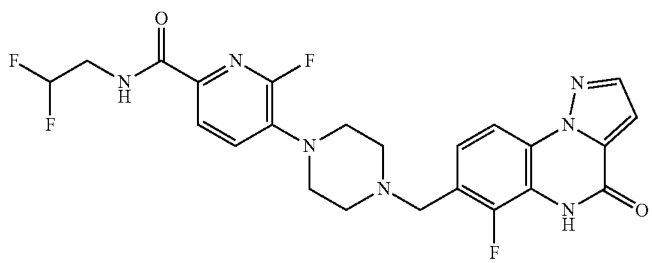 [SMILES: O=C(NCC(F)F)c1ccc(N2CCN(Cc3ccc4c([nH]c(=O)c5ccnn54)c3F)CC2)c(F)n1] |
| 13 | 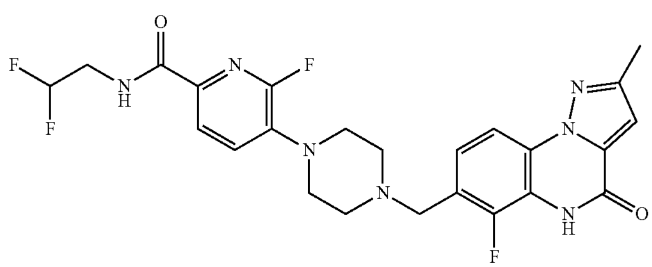 [SMILES: Cc1cc2c(=O)[nH]c3c(F)c(CN4CCN(c5ccc(C(=O)NCC(F)F)nc5F)CC4)ccc3n2n1] |
| 14 | 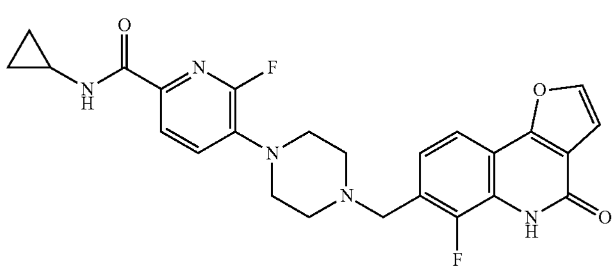 [SMILES: O=C(NC1CC1)c1ccc(N2CCN(Cc3ccc4c([nH]c(=O)c5ccoc54)c3F)CC2)c(F)n1] |
| 15 | 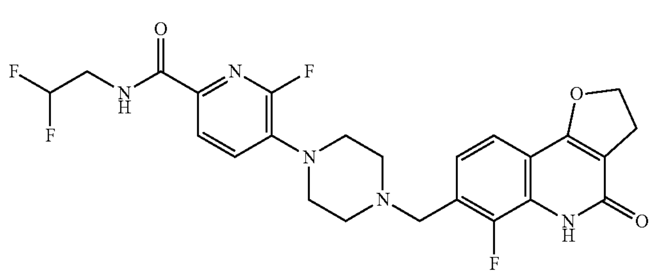 [SMILES: O=C(NCC(F)F)c1ccc(N2CCN(Cc3ccc4c5c(c(=O)[nH]c4c3F)CCO5)CC2)c(F)n1] |

TABLE 1-continued

| Ex. | Structure |
|---|---|
| 16 | 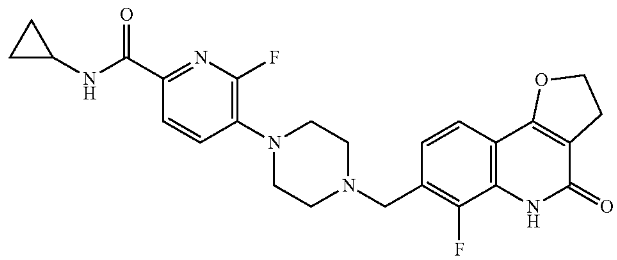 |
| 17 | 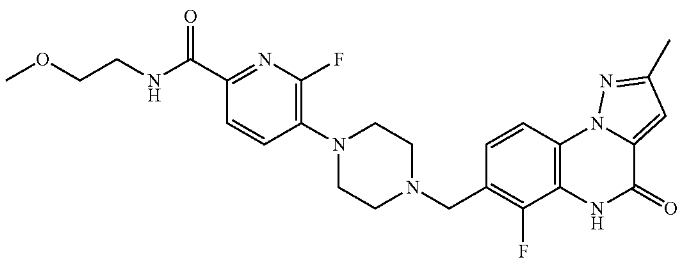 [SMILES: COCCNC(=O)c1ccc(N2CCN(Cc3ccc4c([nH]c(=O)c5cc(C)nn54)c3F)CC2)c(F)n1] |
| 18 | 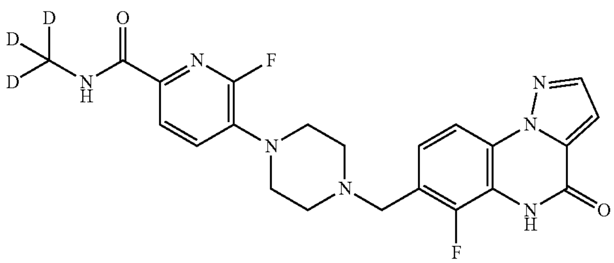 [SMILES: [2H]C([2H])([2H])NC(=O)c1ccc(N2CCN(Cc3ccc4c([nH]c(=O)c5ccnn54)c3F)CC2)c(F)n1] |
| 19 | 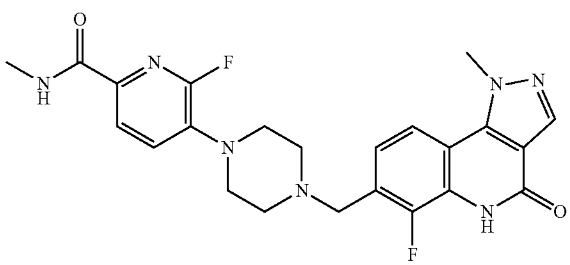 [SMILES: CNC(=O)c1ccc(N2CCN(Cc3ccc4c([nH]c(=O)c5cnn(C)c54)c3F)CC2)c(F)n1] |
| 20 | 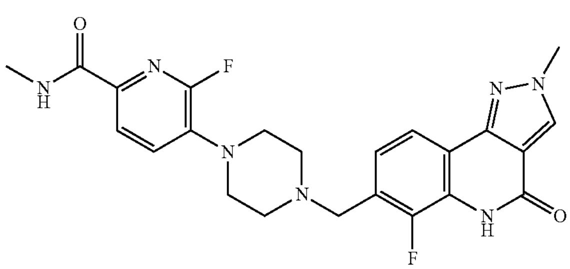 [SMILES: CNC(=O)c1ccc(N2CCN(Cc3ccc4c([nH]c(=O)c5cn(C)nc54)c3F)CC2)c(F)n1] |
| 21 | 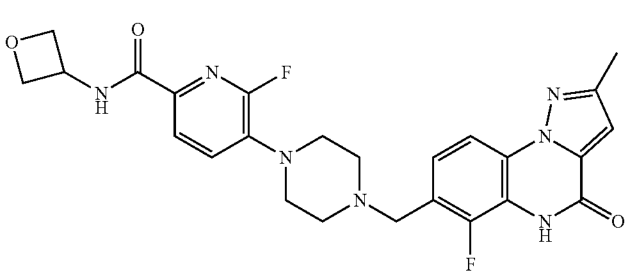 [SMILES: Cc1cc2c(=O)[nH]c3c(F)c(CN4CCN(c5ccc(C(=O)NC6COC6)nc5F)CC4)ccc3n2n1] |

TABLE 1-continued
| Ex. | Structure |
|---|---|
| 22 | 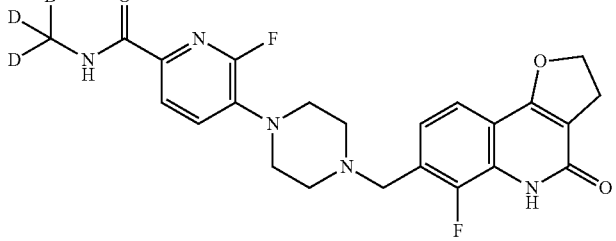 |
| 23 | 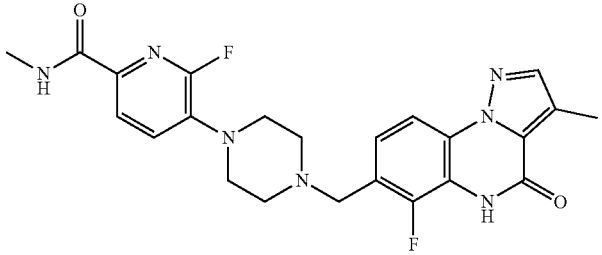 |
| 24 | 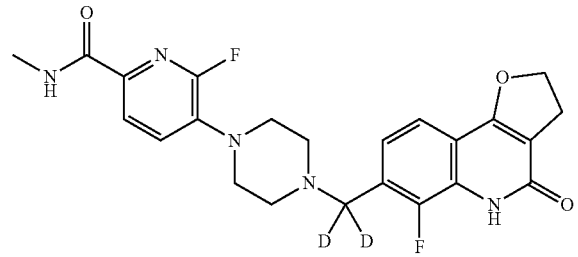 [SMILES: [2H]C([2H])(c1ccc2c3c(c(=O)[nH]c2c1F)CCO3)N1CCN(c2ccc(C(=O)NC)nc2F)CC1] |
| 25 | 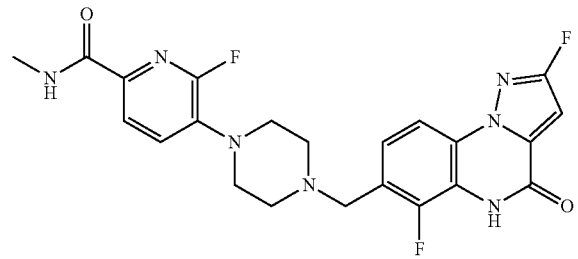 [SMILES: CNC(=O)c1ccc(N2CCN(Cc3ccc4c([nH]c(=O)c5cc(F)nn54)c3F)CC2)c(F)n1] |
| 26 | 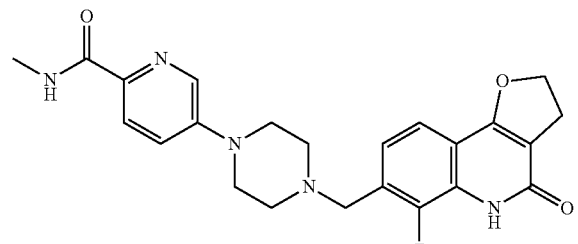 |
| 27 | 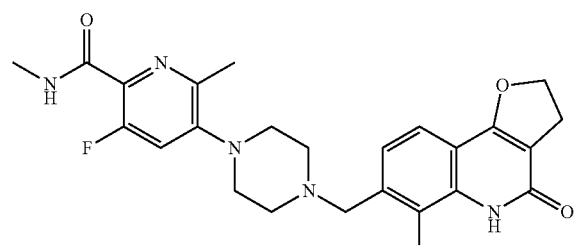 |

TABLE 1-continued
| Ex. | Structure |
|---|---|
| 28 | 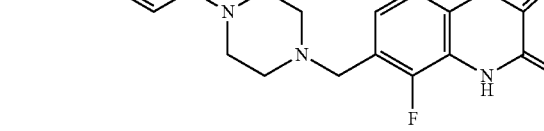 |
| 29 | 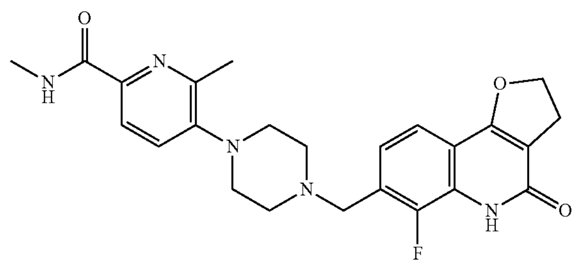 [SMILES: CNC(=O)c1ccc(N2CCN(Cc3ccc4c5c(c(=O)[nH]c4c3F)CCO5)CC2)c(C)n1] |
| 30 | 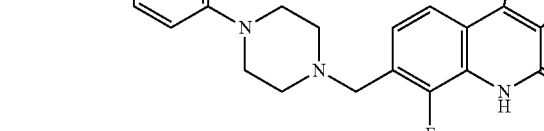 |
| 31 | 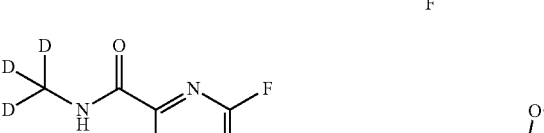 |
| 32 | 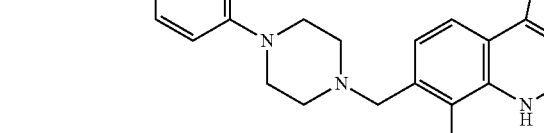 |
| 33 | 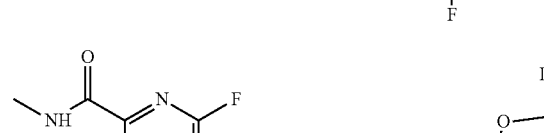 |

TABLE 1-continued

| Ex. | Structure |
|---|---|
| 34 | 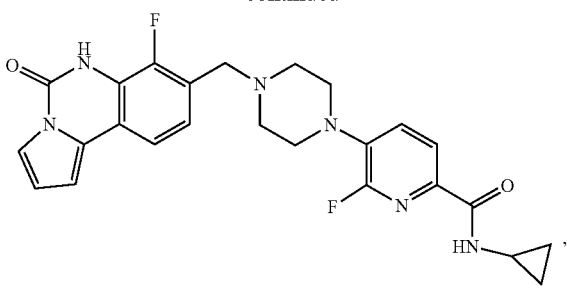 |

The absolute label (abs) is added to a chiral center to denote that it is unambiguously a pure sample of the drawn stereoisomer.

The OR label (or) denotes a pure substance, but the absolute configuration of the stereochemical center is unknown. After chiral separation with pure structures isolated, multiple OR labels (OR indicates purity) with the same numerical value will indicates that a sample is one of a pair of pure enantiomers (but the absolute configuration of the stereochemical center is unknown).

The AND label (and) denotes both isomers are present at the depicted stereochemical center. Assigning different numerical values to the AND labels denotes that they are independent of each other. The use of AND labels with the same values indicate that the two stereocenters are relative to each other and can only change in concert.

In some embodiments, the compound disclosed herein, or a pharmaceutically acceptable salt, solvate, or stereoisomer thereof, is selected from:

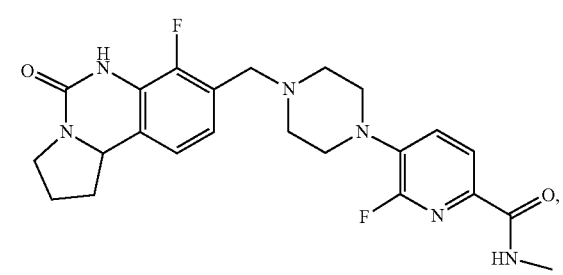

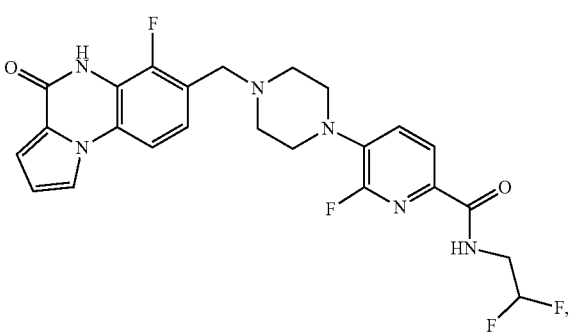

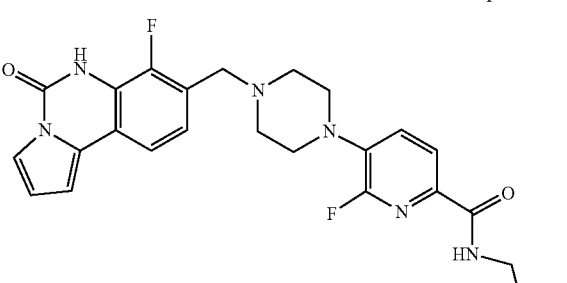

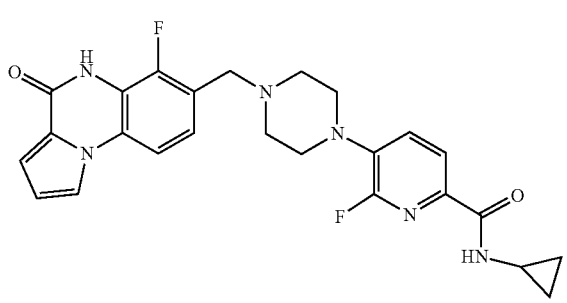

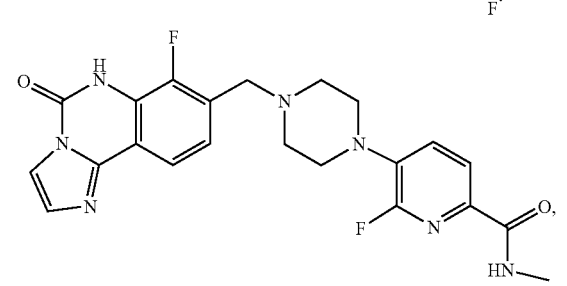

-continued
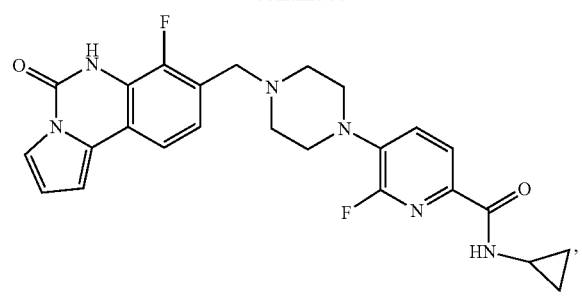
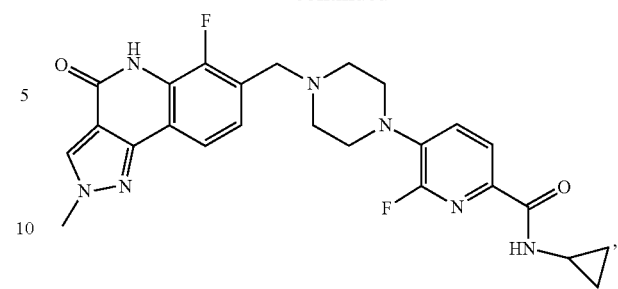
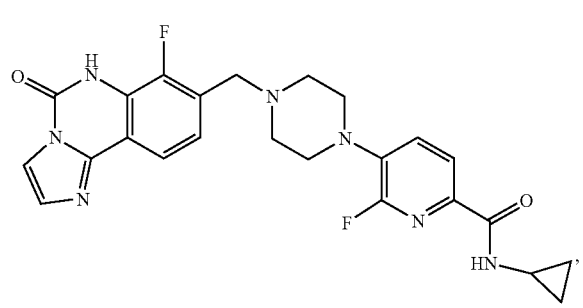
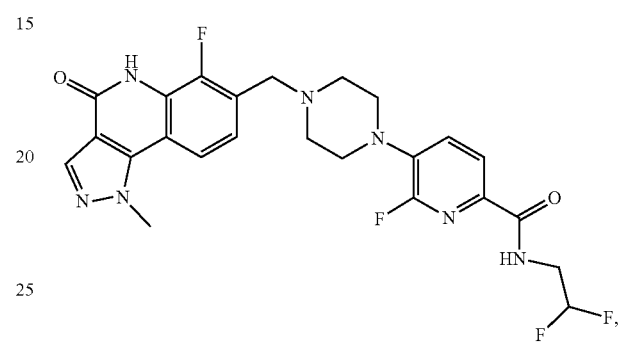
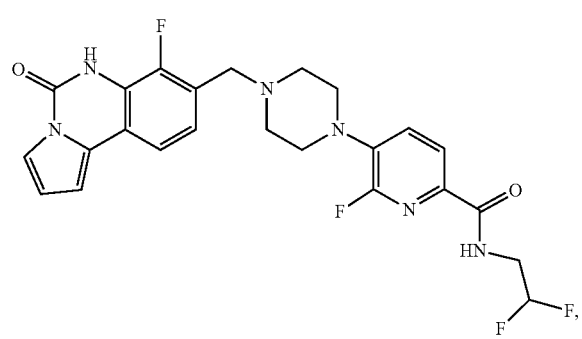
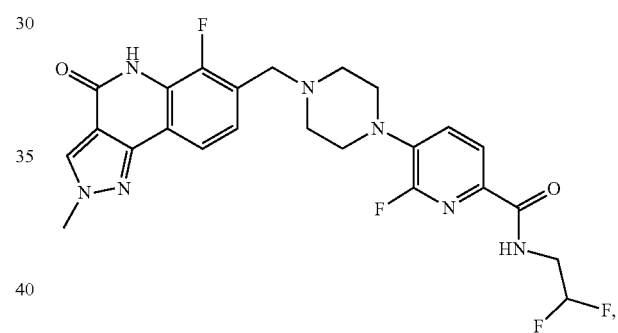
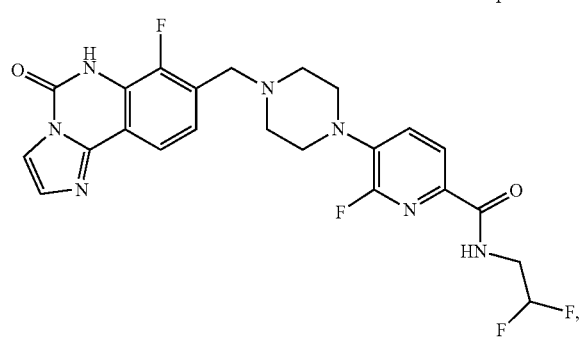
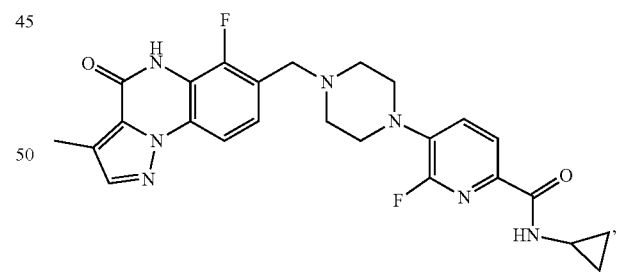
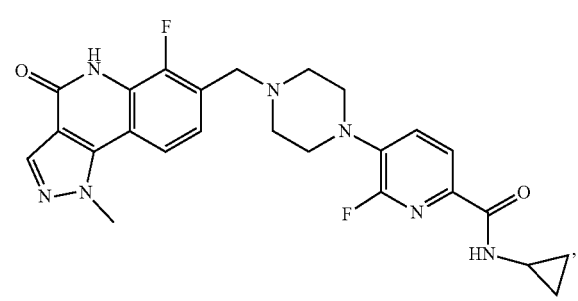
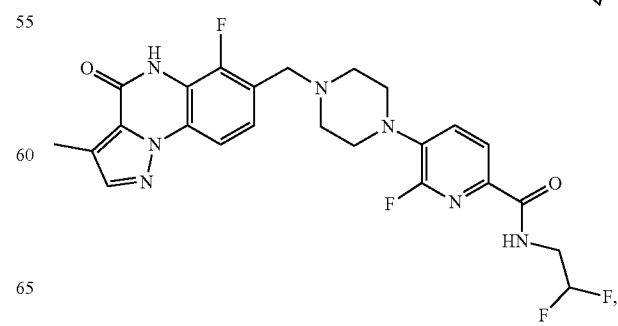

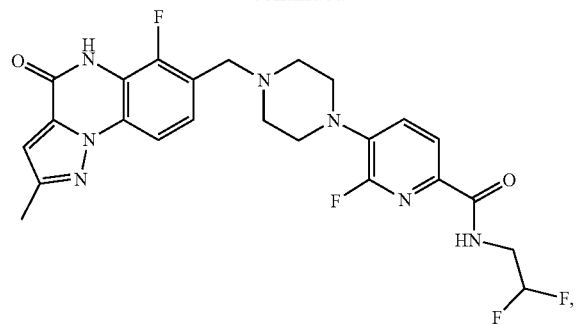
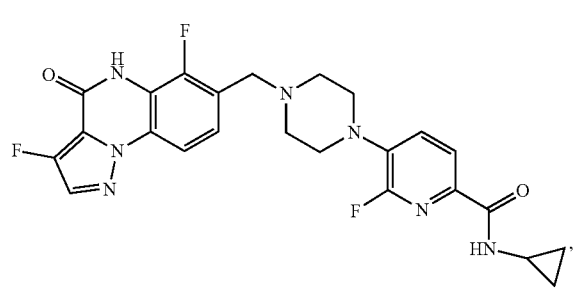
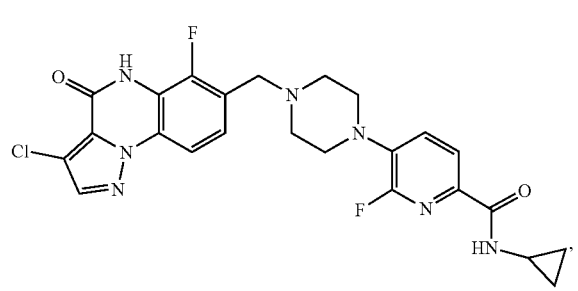
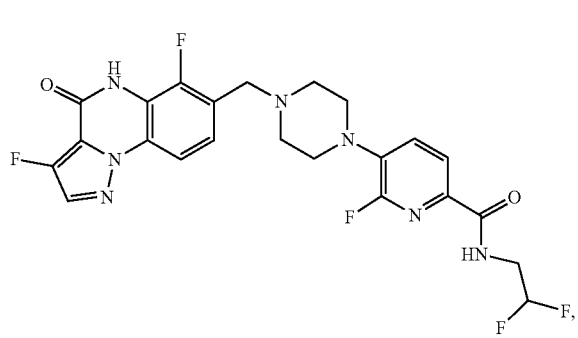
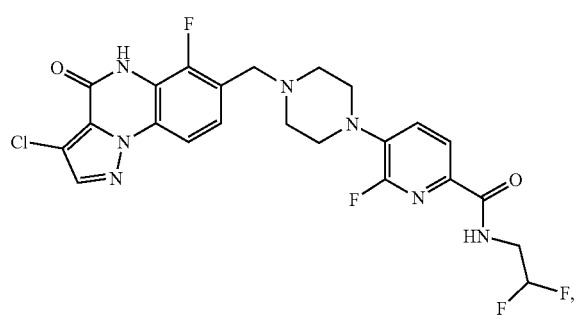
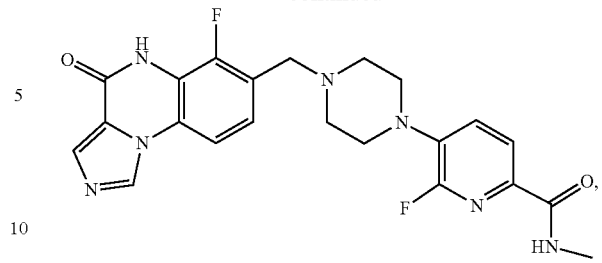
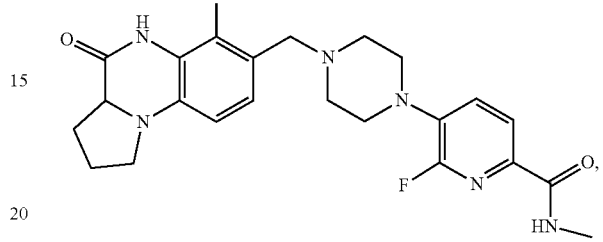
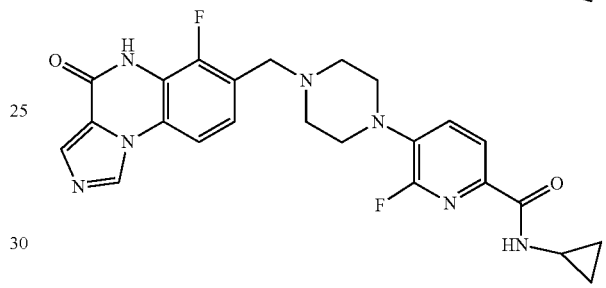
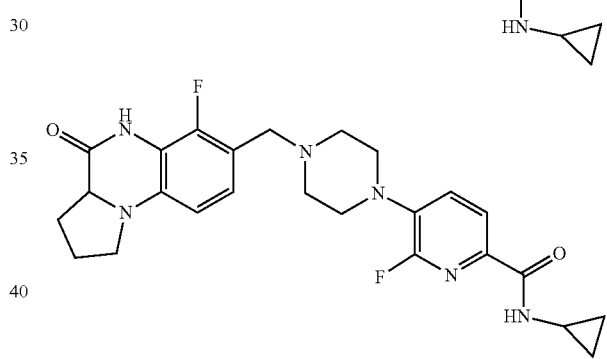
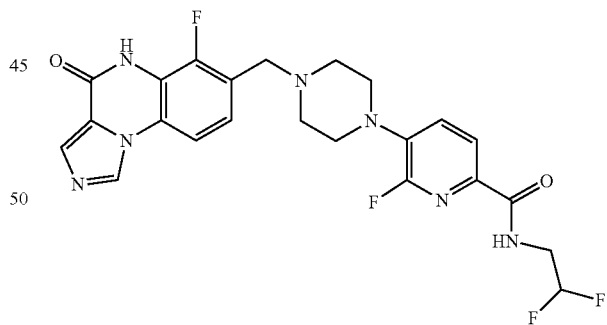
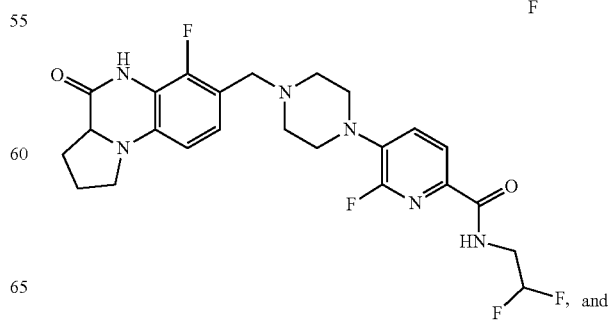

-continued

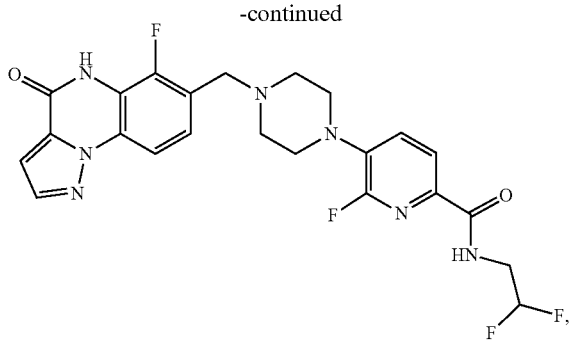

Further Forms of Compounds Disclosed Herein
Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine, and chloride, such as $^{2}H$, $^{3}H$, $^{13}C$, $^{14}C$, $^{14}N$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}\text{ alkyl})_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Method of Treatment

Disclosed herein are methods of treatment of a disease in which inhibition of PARP is beneficial, the method comprising administering a compound disclosed herein. Also disclosed herein are methods of treatment of a disease in which inhibition of PARP1 is beneficial, the method comprising administering a compound disclosed herein. In some embodiments, the disease is cancer. In some embodiments, the cancer is breast cancer, ovarian cancer, pancreatic cancer, prostate cancer, a hematological cancer, a gastrointestinal cancer such as gastric cancer and colorectal cancer, or lung cancer. In some embodiments, the cancer is breast cancer, ovarian cancer, pancreatic cancer, or prostate cancer. In some embodiment, the cancer is leukemia, colon cancer, glioblastoma, lymphoma, melanoma, or cervical cancer. In some embodiments, the cancer is bladder cancer, brain & CNS cancer, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

In some embodiments, the cancer is metastatic cancer. In some embodiments, the cancer has metastasized in the brain.

In some embodiments, the cancer comprises a BRCA1 and/or a BRCA2 mutation.

In some embodiments, the cancer comprising a BRCA1 and/or a BRCA2 mutation is bladder cancer, brain & CNS cancers, breast cancer, cervical cancer, colorectal cancer, esophagus cancer, Hodgkin lymphoma, non-Hodgkin lymphoma, kidney cancer, leukemia, lung cancer, melanoma, myeloma, oral cavity cancer, ovarian cancer, pancreatic cancer, prostate cancer, skin cancer, stomach cancer, thyroid cancer, or uterus cancer.

In some embodiments, the cancer is a cancer deficient in Flomologous Recombination (FIR) dependent DNA DSB repair activity. The FIR dependent DNA DSB repair pathway repairs double-strand breaks (DSBs) in DNA via homologous mechanisms to reform a continuous DNA helix. The components of the FIR dependent DNA DSB repair pathway include, but are not limited to, ATM (NM_000051), RAD51 (NM_002875), RAD51 L1 (NM_002877), RAD51 C (NM_002876), RAD51 L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11 A (NM_005590) and NBS1 (NM_002485). Other proteins involved in the FIR dependent DNA DSB repair pathway include regulatory factors such as EMSY. In some embodiments, the cancer which is deficient in FIR dependent DNA DSB repair comprises one or more cancer cells which have a reduced or abrogated ability to repair DNA DSBs through that pathway, relative to normal cells i.e., the activity of the FIR dependent DNA DSB repair pathway may be reduced or abolished in the one or more cancer cells.

In some embodiments, the activity of one or more components of the FIR dependent DNA DSB repair pathway is abolished in the one or more cancer cells of an individual having a cancer which is deficient in FIR dependent DNA DSB repair.

In some embodiments, the cancer cells have a BRCA1 and/or a BRCA2 deficient phenotype i.e., BRCA1 and/or BRCA2 activity is reduced or abolished in the cancer cells. Cancer cells with this phenotype may be deficient in BRCA1 and/or BRCA2, i.e., expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor. BRCA1 and BRCA2 are known tumor suppressors whose wild-type alleles are frequently lost in tumors of heterozygous carriers. Amplification of the EMSY gene, which encodes a BRCA2 binding factor, is also known to be associated with breast and ovarian cancer. Carriers of mutations in BRCA1 and/or BRCA2 are also at elevated risk of certain cancers, including breast cancer, ovarian cancer, pancreatic cancer, prostate cancer, a hematological cancer, gastrointestinal cancer, and lung cancer.

Also disclosed herein is a method of treating a cancer comprising a mutation in a gene conferring homologous repair deficiency in a subject in need thereof, the method comprising administering a compound disclosed herein, or a pharmaceutically acceptable salt, solvate, or stereoisomer thereof. In some embodiments, the mutation in a gene conferring homologous repair deficiency comprises ATM, BRCA1, BRCA2, BARD1, BRIP1, CDK12, CHEK1, CHEK2, FANCL, PALB2, RAD51B, RAD51C, RAD51D, or RAD54L, or any combinations thereof.

Also disclosed herein is a method for treating a cancer that is present in the brain, the method comprising administering a compound disclosed herein, or a pharmaceutically acceptable salt, solvate, or stereoisomer thereof.

In some embodiments, the cancer that is present in the brain arises from primary peripheral tumors that have metastasized to the brain. In some embodiments, the cancer that is present in the brain arises from primary brain tissues.

Also disclosed herein is a method for treating brain cancer, the method comprising administering a compound disclosed herein, or a pharmaceutically acceptable salt, solvate, or stereoisomer thereof.

In some embodiments, the brain cancer is a primary brain tumor that starts in the brain and tends to stay there.

In some embodiments, the brain cancer is a secondary brain tumor. These cancers start somewhere else in the body and travel to the brain. Lung, breast, kidney, colon, and skin cancers are among the most common cancers that spread to the brain.

In some embodiments, the compound disclosed herein, or a pharmaceutically acceptable salt, solvate, or stereoisomer thereof, is capable of penetrating the blood brain barrier (BBB). In some embodiments, the ratio of compound that penetrates the BBB is >0.1, wherein 1 is complete BBB penetration, and 0 is no penetration. In some embodiments, the ratio of compound that penetrates the BBB is >0.2. In some embodiments, the ratio of compound that penetrates the BBB is >0.3. In some embodiments, the ratio of compound that penetrates the BBB is measured using the rat $k_{p,uu}$ assay. In some embodiments, the compound has a ratio of >0.3 (i.e. from 0.3 to 1) as determined in the rat $k_{p,uu}$ assay.

Dosing

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of or risk factor for the disease being treated and is currently in remission, a pharmaceutical composition comprising a compound described herein, or a pharmaceutically acceptable salt thereof, to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage, or the frequency of administration, or both, is reduced, as a function of the symptoms, to a level at which the improved disease, disorder or condition is retained. In certain embodiments, however, the patient requires intermittent or daily treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage, or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{10}$ and the $ED_{90}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long-acting formulations are administered by implantation (for example subcutaneously or intramuscularly) or by intramuscular injection. Furthermore, in other embodiments, the drug is delivered in a targeted drug delivery system, for example, in a liposome coated with organ specific antibody. In such embodiments, the liposomes are targeted to and taken up selectively by the organ. In yet other embodiments, the compound as described herein is provided in the form of a rapid release formulation, in the form of an extended-release formulation, or in the form of an intermediate release formulation. In yet other embodiments, the compound described herein is administered topically.

Pharmaceutical Compositions/Formulations

The compounds described herein are administered to a subject in need thereof, either alone or in combination with pharmaceutically acceptable carriers, excipients, or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal, and topical routes of administration.

In another aspect, provided herein are pharmaceutical compositions comprising a compound described herein, or a pharmaceutically acceptable salt, solvate, or stereoisomer thereof, and at least one pharmaceutically acceptable excipient. Pharmaceutical compositions are formulated in a conventional manner using one or more pharmaceutically acceptable excipients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the pharmaceutically acceptable excipient is selected from carriers, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, and any combinations thereof.

The pharmaceutical compositions described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Pharmaceutical compositions including compounds described herein, or a pharmaceutically acceptable salt, solvate, or stereoisomer thereof are manufactured in a conventional manner, such as, by way of example only, by means of conventional mixing, dissolving, granulating, dragee-making, levigating, emulsifying, encapsulating, entrapping, or compression processes.

Pharmaceutical compositions for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical compositions that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

Pharmaceutical compositions for parental use are formulated as infusions or injections. In some embodiments, the pharmaceutical composition suitable for injection or infusion includes sterile aqueous solutions, or dispersions, or sterile powders comprising a compound described herein, or a pharmaceutically acceptable salt, solvate, or stereoisomer thereof. In some embodiments, the pharmaceutical composition comprises a liquid carrier. In some embodiments, the liquid carrier is a solvent or liquid dispersion medium comprising, for example, water, saline, ethanol, a polyol (for example, glycerol, propylene glycol, liquid polyethylene glycols, and the like), vegetable oils, nontoxic glyceryl esters, and any combinations thereof. In some embodiments, the pharmaceutical compositions further comprise a preservative to prevent growth of microorganisms.

Combination

Disclosed herein are methods of treating cancer using a compound disclosed herein, or a pharmaceutically acceptable salt, solvate, or stereoisomer thereof, in combination with an additional therapeutic agent.

In some embodiments, the additional therapeutic agent is an anticancer agent.

In some embodiments, the additional therapeutic agent is administered at the same time as the compound disclosed herein. In some embodiments, the additional therapeutic agent and the compound disclosed herein are administered sequentially. In some embodiments, the additional therapeutic agent is administered less frequently than the compound disclosed herein. In some embodiments, the additional therapeutic agent is administered more frequently than the compound disclosed herein. In some embodiments, the additional therapeutic agent is administered prior than the administration of the compound disclosed herein. In some embodiments, the additional therapeutic agent is administered after the administration of the compound disclosed herein.

EXAMPLES

Example 1

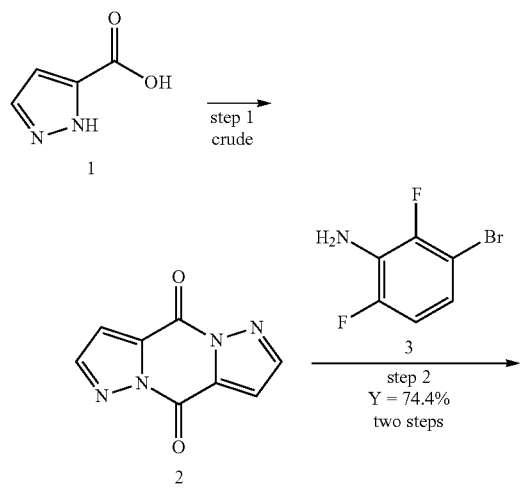

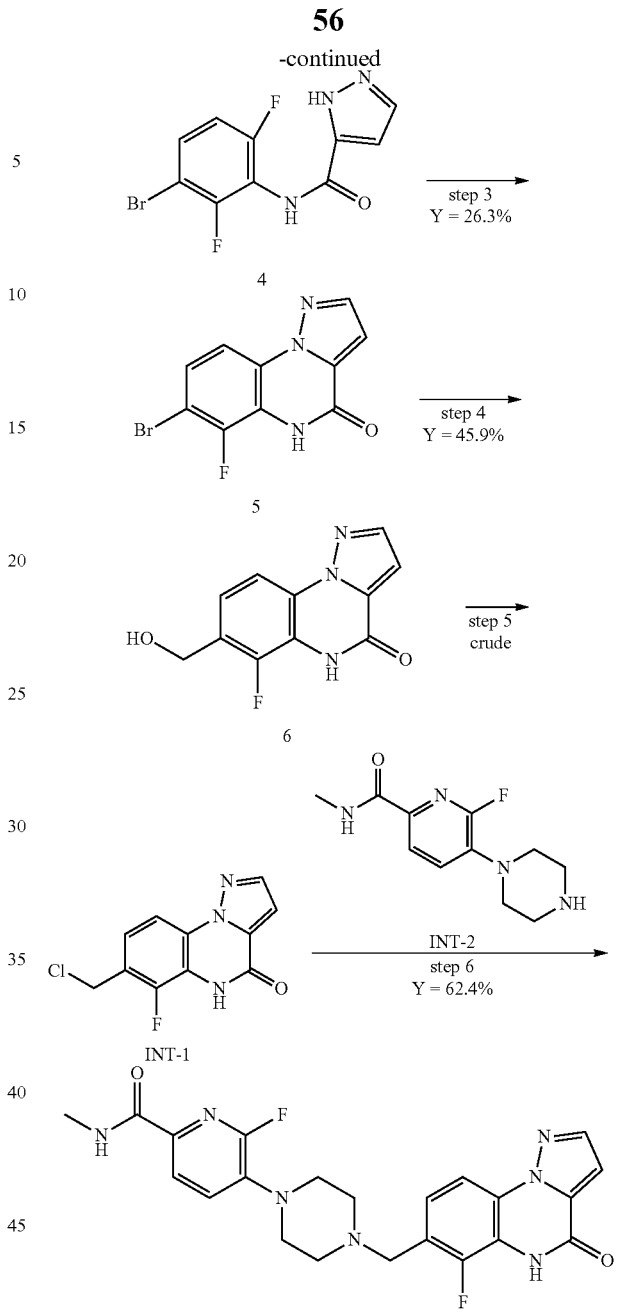

Example 1

Step 1 and Step 2: Preparation of N-(3-bromo-2,6-difluorophenyl)-2H-pyrazole-3-carboxamide A solution of 2H-pyrazole-3-carboxylic acid (3.00 g, 26.76 mmol, 1.00 equiv.) in $SOCl_2$ (30 mL) was stirred overnight at 90° C. under nitrogen atmosphere. The reaction was monitored by LCMS. The mixture was allowed to cool down to room temperature. The precipitated solids were collected by filtration and washed with toluene (3×50 mL). The resulting mixture was concentrated under reduced pressure. The crude product 1,6,7,12-tetraazatricyclo[7.3.0.0^{3,7}]dodeca-3,5,9,11-tetraene-2,8-dione (2.3 g) was used in the next step directly without further purification.

To a stirred solution of 1,6,7,12-tetraazatricyclo [7.3.0.0^{3,7}]dodeca-3,5,9,11-tetraene-2,8-dione (2.30 g, 12.22 mmol, 1.00 equiv.) and 3-bromo-2,6-difluoroaniline (5.09 g, 24.45 mmol, 2.00 equiv.) in THF (100 mL) was added NaHMDS (2 M, 30.56 mL, 61.12 mmol, 5.00 equiv.) dropwise at −10° C. The resulting mixture was stirred for additional 2 h at −10° C. The reaction was monitored by LCMS. The mixture was neutralized to pH 7 with $CH_3CO_2H$. The resulting mixture was concentrated under reduced pressure. The residue was dissolved in $H_2O$ (100 mL). The resulting mixture was extracted with EtOAc (3×100 mL). The combined organic layers were washed with brine (3×100 mL), dried over anhydrous $Na_2SO_4$, filtered and concentrated. The crude product was purified by silica gel column chromatography, eluted with PE/EA (0%-30% gradient in 30 min) to afford N-(3-bromo-2,6-difluorophenyl)-2H-pyrazole-3-carboxamide (6 g, 74.4%). LC-MS: (ES+H, m/z): [M+H]$^+$=301.9; $^1$H NMR (300 MHz, DMSO-$d_6$) δ 13.49 (s, 1H), 10.01 (s, 1H), 7.92 (d, J=2.4 Hz, 1H), 7.78-7.66 (m, 1H), 7.25 (td, J=9.1, 1.9 Hz, 1H), 6.77 (d, J=2.2 Hz, 1H).

Step 3: Preparation of
7-bromo-6-fluoro-5H-pyrazolo[1,5-a]44
uinoxaline-4-one

To a stirred solution of N-(3-bromo-2,6-difluorophenyl)-2H-pyrazole-3-carboxamide (5.80 g, 19.20 mmol, 1.00 equiv.) in DMA (2 mL) was added NaH (1.15 g, 28.80 mmol, 1.50 equiv., 60% in mineral oil) in portions at room temperature under nitrogen atmosphere. The resulting mixture was stirred overnight at 120° C. under nitrogen atmosphere. The reaction was monitored by LCMS. The mixture was allowed to cool down to room temperature. The reaction was quenched with water (50 mL) at 0° C. The resulting mixture was diluted with water (100 mL). The resulting mixture was extracted with EtOAc (3×300 mL). The combined organic layers were washed with brine (3×100 mL), dried over anhydrous $Na_2SO_4$, filtered and concentrated. The residue was dissolved in DMSO (20 mL) and purified by reverse flash chromatography (column: C18; mobile phase: MeOH in water (0.1% TFA), 50-70% gradient in 40 min; detector, UV 254 nm) to provide 7-bromo-6-fluoro-5H-pyrazolo[1,5-a]quinoxalin-4-one (1.5 g, 26.3%). LC-MS: (ES+H, m/z): [M+H]$^+$=281.9; $^1$H NMR (400 MHz, DMSO-$d_6$) δ 12.14 (s, 1H), 8.13 (s, 1H), 7.89 (d, J=8.9 Hz, 1H), 7.58 (t, J=7.7 Hz, 1H), 7.21 (s, 1H).

Step 4: Preparation of 6-fluoro-7-(hydroxymethyl)-5H-pyrazolo[1,5-a]quinoxalin-4-one To a stirred solution of 7-bromo-6-fluoro-5H-pyrazolo[1,5-a]quinoxalin-4-one (1.00 g, 3.54 mmol, 1.00 equiv.) and (tributylstannyl)methanol (1366 mg, 4.25 mmol, 1.20 equiv.) in dioxane (16 mL) was added 2nd Generation XPhos Precatalyst (279 mg, 0.35 mmol, 0.10 equiv.) at room temperature under nitrogen atmosphere. The resulting mixture was stirred for 2 h at 80° C. under nitrogen atmosphere. The reaction was monitored by LCMS. The resulting mixture was filtered, and then the filter cake was washed with DCM/MeOH (1:5) (3×150 mL). The filtrate was concentrated under reduced pressure. The residue was purified by silica gel column chromatography, eluted with $CH_2Cl_2$/MeOH (0%-7% gradient in 30 min) to afford 6-fluoro-7-(hydroxymethyl)-5H-pyrazolo[1,5-a]quinoxalin-4-one (400 mg, 45.9%). LC-MS: (ES+H, m/z): [M+H]$^+$=234.0; $^1$H NMR (300 MHz, DMSO-$d_6$) δ 11.95 (s, 1H), 8.10 (d, J=2.1 Hz, 1H), 7.93 (dd, J=8.5, 1.4 Hz, 1H), 7.38 (dd, J=8.5, 7.0 Hz, 1H), 7.19 (d, J=2.1 Hz, 1H), 5.42 (t, J=5.8 Hz, 1H), 4.63 (dd, J=5.8, 1.5 Hz, 2H).

Step 5: Preparation of 7-(chloromethyl)-6-fluoro-5H-pyrazolo[1,5-a]quinoxalin-4-one To a stirred solution of 6-fluoro-7-(hydroxymethyl)-5H-pyrazolo[1,5-a]quinoxalin-4-one (300 mg, 1.28 mmol, 1.00 equiv.) in DCM (8 mL) was added $SOCl_2$ (765 mg, 6.43 mmol, 5.00 equiv.) and DMF (5 mg, 0.07 mmol, 0.05 equiv.) dropwise at room temperature. The resulting mixture was stirred overnight at room temperature. The reaction was monitored by LCMS. The precipitated solids were collected by filtration and washed with DCM (3×30 mL). The crude product (7-(chloromethyl)-6-fluoro-5H-pyrazolo[1,5-a]quinoxalin-4-one) was used in the next step directly without further purification. LC-MS: (ES+H, m/z): [M+H]$^+$=252.0.

Step 6: Preparation of 6-fluoro-5-[4-({6-fluoro-4-oxo-5H-pyrazolo[1,5-a]quinoxalin-7-yl}methyl)piperazin-1-yl]-N-methylpyridine-2-carboxamide To a stirred mixture of 7-(chloromethyl)-6-fluoro-5H-pyrazolo[1,5-a]quinoxalin-4-one (180 mg, 0.71 mmol, 1.00 equiv.) and 6-fluoro-N-methyl-5-(piperazin-1-yl)pyridine-2-carboxamide (204 mg, 0.86 mmol, 1.20 equiv.) in MeCN (10 ml) were added KI (24 mg, 0.14 mmol, 0.20 equiv.) and DIEA (462 mg, 3.57 mmol, 5.00 equiv.) at room temperature. The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography ($CH_2Cl_2$/MeOH (0%-10% gradient in 30 min) to afford 6-fluoro-5-[4-({6-fluoro-4-oxo-5H-pyrazolo[1,5-a]quinoxalin-7-yl}methyl)piperazin-1-yl]-N-methylpyridine-2-carboxamide. The crude product was further purified by Prep-HPLC (Column: XBridge Shield RP18 OBD Column, 50*250 mm, 10 μm; Mobile Phase A: Water (0.05% $NH_3H_2O$), Mobile Phase B: MeCN; Flow rate: 25 mL/min; Gradient: 5% B to 40% B in 35 min, 40% B; Wave Length: 254/220 nm; RT1 (min): 30.5) to afford 6-fluoro-5-[4-({6-fluoro-4-oxo-5H-pyrazolo[1,5-a]quinoxalin-7-yl}methyl)piperazin-1-yl]-N-methylpyridine-2-carboxamide (204.4 mg, 62.4%). LC-MS: (ES+H, m/z): [M+H]$^+$=454.1; $^1$H NMR (300 MHz, DMSO-$d_6$) δ 11.98 (s, 1H), 8.40 (q, J=4.7 Hz, 1H), 8.10 (d, J=2.1 Hz, 1H), 7.94 (dd, J=8.5, 1.2 Hz, 1H), 7.84 (dd, J=8.1, 1.4 Hz, 1H), 7.55 (dd, J=10.6, 8.1 Hz, 1H) 7.34 (dd, J=8.5, 6.8 Hz, 1H), 7.19 (d, J=2.1 Hz, 1H), 3.69 (s, 2H), 3.17-3.14 (m, 4H), 2.77 (d, J=4.7 Hz, 3H), 2.65-2.57 (m, 4H). $^{19}$F NMR (282 MHz, DMSO-$d_6$) δ−72.57, −131.02.

The following examples were made using similar procedures shown for Example 1.

| Ex | Structure | NMR | LCMS (ESI) m/z |
|---|---|---|---|
| 2 | 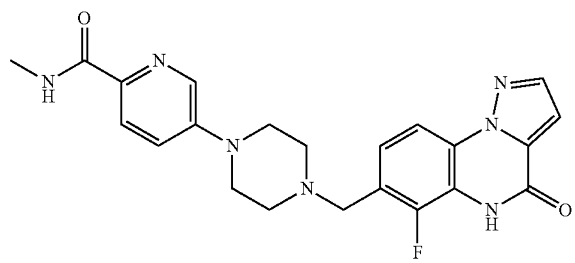 [SMILES: CNC(=O)c1ccc(N2CCN(Cc3ccc4c([nH]c(=O)c5ccnn54)c3F)CC2)cn1] | ¹H NMR (300 MHz, DMSO-d₆) δ 11.99 (s, 1H), 8.40 (d, J = 5.0 Hz, 1H), 8.27 (d, J = 2.8 Hz, 1H), 8.11 (d, J = 2.1 Hz, 1H), 7.96 (d, J = 8.6 Hz, 1H), 7.82 (d, J = 8.8 Hz, 1H), 7.42-7.32 (m, 2H), 7.20 (d, J = 2.1 Hz, 1H), 3.70 (s, 2H), 3.33-3.31 (m, 4H), 2.78 (d, J = 4.8 Hz, 3H), 2.62-2.56 (m, 4H). ¹⁹F NMR (282 MHz, DMSO-d₆) δ −131.08. | [M + H]⁺ = 436.15 |
| 3 | 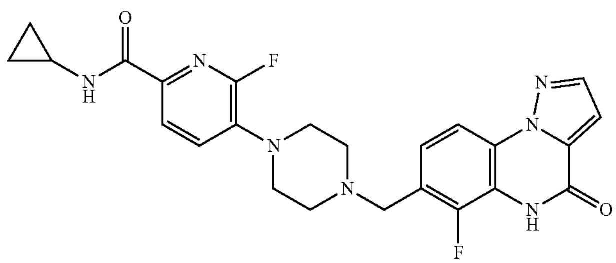 [SMILES: O=C(NC1CC1)c1ccc(N2CCN(Cc3ccc4c([nH]c(=O)c5ccnn54)c3F)CC2)c(F)n1] | ¹H NMR (300 MHz, DMSO-d₆) δ 11.98 (s, 1H), 8.35 (d, J = 4.9 Hz, 1H), 8.10 (d, J = 2.1 Hz, 1H), 7.94 (dd, J = 8.5, 1.2 Hz, 1H), 7.83 (dd, J = 8.1, 1.4 Hz, 1H), 7.55 (dd, J = 10.6, 8.1 Hz, 1H), 7.35 (dd, J = 8.5, 6.8 Hz, 1H), 7.19 (d, J = 2.1 Hz, 1H), 3.69 (s, 2H), 3.24-3.17 (m, 4H), 2.84-2.82 (m, 1H), 2.60-2.51 (m, 4H), 0.67-0.65 (m, 4H). ¹⁹F NMR (282 MHz, DMSO-d₆) δ −72.46, −131.02. | [M + H]⁺ = 480.10 |
| 4 | 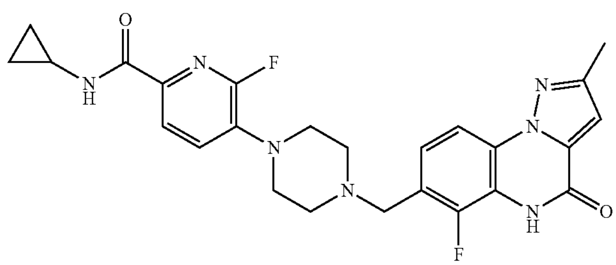 [SMILES: Cc1cc2c(=O)[nH]c3c(F)c(CN4CCN(c5ccc(C(=O)NC6CC6)nc5F)CC4)ccc3n2n1] | ¹H NMR (300 MHz, DMSO-d₆) δ 11.91 (s, 1H), 8.35 (d, J = 4.9 Hz, 1H), 7.85 (t, J = 8.7 Hz, 2H), 7.56 (dd, J = 10.6, 8.1 Hz, 1H), 7.32 (t, J = 7.8 Hz, 1H), 6.98 (s, 1H), 3.68 (s, 2H), 3.21-3.10 (m, 4H), 2.88-2.80 (m, 1H), 2.63-2.55 (m, 4H), 2.43 (s, 3H), 0.70-0.61 (m, 4H). ¹⁹F NMR (300 MHz, DMSO-d₆) δ −72.47, −131.29. | [M + H]⁺ = 494.20 |
| 5 | 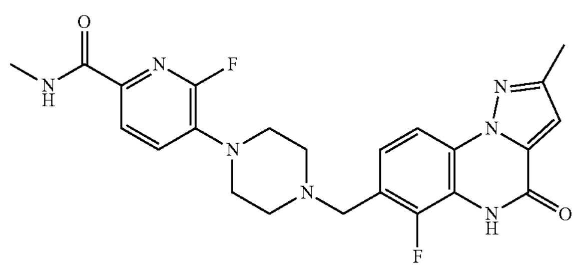 [SMILES: CNC(=O)c1ccc(N2CCN(Cc3ccc4c([nH]c(=O)c5cc(C)nn54)c3F)CC2)c(F)n1] | ¹H NMR (300 MHz, DMSO-d₆) δ 11.90 (s, 1H), 8.40 (d, J = 5.0 Hz, 1H), 7.90-7.79 (m, 2H), 7.55 (dd, J = 10.6, 8.1 Hz, 1H), 7.31 (t, J = 7.7 Hz, 1H), 6.98 (s, 1H), 3.68 (s, 2H), 3.21-3.12 (m, 4H), 2.76 (d, J = 4.7 Hz, 3H), 2.63-2.57 (m, 4H), 2.43 (s, 3H). ¹⁹F NMR (300 MHz, DMSO-d₆) δ −72.59, −131.30. | [M + H]⁺ = 468.15 |
| 8 | 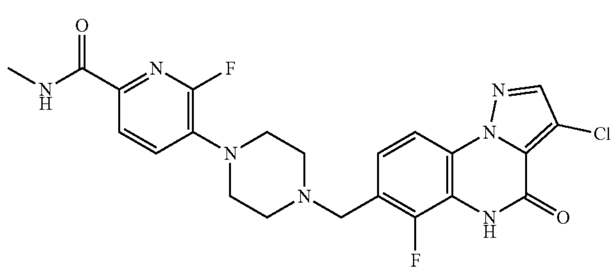 [SMILES: CNC(=O)c1ccc(N2CCN(Cc3ccc4c([nH]c(=O)c5c(Cl)cnn54)c3F)CC2)c(F)n1] | ¹H NMR (300 MHz, DMSO-d₆) δ 12.02 (s, 1H), 8.40 (d, J = 5.0 Hz, 1H), 8.25 (s, 1H), 8.00-7.77 (m, 2H), 7.56 (dd, J = 10.6, 8.1 Hz, 1H), 7.34 (t, J = 7.6 Hz, 1H), 3.69 (s, 2H), 3.17-3.12 (m, 4H), 2.76 (d, J = 4.7 Hz, 3H), 2.62-2.59 (m, 4H). ¹⁹F NMR (377 MHz, DMSO-d₆) δ −72.58, −130.86. | [M + H]⁺ = 488.2 |
| 12 | 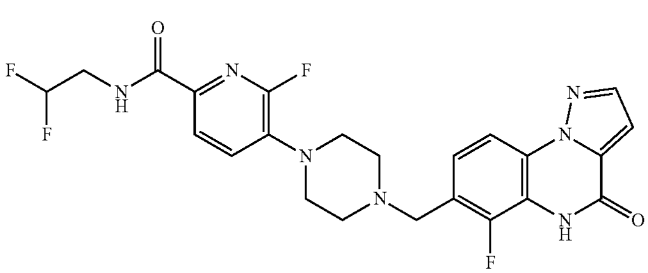 [SMILES: O=C(NCC(F)F)c1ccc(N2CCN(Cc3ccc4c([nH]c(=O)c5ccnn54)c3F)CC2)c(F)n1] | ¹H NMR (300 MHz, DMSO-d₆) δ 11.99 (s, 1H), 8.73 (t, J = 6.2 Hz, 1H), 8.11 (d, J = 2.1 Hz, 1H), 7.94 (dd, J = 8.5, 1.3 Hz, 1H), 7.88 (dd, J = 8.1, 1.5 Hz, 1H), 7.58 (dd, J = 10.6, 8.1 Hz, 1H), 7.35 (dd, J = 8.5, 6.8 Hz, 1H), 7.20 (d, J = 2.1 Hz, 1H), 6.11 (tt, J = 56.2, 4.2 Hz, 1H), 3.70-3.59 (m, 4H), 3.20-3.18 (m, 4H), 2.61-2.55 (m, 4H). ¹⁹F NMR (282 MHz, DMSO-d₆) δ −72.25, −121.97, −131.03. | [M + H]⁺ = 504.10 |

-continued

| Ex | Structure | NMR | LCMS (ESI) m/z |
|---|---|---|---|
| 13 | 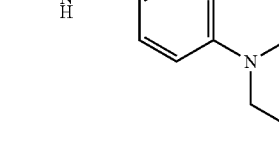 | $^1$H NMR (300 MHz, DMSO-d$_6$) δ 11.92 (s, 1H), 8.73 (t, J = 6.2 Hz, 1H), 7.90-7.82 (m, 2H), 7.63-7.52 (m, 1H), 7.37-7.27 (m, 1H), 6.98 (s, 1H), 6.32-5.88 (m, 1H), 3.79-3.54 (m, 4H), 3.23-3.15 (m, 4H), 2.65-2.56 (m, 4H), 2.43 (s, 3H). $^{19}$F NMR (282 MHz, DMSO-d$_6$) δ −72.25, 121.97, 131.29. | [M + H]$^+$ = 518.2 |
| 17 | 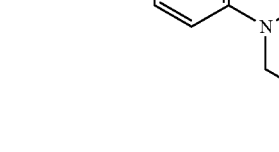 | $^1$H NMR (300 MHz, DMSO-d$_6$) δ 11.92 (s, 1H), 8.33 (t, J = 5.6 Hz, 1H), 7.91-7.80 (m, 2H), 7.57 (dd, J = 10.6, 8.1 Hz, 1H), 7.32 (dd, J = 8.5, 6.9 Hz, 1H), 6.98 (d, J = 0.6 Hz, 1H), 3.68 (s, 2H), 3.44-3.30 (m, 4H), 3.25 (s, 3H), 3.20-3.14 (m, 4H), 2.63-2.57 (m, 4H), 2.43 (s, 3H). $^{19}$F NMR (282 MHz, DMSO-d$_6$) δ −72.48, −131.30. | [M + H]$^+$ = 512.15 |
| 18 | 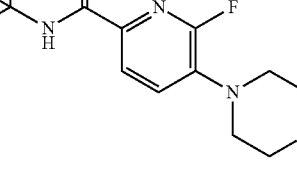 | $^1$H NMR (300 MHz, DMSO-d$_6$) δ 11.99 (s, 1H), 8.38 (s, 1H), 8.11 (d, J = 2.1 Hz, 1H), 7.95 (dd, J = 8.4, 1.3 Hz, 1H), 7.84 (dd, J = 8.0, 1.4 Hz, 1H), 7.56 (dd, J = 10.6, 8.1 Hz, 1H), 7.35 (dd, J = 8.5, 6.9 Hz, 1H), 7.20 (d, J = 2.1 Hz, 1H), 3.70 (s, 2H), 3.24-3.04 (m, 4H), 2.75-2.56 (m, 4H). $^{19}$F NMR (282 MHz, DMSO-d$_6$) δ −72.58, −131.02. | [M + H]$^+$ = 457.00 |
| 21 | 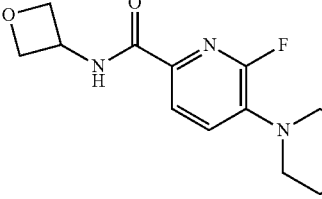 | $^1$H NMR (300 MHz, DMSO-d$_6$) δ 11.90 (s, 1H), 9.11 (d, J = 6.8 Hz, 1H), 7.85 (t, J = 8.7 Hz, 2H), 7.56 (dd, J = 10.6, 8.1 Hz, 1H), 7.36-7.27 (m, 1H), 6.98 (s, 1H), 4.99 (q, J = 7.2 Hz, 1H), 4.72-4.62 (m, 4H), 3.68 (s, 2H), 3.20-3.16 (m, 4H), 2.63-2.57 (m, 4H), 2.43 (s, 3H). $^{19}$F NMR (282 MHz, DMSO-d$_6$) δ −72.25, −131.28. | [M + H]$^+$ = 510.15 |
| 23 | 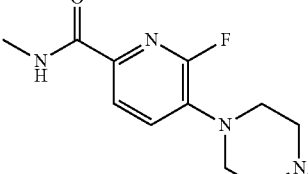 | $^1$H NMR (300 MHz, DMSO-d$_6$) δ 11.76 (s, 1H), 8.41 (q, J = 4.6 Hz, 1H), 7.93 (s, 1H), 7.89-7.82 (m, 2H), 7.56 (dd, J = 10.6, 8.1 Hz, 1H), 7.31 (dd, J = 8.5, 6.9 Hz, 1H), 3.68 (s, 2H), 3.21-3.12 (m, 4H), 2.76 (d, J = 4.7 Hz, 3H), 2.63-2.56 (m, 4H), 2.45 (s, 3H). $^{19}$F NMR (282 MHz, DMSO-d$_6$) δ −72.57, −131.21. | [M + H]$^+$ = 468.25 |

Example 6

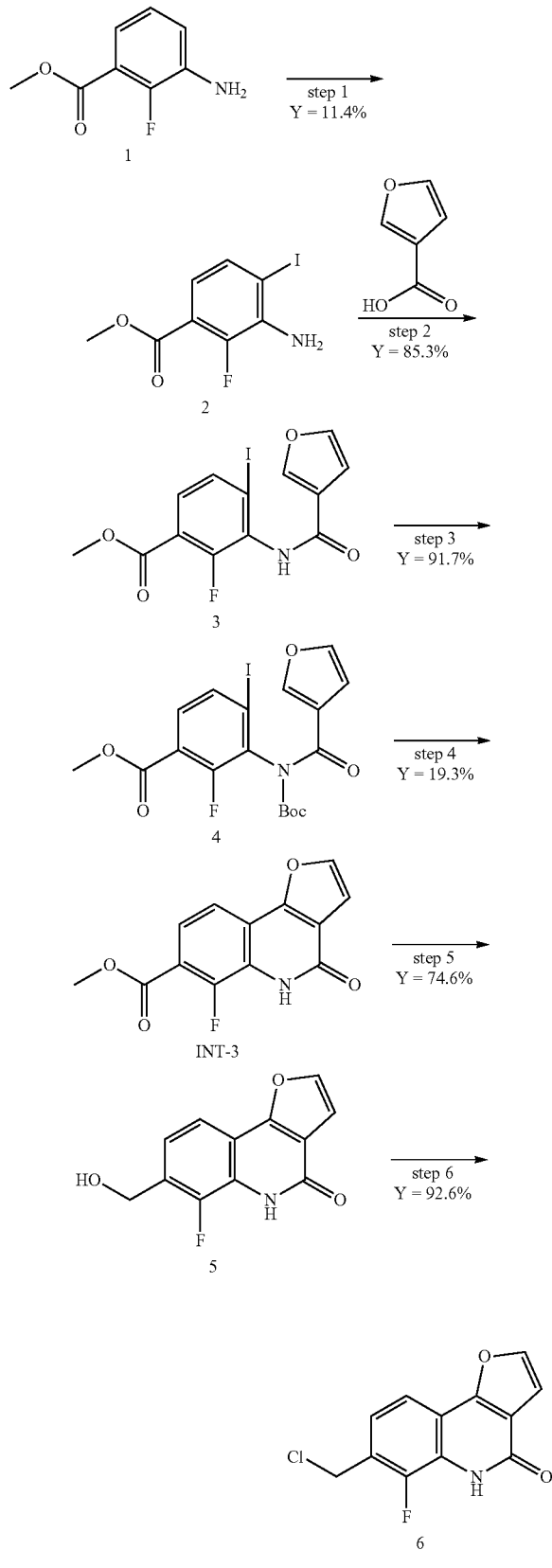

Example 6

Step 1: Preparation of methyl 3-amino-2-fluoro-4-iodobenzoate

A solution of methyl 3-amino-2-fluorobenzoate (20.00 g, 118.23 mmol, 0.00 equiv.) and NIS (23.94 g, 106.41 mmol, 0.90 equiv.) in AcOH (250 mL) was stirred for 1 h at room temperature under nitrogen atmosphere. The reaction was monitored by LCMS. The resulting mixture was concentrated under reduced pressure. The resulting mixture was diluted with water (200 mL). The resulting mixture was extracted with EtOAc (3×200 mL). The combined organic layers were washed with brine (2×100 mL), dried over anhydrous $Na_2SO_4$, filtered and concentrated. The residue was purified by reversed combi-flash chromatography (column: C18 gel; mobile phase, MeOH in Water (0.1% FA), 10% to 50% gradient in 10 min; detector, UV 254 nm) to afford methyl 3-amino-2-fluoro-4-iodobenzoate (4.00 g, 11.4%). LC-MS: (ES+H, m/z): [M+H]$^+$=295.80; $^1$H NMR (300 MHz, DMSO-d$_6$) δ 7.52 (dd, J=8.4, 1.5 Hz, 1H), 6.81 (dd, J=8.3, 6.7 Hz, 1H), 5.43 (s, 2H), 3.83 (s, 3H).

Step 2: Preparation of methyl 2-fluoro-3-(furan-3-amido)-4-iodobenzoate

Into a 250 mL round-bottom flask was added methyl 3-amino-2-fluoro-4-iodobenzoate (4.00 g, 13.55 mmol, 1.00 equiv.), 3-furoic acid (1.52 g, 13.55 mmol, 1.00 equiv.), T3P (43.14 g, 67.78 mmol, 5.00 equiv., 50% in EA) and DIEA (2.08 g, 16.10 mmol, 5.00 equiv.) at room temperature. The resulting mixture was stirred overnight at 100° C. under nitrogen atmosphere. The reaction was monitored by LCMS. The mixture was allowed to cool down to room temperature. The resulting mixture was diluted with water (100 mL). The resulting mixture was extracted with EtOAc (3×100 mL). The combined organic layers were washed with brine (2×100 mL), dried over anhydrous $Na_2SO_4$, filtered and concentrated. The residue was purified by silica gel column chromatography (PE/EA (0 to 20% gradient in 30 min)) to afford methyl 2-fluoro-3-(furan-3-amido)-4-iodobenzoate (4.50 g, 85.3%). LC-MS: (ES+H, m/z): [M+H]$^+$=389.85; $^1$H NMR (300 MHz, DMSO-d$_6$) δ 9.99 (s, 1H), 8.40 (s, 1H), 7.91 (dd, J=8.4, 1.2 Hz, 1H), 7.83 (t, J=1.7 Hz, 1H), 7.61 (dd, J=8.4, 7.0 Hz, 1H), 7.02-6.96 (m, 1H), 3.86 (s, 3H).

Step 3: Preparation of methyl 3-[N-(tert-butoxycarbonyl) furan-3-amido]-2-fluoro-4-iodobenzoate To a stirred mixture of methyl 2-fluoro-3-(furan-3-amido)-4-iodobenzoate (2.60 g, 6.68 mmol, 1.00 equiv.) and (Boc)₂O (2.92 g, 13.36 mmol, 2.00 equiv.) in DCE (50 mL) was added DMAP (0.82 g, 6.68 mmol, 1.00 equiv.) in portions at room temperature under nitrogen atmosphere. The resulting mixture was stirred overnight at room temperature under nitrogen atmosphere. The reaction was monitored by TLC (PE:EA=5:1, r=0.5). The resulting mixture was concentrated under reduced pressure. The residue was purified by silica gel column chromatography, eluted with PE/EA (0 to 20% gradient in 30 min) to afford methyl 3-[N-(tert-butoxycarbonyl) furan-3-amido]-2-fluoro-4-iodobenzoate (3.00 g, 91.7%).

Step 4: Preparation of methyl 6-fluoro-4-oxo-5H-furo[3,2-c]quinoline-7-carboxylate To a stirred solution of methyl 3-[N-(tert-butoxycarbonyl) furan-3-amido]-2-fluoro-4-iodobenzoate (3.00 g, 6.13 mmol, 1.00 equiv.) in DMF (30 mL) was added PCy₃ (344 mg, 1.22 mmol, 0.20 equiv.), Pd(OAc)₂ (275 mg, 1.22 mmol, 0.20 equiv.), and K₂CO₃ (1.69 g, 12.26 mmol, 2.00 equiv.) at room temperature under nitrogen atmosphere. The reaction mixture was irradiated with microwave radiation for 2 h at 120° C. The reaction was monitored by LCMS. The resulting mixture was diluted with water (50 mL) and extracted with EtOAc (3×100 mL). The combined organic layers were washed with brine (2×50 mL), dried over anhydrous Na₂SO₄, filtered and concentrated. The residue was purified by silica gel column chromatography (PE/EtOAc (0 to 20% gradient in 30 min)) to afford methyl 6-fluoro-4-oxo-5H-furo[3,2-c]quinoline-7-carboxylate (310 mg, 19.3%). LC-MS: (ES+H, m/z): [M+H+MeCN]⁺= 302.95.

Step 5: Preparation of 6-fluoro-7-(hydroxymethyl)-5H-furo[3,2-c]quinolin-4-one

To a stirred solution of methyl 6-fluoro-4-oxo-5H-furo[3,2-c]quinoline-7-carboxylate (150 mg, 0.57 mmol, 1.00 equiv.) in THF (10 mL) was added LiAlH₄ (0.46 mL, 1.14 mmol, 2.00 equiv., 2.5 M in THF) dropwise at 0° C. under nitrogen atmosphere. The resulting mixture was stirred for 2 h at 0° C. under nitrogen atmosphere. The reaction was monitored by LCMS. The reaction was quenched by the addition of HCl(aq.) (1 M, 1.2 mL) at 0° C. The residue was purified by silica gel column chromatography (CH₂Cl₂/MeOH (0 to 10% gradient in 30 min)) to afford 6-fluoro-7-(hydroxymethyl)-5H-furo[3,2-c]quinolin-4-one (100 mg, 74.6%). LC-MS: (ES+H, m/z): [M+H]⁺=233.95.

Step 6: Preparation of 7-(chloromethyl)-6-fluoro-5H-furo[3,2-c]quinolin-4-one

To a stirred solution of 6-fluoro-7-(hydroxymethyl)-5H-furo[3,2-c]quinolin-4-one (100 mg, 0.42 mmol, 1.00 equiv.) and DMF (2 mg, 0.03 mmol, 0.10 equiv.) in DCM (10 mL) was added SOCl₂ (0.24 mL, 3.30 mmol, 10.00 equiv.) dropwise at room temperature under nitrogen atmosphere. The resulting mixture was stirred for 2 h at room temperature under nitrogen atmosphere. The reaction was monitored by LCMS. The resulting mixture was concentrated under reduced pressure to afford 7-(chloromethyl)-6-fluoro-5H-furo[3,2-c]quinolin-4-one (100 mg, 92.6%). LC-MS: (ES+H, m/z): [M+H]⁺=252.00.

Step 7: Preparation of 6-fluoro-5-[4-({6-fluoro-4-oxo-5H-furo[3,2-c]quinolin-7-yl}methyl) piperazin-1-yl]-N-methylpyridine-2-carboxamide A solution of 6-fluoro-N-methyl-5-(piperazin-1-yl)pyridine-2-carboxamide (95 mg, 0.39 mmol, 1.00 equiv.) in MeCN (5 mL) was treated with DIEA (205 mg, 1.58 mmol, 4.00 equiv.) for 5 min at room temperature under nitrogen atmosphere followed by the addition of KI (7 mg, 0.04 mmol, 0.10 equiv.), 7-(chloromethyl)-6-fluoro-5H-furo[3,2-c]quinolin-4-one (100 mg, 0.39 mmol, 1.00 equiv.). The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by reverse flash chromatography (C18 gel; mobile phase, MeOH in Water (0.1% NH₃·H₂O), 10% to 50% gradient in 10 min; detector, UV 254 nm) to afford 6-fluoro-5-[4-({6-fluoro-4-oxo-5H-furo[3,2-c]quinolin-7-yl}methyl) piperazin-1-yl]-N-methylpyridine-2-carboxamide (43.2 mg, 23.8%). LC-MS: (ES+H, m/z): [M+H]⁺= 454.10; ¹H NMR (400 MHz, DMSO-d₆) δ 11.84-11.57 (m, 1H), 8.39 (q, J=4.7 Hz, 1H), 8.13 (d, J=2.1 Hz, 1H), 7.84 (dd, J=8.1, 1.4 Hz, 1H), 7.73 (d, J=8.1 Hz, 1H), 7.55 (dd, J=10.6, 8.1 Hz, 1H), 7.33 (dd, J=8.2, 6.2 Hz, 1H), 7.11 (d, J=2.1 Hz, 1H), 3.72 (s, 2H), 3.19-3.16 (m, 4H), 2.77 (d, J=4.7 Hz, 3H), 2.62-2.60 (m, 4H). ¹⁹F NMR (377 MHz, DMSO-d₆) δ−72.56, δ−132.19.

The following examples were made using similar procedures shown for Example 6.

| Ex | Structure | NMR | LCMS (ESI) m/z |
|---|---|---|---|
| 11 | 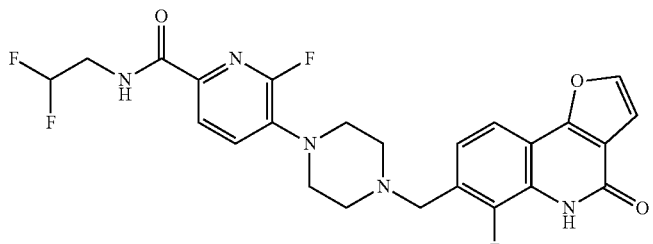 | ¹H NMR (400 MHz, DMSO-d₆) δ 11.72 (s, 1H), 8.71 (t, J = 6.3 Hz, 1H), 8.13 (d, J = 2.0 Hz, 1H), 7.87 (dd, J = 8.1, 1.4 Hz, 1H), 7.73 (d, J = 8.2 Hz, 1H), 7.58 (dd, J = 10.6, 8.1 Hz, 1H), 7.34 (dd, J = 8.2, 6.2 Hz, 1H), 7.11 (d, J = 2.0 Hz, 1H), 6.27-5.93 (m, 1H), 3.76-3.70 (m, 2H), 3.70-3.57 (m, 2H), 3.23-3.14 (m, 4H), 2.66-2.57 (m, 4H). ¹⁹F NMR (377 MHz, DMSO-d₆) δ −72.24, −121.96, −132.18. | [M + H]⁺ = 504.10 |

| Ex | Structure | NMR | LCMS (ESI) m/z |
|---|---|---|---|
| 14 | 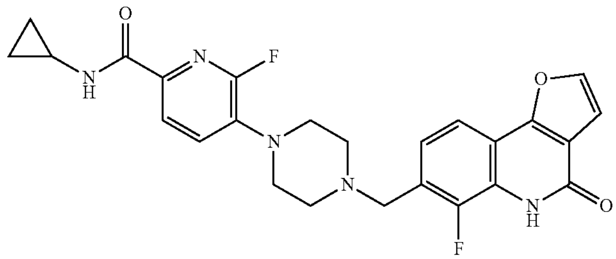 [SMILES: O=C(NC1CC1)c1ccc(N2CCN(Cc3ccc4c([nH]c(=O)c5ccoc54)c3F)CC2)c(F)n1] | $^1$H NMR (300 MHz, DMSO-d$_6$) δ 11.74 (s, 1H), 8.35 (d, J = 5.0 Hz, 1H), 8.14 (d, J = 2.0 Hz, 1H), 7.84 (dd, J = 8.0, 1.4 Hz, 1H), 7.74 (d, J = 8.2 Hz, 1H), 7.56 (dd, J = 10.6, 8.1 Hz, 1H), 7.34 (dd, J = 8.2, 6.2 Hz, 1H), 7.12 (d, J = 2.1 Hz, 1H), 3.73 (s, 2H), 3.20-3.15 (m, 4H), 2.90-2.80 (m, 1H), 2.65-2.60 (m, 4H), 0.69- 0.61 (m, 4H). $^{19}$F NMR (282 MHz, DMSO-d$_6$) δ −72.45, −132.16. | [M + H]$^+$ = 480.20 |
| 30 | 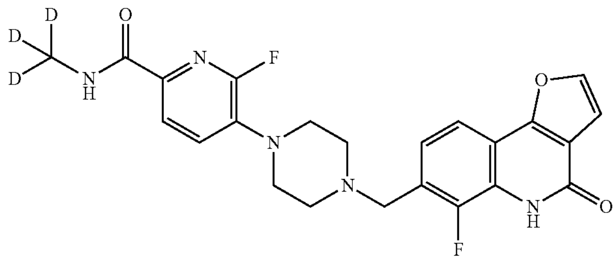 [SMILES: [2H]C([2H])([2H])NC(=O)c1ccc(N2CCN(Cc3ccc4c([nH]c(=O)c5ccoc54)c3F)CC2)c(F)n1] | $^1$H NMR (300 MHz, DMSO-d$_6$) δ 11.75 (s, 1H), 8.38 (s, 1H), 8.13 (d, J = 2.1 Hz, 1H), 7.84 (dd, J = 8.1, 1.5 Hz, 1H), 7.73 (d, J = 8.2 Hz, 1H), 7.56 (td, J = 10.6, 8.1 Hz, 1H), 7.34 (td, J = 8.2, 6.3 Hz, 1H), 7.11 (d, J = 2.0 Hz, 1H), 3.75 (s, 2H), 3.25-3.07 (m, 4H), 2.66-2.55 (m, 4H). $^{19}$F NMR (377 MHz, DMSO-d$_6$) δ −72.57, −132.17. | [M + H]$^+$ = 457.20 |
Example 7
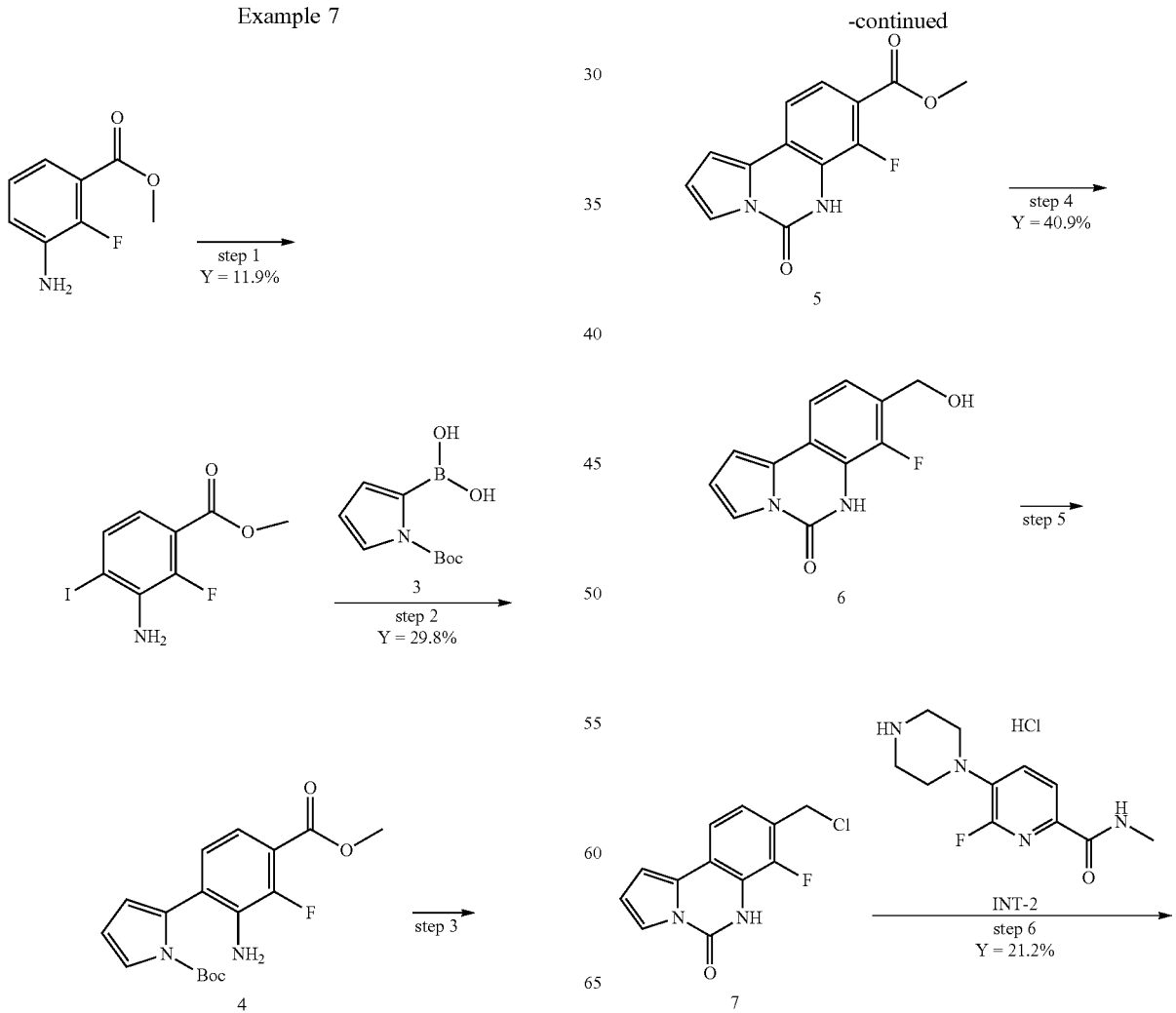

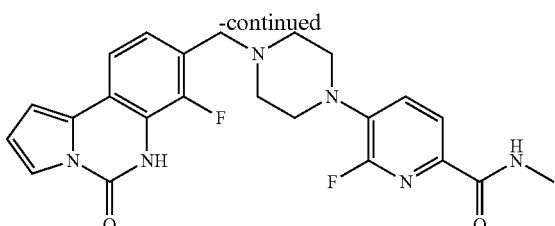

Example 7

Step 1: Preparation of methyl 3-amino-2-fluoro-4-iodobenzoate

A solution of methyl 3-amino-2-fluorobenzoate (10 g, 59.12 mmol, 1.00 equiv.) and NIS (12 g, 53.21 mmol, 0.90 equiv.) in AcOH (120 mL was stirred for 1 hr at room temperature under nitrogen atmosphere. The reaction was monitored by LCMS. The mixture was concentrated under reduced pressure. The residue was dissolved in ethyl acetate (10 mL) and poured into NaHCO$_3$ (100 mL)(aq.). The aqueous layer was extracted with EtOAc (3×100 mL) and the combined organic layers were concentrated under reduced pressure. The residue was purified by reversed-phase flash chromatography (C18; mobile phase: MeOH in Water (0.1% FA), 10% to 50% gradient in 10 min; detector, UV 254 nm) to afford methyl 3-amino-2-fluoro-4-iodobenzoate (2.1 g, 11.98%). LC-MS: (ES+H, m/z): [M+H]$^+$= 295.80; $^1$H NMR (400 MHz, DMSO-d$_6$) δ 7.52 (d, J=8.4, 1.3 Hz, 1H), 6.83-6.78 (m, J=8.3, 6.7 Hz, 1H), 5.44 (s, 2H), 3.82 (s, 3H).

Step 2: Preparation of tert-butyl 2-[2-amino-3-fluoro-4-(methoxycarbonyl)phenyl]pyrrole-1-carboxylate To a stirred solution of methyl 3-amino-2-fluoro-4-iodobenzoate (1 g, 3.39 mmol, 1.00 equiv.) and 1-(tert-butoxycarbonyl)pyrrol-2-ylboronic acid (1 g, 6.78 mmol, 2.00 equiv.) in 1,4-dioxane (120 mL) was added Pd(dppf)Cl$_2$·CH$_2$Cl$_2$ (276 mg, 0.34 mmol, 0.10 equiv.) and CsF (1 g, 6.78 mmol, 2.00 equiv.) at room temperature under nitrogen atmosphere. The resulting mixture was heated and stirred for 2 h at 100° C. under nitrogen atmosphere. The mixture was allowed to cool down to room temperature. The reaction was monitored by LCMS. The resulting mixture was concentrated under reduced pressure. The residue was purified by reversed-phase flash chromatography (C18; mobile phase: MeCN in Water (10 mmol/L NH$_4$HCO$_3$), 10% to 50% gradient in 10 min; detector, UV 254 nm) to provide tert-butyl 2-[2-amino-3-fluoro-4-(methoxycarbonyl)phenyl]pyrrole-1-carboxylate (420 mg, 29.84%). LC-MS: (ES+H, m/z): [M+H]$^+$=335.10.

Steps 3-4: Preparation of 7-fluoro-8-(hydroxymethyl)-6H-pyrrolo[1,2-c]quinazolin-5-one A solution of tert-butyl 2-[2-amino-3-fluoro-4-(methoxycarbonyl)phenyl]pyrrole-1-carboxylate (380 mg, 1.14 mmol, 1.00 equiv.) in HCl in 1,4-dioxane (5 mL) was stirred for 1 h at room temperature under nitrogen atmosphere. The reaction was monitored by LCMS. The resulting mixture was concentrated under reduced pressure to provide methyl 7-fluoro-5-oxo-6H-pyrrolo[1,2-c]quinazoline-8-carboxylate (370 mg, crude).

To the solution of methyl 7-fluoro-5-oxo-6H-pyrrolo[1,2-c]quinazoline-8-carboxylate (crude) in THF (10 mL) was added LiAlH$_4$ (0.9 mL, 2.28 mmol, 2.00 equiv., 2.5 M in THF) at 0° C. under nitrogen atmosphere. The mixture was stirred at 0° C. for 2 h. The reaction was monitored by LCMS. The mixture was poured into the water (50 mL) and extracted with EtOAc (3×10 mL). The combined organic layers were washed with brine (2×50 mL) and concentrated under reduced pressure. The residue was purified by silica gel column chromatography (PE/EA (3:1-1:1)) to afford 7-fluoro-8-(hydroxymethyl)-6H-pyrrolo[1,2-c]quinazolin-5-one (160 mg, 40.98%). LC-MS: (ES+H, m/z): [M+H]$^+$= 233.1; $^1$H NMR (300 MHz, DMSO-d$_6$) δ 11.54 (s, 1H), 7.74 (d, J=8.1 Hz, 1H), 7.64 (dd, J=3.1, 1.5 Hz, 1H), 7.30-7.23 (m, 1H), 7.04 (dd, J=3.6, 1.5 Hz, 1H), 6.72-6.68 (m, 1H), 5.37-5.32 (m, 1H), 4.60 (dd, J=5.7, 1.5 Hz, 2H).

Steps 5-6: Preparation of 6-fluoro-5-[4-({7-fluoro-5-oxo-6H-pyrrolo[1,2-c]quinazolin-8-yl}methyl)piperazin-1-yl]-N-methylpyridine-2-carboxamide To a stirred solution of 7-fluoro-8-(hydroxymethyl)-6H-pyrrolo[1,2-c]quinazolin-5-one (130 mg, 0.560 mmol, 1.00 equiv.) and 2 drops DMF in DCM (15 mL) was added SOCl$_2$ (333 mg, 2.8 mmol, 5.00 equiv.) in at 0° C. under nitrogen atmosphere. The resulting mixture was stirred for 1 h at room temperature under nitrogen atmosphere. The reaction was monitored by LCMS. The resulting mixture was concentrated under reduced pressure. The crude product mixture was used in the next step directly without further purification.

To a stirred solution of 8-(chloromethyl)-7-fluoro-6H-pyrrolo[1,2-c]quinazolin-5-one (130 mg, crude) and 6-fluoro-N-methyl-5-(piperazin-1-yl)pyridine-2-carboxamide (124 mg, 0.52 mmol, 1.00 equiv., HCl salt) in MeCN (15 mL) was added KI (9 mg, 0.1 mmol, 0.10 equiv.) and DIEA (201 mg, 1.56 mmol, 3.00 equiv.) at room temperature under nitrogen atmosphere. The resulting mixture was stirred for 1 h at 80° C. under nitrogen atmosphere. The reaction was monitored by LCMS. The resulting mixture was poured into water (35 mL) and extracted with EtOAc (3×50 mL). The combined organic layers were washed with brine (3×100 mL) and concentrated under reduced pressure. The crude product (200 mg) was purified by Prep-HPLC (Column: Xselect CSH C18 OBD Column 50*250 mm 10 m; Mobile Phase A: Water (0.1% NH$_4$HCO$_3$), Mobile Phase B: MeCN—Preparative; Flow rate: 100 mL/min; Gradient: 35% B to 55% B in 30 min, 52% B; Wave Length: 254/220 nm; RT1 (min): 27)) to afford 6-fluoro-5-[4-({7-fluoro-5-oxo-6H-pyrrolo[1,2-c]quinazolin-8-yl}methyl)piperazin-1-yl]-N-methylpyridine-2-carboxamide (50.2 mg, 21.2%). LC-MS: (ES+H, m/z): [M+H]$^+$=453.15; $^1$H NMR (300 MHz, DMSO-d$_6$) δ 11.57 (s, 1H), 8.40 (q, J=4.9 Hz, 1H), 7.84 (dd, J=8.1, 1.5 Hz, 1H), 7.74 (d, J=8.1 Hz, 1H), 7.65 (dd, J=3.1, 1.5 Hz, 1H), 7.61-7.52 (m, 1H), 7.28-7.18 (m, 1H), 7.06 (dd, J=3.6, 1.5 Hz, 1H), 6.75-6.67 (m, 1H), 3.67 (s, 2H), 3.25-3.11 (m, 4H), 2.76 (d, J=4.7 Hz, 3H), 2.66-2.56 (m, 4H). $^{19}$F NMR (282 MHz, DMSO-d$_6$) δ−72.56, −133.82.

Example 9

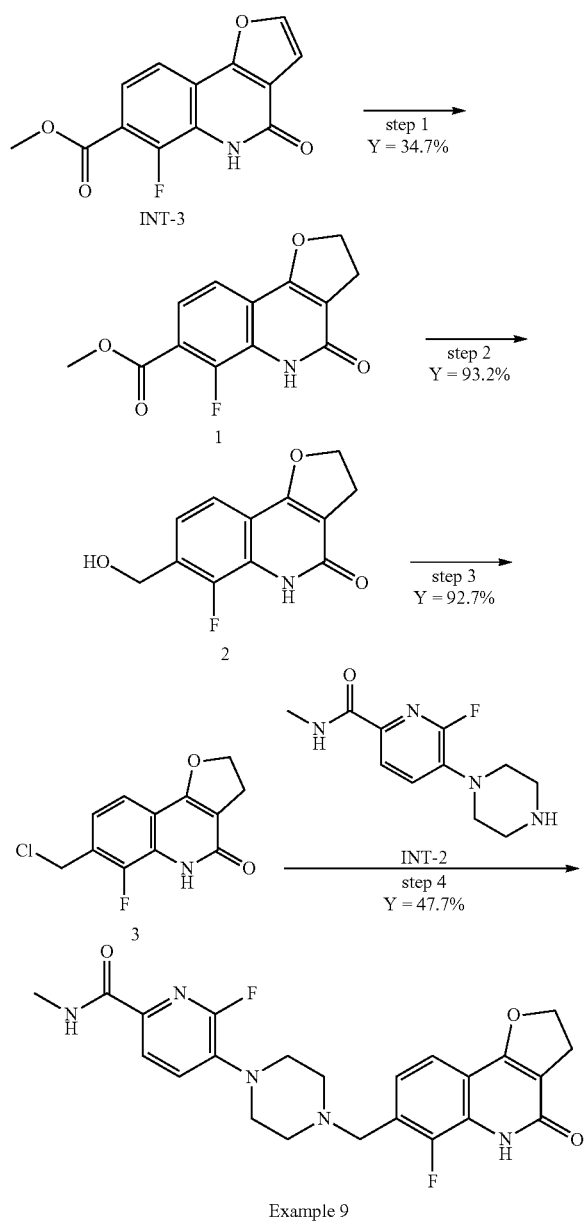

Example 9

Step 1: Preparation of methyl 6-fluoro-4-oxo-2H,3H,5H-furo[3,2-c]quinoline-7-carboxylate To a stirred solution of methyl 6-fluoro-4-oxo-5H-furo[3,2-c]quinoline-7-carboxylate (200 mg, 0.76 mmol, 1.00 equiv.) in $CF_3CH_2OH$ (50 mL) was added Pd/C (163 mg, 10%) at room temperature. The resulting mixture was stirred overnight at room temperature under a hydrogen atmosphere. The reaction was monitored by LCMS. Upon completion, the resulting mixture was filtered and then the filter cake was washed with $CH_2Cl_2$/MeOH (10:1, 3×50 mL). The filtrate was concentrated under reduced pressure and then purified by silica gel column chromatography, eluted with $CH_2Cl_2$/MeOH (0 to 10% gradient in 30 min) to afford methyl 6-fluoro-4-oxo-2H,3H,5H-furo[3,2-c]quinoline-7-carboxylate (70 mg, 34.7%). LC-MS: (ES+H, m/z): [M+H]$^+$=263.95; $^1$H NMR (300 MHz, DMSO-d$_6$) δ 11.68 (s, 1H), 7.58 (dd, J=8.4, 6.1 Hz, 1H), 7.49 (d, J=8.5 Hz, 1H), 4.85 (t, J=9.4 Hz, 2H), 3.89 (s, 3H), 3.10 (t, J=9.4 Hz, 2H). $^{19}$F NMR (377 MHz, DMSO-d$_6$) δ−124.45.

Step 2: Preparation of 6-fluoro-7-(hydroxymethyl)-2H,3H,5H-furo[3,2-c]quinolin-4-one To a stirred solution of methyl 6-fluoro-4-oxo-2H,3H,5H-furo[3,2-c]quinoline-7-carboxylate (60 mg, 0.22 mmol, 1.00 equiv.) in THF (5 mL) was added LiAlH$_4$ (0.18 mL, 0.45 mmol, 2.00 equiv., 2.5 M in THF) dropwise at 0° C. under nitrogen atmosphere. The resulting mixture was stirred for 2 h at 0° C. under nitrogen atmosphere. The reaction was monitored by LCMS. The reaction was quenched by the addition of HCl (aq.) (1 M, 0.5 mL) at 0° C. The resulting mixture was concentrated under reduced pressure. The residue was purified by silica gel column chromatography, eluted with $CH_2Cl_2$/MeOH (0 to 10% gradient in 30 min) to afford 6-fluoro-7-(hydroxymethyl)-2H,3H,5H-furo[3,2-c]quinolin-4-one (50 mg, 93.2%). LC-MS: (ES+H, in/z): [M+H]$^+$=236.0.

Step 3: Preparation of 7-(chloromethyl)-6-fluoro-2H,3H,5H-furo[3,2-c]quinolin-4-one To a stirred solution of 6-fluoro-7-(hydroxymethyl)-2H,3H,5H-furo[3,2-c]quinolin-4-one (50 mg, 0.21 mmol, 1.00 equiv.) and DMF (2 mg, 0.02 mmol, 0.10 equiv.) in DCM (10 mL) was added SOCl$_2$ (253 mg, 2.13 mmol, 10.00 equiv.) dropwise at room temperature under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)-6-fluoro-2H,3H,5H-furo[3,2-c]quinolin-4-one (50 mg, 92.7%). LC-MS: (ES+H, m/z): [M+H]$^+$=254.0.

Step 4: Preparation of 6-fluoro-5-[4-({6-fluoro-4-oxo-2H,3H,5H-furo[3,2-c]quinolin-7-yl}methyl)piperazin-1-yl]-N-methylpyridine-2-carboxamide A solution of 6-fluoro-N-methyl-5-(piperazin-1-yl)pyridine-2-carboxamide (47 mg, 0.19 mmol, 1.00 equiv) in MeCN (3 mL) was treated with DIEA (102 mg, 0.78 mmol, 4.00 equiv.) for 5 min at room temperature under nitrogen atmosphere followed by the addition of KI (3 mg, 0.02 mmol, 0.10 equiv.) and 7-(chloromethyl)-6-fluoro-2H,3H,5H-furo[3,2-c]quinolin-4-one (50 mg, 0.19 mmol, 1.00 equiv.). The resulting mixture was stirred for 2 h at 80° C. under nitrogen atmosphere. The reaction was monitored by LCMS. The mixture was allowed to cool down to room temperature. The resulting mixture was concentrated under reduced pressure. The residue was purified by silica gel column chromatography ($CH_2Cl_2$/MeOH (0 to 10% gradient in 30 min)) to afford 6-fluoro-5-[4-({6-fluoro-4-oxo-2H,3H,5H-furo[3,2-c]quinolin-7-yl}methyl) piperazin-1-yl]-N-methylpyridine-2-carboxamide (44.0 mg, 47.7%). LC-MS: (ES+H, m/z): [M+H]$^+$=456.05; $^1$H NMR (300 MHz, DMSO-d$_6$) δ 11.42 (s, 1H), 8.40 (d, J=5.0 Hz, 1H), 7.84 (dd, J=8.1, 1.4 Hz, 1H), 7.55 (dd, J=10.6, 8.1 Hz, 1H), 7.41 (d J=8.2 Hz, 1H), 7.27-7.19 (m, 1H), 4.82 (t, J=9.3 Hz, 2H), 3.69 (s, 2H), 3.18-3.15 (m, 4H), 3.07 (t J=9.3 Hz, 2H), 2.76 (d, J=4.8 Hz, 3H), 2.60-2.57 (5, 4H). $^{19}$F NMR (377 MHz, DMSO-d$_6$) δ−72.57, −132.99.

The following examples were made using similar procedures shown for Example 9.

| Ex | Structure | NMR | LCMS (ESI) m/z |
|---|---|---|---|
| 15 | 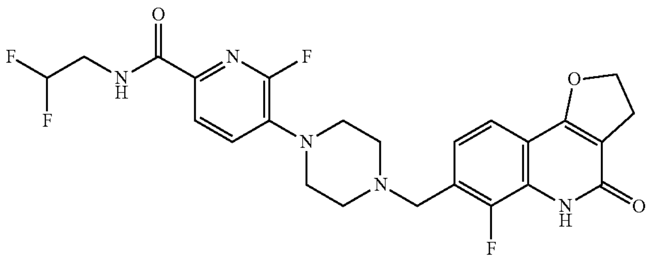 [SMILES: O=C(NCC(F)F)c1ccc(N2CCN(Cc3ccc4c5c(c(=O)[nH]c4c3F)CCO5)CC2)c(F)n1] | ¹H NMR (300 MHz, DMSO-d₆) δ 11.41 (s, 1H), 8.72 (t, J = 6.3 Hz, 1H), 7.88 (dd, J = 8.0, 1.4 Hz, 1H), 7.58 (dd, J = 10.5, 8.1 Hz, 1H), 7.41 (d, J = 8.2 Hz, 1H), 7.23 (dd, J = 8.2, 6.2 Hz, 1H), 6.11 (tt, J = 56.2, 4.2 Hz, 1H), 4.82 (t, J = 9.2 Hz, 2H), 3.76 - 3.57 (m, 4H), 3.26-3.14 (m, 4H), 3.08 (t, J = 9.3 Hz, 2H), 2.66-2.55 (m, 4H). ¹⁹F NMR (282 MHz, DMSO-d₆) δ −72.24, −121.96, −132.99. | [M + H]⁺ = 506.20 |
| 16 | 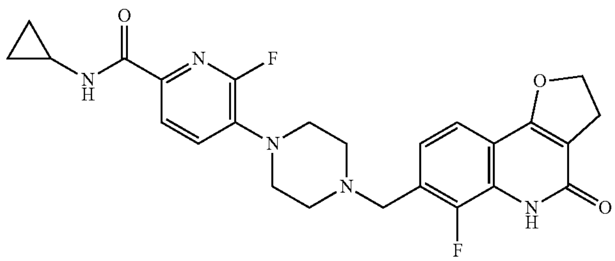 [SMILES: O=C(NC1CC1)c1ccc(N2CCN(Cc3ccc4c5c(c(=O)[nH]c4c3F)CCO5)CC2)c(F)n1] | ¹H NMR (300 MHz, DMSO-d₆) δ 11.41 (s, 1H), 8.35 (d, J = 4.9 Hz, 1H), 7.84 (dd, J = 8.1, 1.4 Hz, 1H), 7.55 (dd, J = 10.6, 8.1 Hz, 1H), 7.41 (d, J = 8.2 Hz, 1H), 7.23 (dd, J = 8.2, 6.2Hz, 1H), 4.82 (t, J = 9.3 Hz, 2H), 3.70 (s, 2H), 3.20-3.13 (m, 4H), 3.07 (t, J = 9.3 Hz, 2H), 2.88-2.80 (m, 1H), 2.61-2.57 (m, 4H), 0.71-0.59 (m, 4H). ¹⁹F NMR (282 MHz, DMSO-d₆) δ −72.45, −132.98. | [M + H]⁺ = 482.20 |
| 22 | 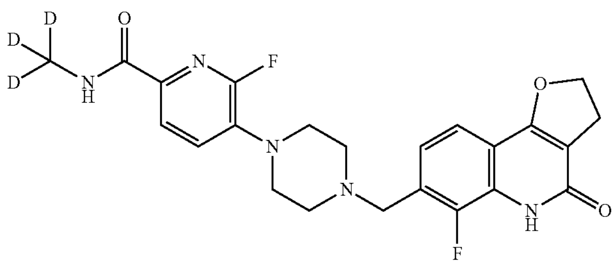 [SMILES: [2H]C([2H])([2H])NC(=O)c1ccc(N2CCN(Cc3ccc4c5c(c(=O)[nH]c4c3F)CCO5)CC2)c(F)n1] | ¹H NMR (400 MHz, DMSO-d₆) δ 11.42 (s, 1H), 8.38 (s, 1H), 7.84 (dd, J = 8.1, 1.4 Hz, 1H), 7.55 (dd, J = 10.6, 8.1 Hz, 1H), 7.41 (d, J = 8.2 Hz, 1H), 7.23 (dd, J = 8.2, 6.1 Hz, 1H), 4.82 (t, J = 9.3 Hz, 2H), 3.80-3.61 (m, 2H), 3.24-3.12 (m, 4H), 3.07 (t, J = 9.3 Hz, 2H), 2.62-2.54 (m, 4H). ¹⁹F NMR (377 MHz, DMSO-d₆) δ −72.57, −132.98. | [M + H]⁺ = 459.20 |
| 24 | 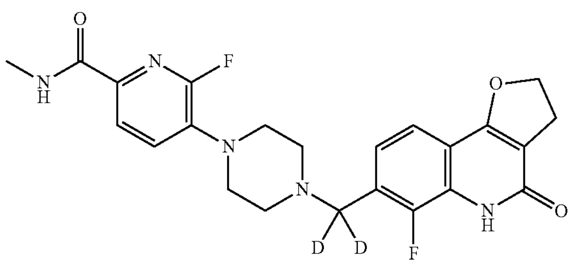 [SMILES: [2H]C([2H])(c1ccc2c3c(c(=O)[nH]c2c1F)CCO3)N1CCN(c2ccc(C(=O)NC)nc2F)CC1] | ¹H NMR (400 MHz, DMSO-d₆) δ 11.42 (s, 1H), 8.40 (q, J = 4.7 Hz, 1H), 7.83 (dd, J = 8.1, 1.4 Hz, 1H), 7.55 (dd, J = 10.6, 8.1 Hz, 1H), 7.40 (d, J = 8.2 Hz, 1H), 7.22 (dd, J = 8.2, 6.2 Hz, 1H), 4.82 (t, J = 9.3 Hz, 2H), 3.19-3.12 (m, 4H), 3.07 (t, J = 9.3 Hz, 2H), 2.76 (d, J = 4.8 Hz, 3H), 2.62-2.55 (m, 4H). ¹⁹F NMR (376 MHz, DMSO-d₆) δ −72.56, −133.02. | [M + H]⁺ = 458.20 |
| 26 | 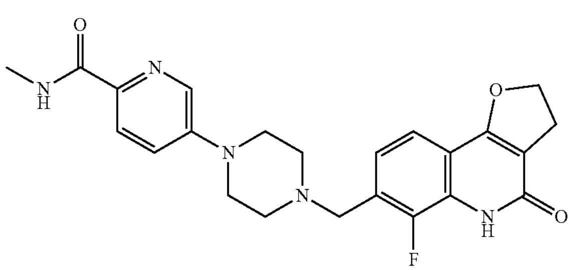 [SMILES: CNC(=O)c1ccc(N2CCN(Cc3ccc4c5c(c(=O)[nH]c4c3F)CCO5)CC2)cn1] | ¹H NMR (400 MHz, DMSO-d₆) δ 11.42 (s, 1H), 8.39 (q, J = 4.8 Hz, 1H), 8.25 (d, J = 2.9 Hz, 1H), 7.82 (d, J = 8.8 Hz, 1H), 7.44-7.34 (m, 2H), 7.23 (dd, J = 8.2, 6.1 Hz, 1H), 4.82 (t, J = 9.3 Hz, 2H), 3.69 (s, 2H), 3.36-3.29 (m, 4H), 3.07 (t, J = 9.3 Hz, 2H), 2.78 (d, J = 4.8 Hz, 3H), 2.57 (t, J = 5.0 Hz, 4H). ¹⁹F NMR (376 MHz, DMSO-d₆) δ −132.96. | [M + H]⁺ = 438.20 |
| 27 | 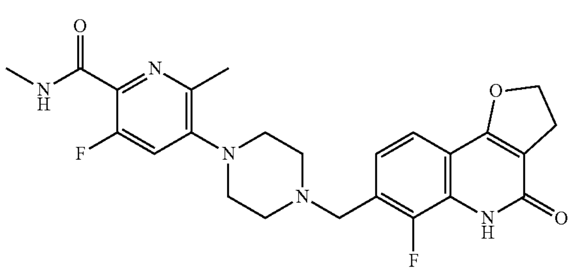 [SMILES: CNC(=O)c1nc(C)c(N2CCN(Cc3ccc4c5c(c(=O)[nH]c4c3F)CCO5)CC2)cc1F] | ¹H NMR (300 MHz, DMSO-d₆): δ 11.42 (s, 1H), 8.34 (q, J = 4.7 Hz, 1H), 7.41 (d, J = 8.2 Hz, 1H), 7.31 (d, J = 12.6 Hz, 1H), 7.23 (dd, J = 8.2, 6.1 Hz, 1H), 4.82 (t, J = 9.3 Hz, 2H), 3.71 (s, 2H), 3.07 (t, J = 9.3 Hz, 2H), 2.98-2.93 (m, 4H), 2.76 (d, J = 4.9 Hz, 3H), 2.64-2.56 (m, 4H), 2.42 (s, 3H). ¹⁹F NMR (377 MHz, DMSO-d₆) δ −123.74, δ −133.00. | [M + H]⁺ = 470.10 |

| Ex | Structure | NMR | LCMS (ESI) m/z |
|---|---|---|---|
| 29 | 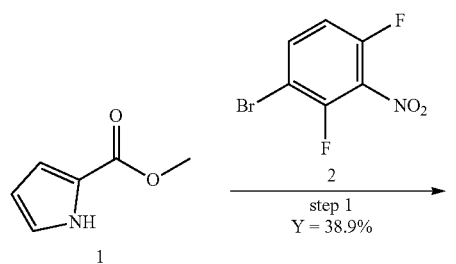 | $^1$H NMR (300 MHz, DMSO-$d_6$) δ 11.42 (s, 1H), 8.42 (d, J = 5.0 Hz, 1H), 7.78 (d, J = 8.2 Hz, 1H), 7.50-7.40 (m, 2H), 7.23 (dd, J = 8.2, 6.2 Hz, 1H), 4.82 (t, J = 9.3 Hz, 2H), 3.71 (s, 2H), 3.07 (t, J = 9.3 Hz, 2H), 2.98-2.90 (m, 4H), 2.80 (d, J = 4.8 Hz, 3H), 2.64-2.55 (m, 4H), 2.48 (s, 3H). $^{19}$F NMR (282 MHz, DMSO-$d_6$) δ −133.00 | [M + H]$^+$ = 452.25 |

Example 10

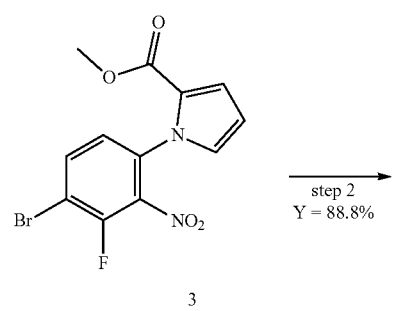

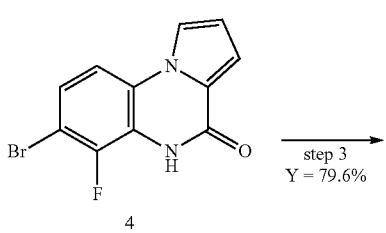

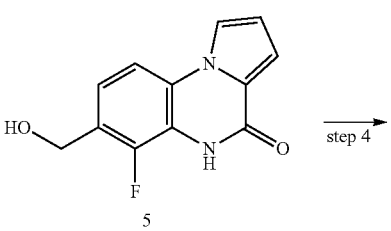

Example 10

Step 1: Preparation of methyl 1-(4-bromo-3-fluoro-2-nitrophenyl)pyrrole-2-carboxylate To a stirred solution of methyl pyrrole-2-carboxylate (1.1 g, 8.791 mmol, 1 equiv.) and $K_2CO_3$ (2.4 g, 17.58 mmol, 2 equiv.) in DMF (10 mL) was added 1-bromo-2,4-difluoro-3-nitrobenzene (3.1 g, 13.19 mmol, 1.50 equiv.) at room temperature under nitrogen atmosphere. The resulting mixture was stirred for 2 h at 100° C. under nitrogen atmosphere. The reaction was monitored by LCMS. The resulting mixture was poured into water (100 mL) and extracted with EtOAc (3×100 mL). The combined organic layers were washed with brine (3×150 mL), dried over anhydrous $Na_2SO_4$, filtered, and concentrated. The residue was purified by silica gel column chromatography (PE/EtOAc (0-30%)) to afford the crude product. The crude product (2.5 g) was further purified by Prep-HPLC (Column: YMC-Triart Prep C18-S, 100*250 mm, S-100 μm, 120 A; Mobile Phase A: Water (0.05% NH$_3$·H$_2$O+12.5 mmol/L NH$_4$HCO$_3$), Mobile Phase B: MeOH; Flow rate:120 mL/min; Gradient: 45% B to 85% B in 40 min, 74% B; Wave Length: 254/220 nm; RT1 (min): 27) to afford methyl 1-(4-bromo-3-fluoro-2-nitrophenyl)pyrrole-2-carboxylate (1.2 g, 38.8%). LC-MS: (ES+H, m/z): [M+H]$^+$=342.95; $^1$H NMR (300 MHz, DMSO-$d_6$) δ 8.19 (dd, J=8.7, 7.3 Hz, 1H), 7.53 (dd, J=8.7, 1.8 Hz, 1H), 7.32 (dd, J=2.8, 1.7 Hz, 1H), 7.07 (dd, J=3.9, 1.7 Hz, 1H), 6.42 (dd, J=3.9, 2.8 Hz, 1H), 3.64 (s, 3H).

Step 2: Preparation of 7-bromo-6-fluoro-5H-pyrrolo[1,2-a]quinoxalin-4-one

To a stirred solution of methyl 1-(4-bromo-3-fluoro-2-nitrophenyl)pyrrole-2-carboxylate (1.1 g, 3.206 mmol, 1 equiv.) and Fe (895 mg, 16.030 mmol, 5 equiv.) in AcOH (10 mL) at room temperature under nitrogen atmosphere. The resulting mixture was stirred for 2 h at 75° C. under nitrogen atmosphere. The reaction was monitored by LCMS. The resulting mixture was filtered, and then the filter cake was washed with MeOH (2×10 mL). The filtrate was concentrated under reduced pressure. The residue was purified by silica gel column chromatography, eluted with $CH_2Cl_2$/MeOH (1:0-10:1) to afford 7-bromo-6-fluoro-5H-pyrrolo[1,2-a]quinoxalin-4-one (800 mg, 88.7%). LC-MS: (ES+H, m/z): $[M+H]^+$=281.0; $^1H$ NMR (300 MHz, DMSO-$d_6$) δ 11.47 (s, 1H), 8.22 (dd, J=2.9, 1.5 Hz, 1H), 7.89 (dd, J=9.0, 1.7 Hz, 1H), 7.50 (dd, J=8.9, 6.8 Hz, 1H), 7.11 (dd, J=3.9, 1.4 Hz, 1H), 6.74 (dd, J=3.9, 2.8 Hz, 1H).

Step 3: Preparation of 6-fluoro-7-(hydroxymethyl)-5H-pyrrolo[1,2-a]quinoxalin-4-one To a stirred solution of 7-bromo-6-fluoro-5H-pyrrolo[1,2-a]quinoxalin-4-one (380 mg, 1.352 mmol, 1.00 equiv.) and (tributylstannyl)methanol (521 mg, 1.622 mmol, 1.2 equiv.) in 1,4-dioxane (10 mL) was added XPhos Pd G2 (53 mg, 0.068 mmol, 0.05 equiv.) at room temperature under nitrogen atmosphere. The resulting mixture was stirred for 16 h at 80° C. under nitrogen atmosphere. The reaction was monitored by LCMS. The resulting mixture was concentrated under reduced pressure. The residue was purified by silica gel column chromatography ($CH_2Cl_2$/MeOH (0-20%)) to afford 6-fluoro-7-(hydroxymethyl)-5H-pyrrolo[1,2-a]quinoxalin-4-one (250 mg, 79.6%). LC-MS: (ES+H, m/z): $[M+H]^+$=233.3; $^1H$ NMR (300 MHz, DMSO-$d_6$) δ 11.28 (s, 1H), 8.18 (dd, J=2.9, 1.5 Hz, 1H), 7.88 (dd, J=8.6, 1.4 Hz, 1H), 7.26 (dd, J=8.5, 7.2 Hz, 1H), 7.08 (dd, J=3.9, 1.4 Hz, 1H), 6.71 (dd, J=3.9, 2.8 Hz, 1H), 5.36 (t, J=5.8 Hz, 1H), 4.61-4.59 (m, 2H).

Steps 4-5: Preparation of 6-fluoro-5-[4-({6-fluoro-4-oxo-5H-pyrrolo[1,2-a]quinoxalin-7-yl}methyl)piperazin-1-yl]-N-methylpyridine-2-carboxamide To a stirred solution of 6-fluoro-7-(hydroxymethyl)-5H-pyrrolo[1,2-a]quinoxalin-4-one (150 mg, 0.646 mmol, 1 equiv.) and $SOCl_2$ (384 mg, 3.230 mmol, 5 equiv.) in DCM (5 mL) was added DMF (9 mg, 0.129 mmol, 0.2 equiv.) at room temperature under nitrogen atmosphere. The resulting mixture was stirred for 1 h at room temperature under nitrogen atmosphere. The reaction was monitored by LCMS. The resulting mixture was concentrated under reduced pressure. The crude resulting mixture was used in the next step directly without further purification. To a stirred solution of 7-(chloromethyl)-6-fluoro-5H-pyrrolo[1,2-a]quinoxalin-4-one (crude) and 6-fluoro-N-methyl-5-(piperazin-1-yl)pyridine-2-carboxamide (142 mg, 0.598 mmol, 1 equiv., 1 eq HCl salt) in MeCN (5 mL) were added KI (10 mg, 0.060 mmol, 0.1 equiv.) and DIEA (232 mg, 1.794 mmol, 3 equiv.) at room temperature under nitrogen atmosphere. The resulting mixture was stirred for 5 h at 80° C. under nitrogen atmosphere. The reaction was monitored by LCMS. The resulting mixture poured into water (20 mL), was extracted with $CH_2Cl_2$ (3×50 mL). The combined organic layers were washed with brine (2×10 mL), dried over anhydrous $Na_2SO_4$, filtered and concentrated. The crude product (300 mg) was purified by Prep-HPLC (Column: Xselect CSH C18 OBD Column 30*150 mm 5 μm; Mobile Phase A: Water (0.1% formic acid), Mobile Phase B: MeOH—Preparative; Flow rate: 60 mL/min; Gradient: 21% B to 36% B in 9 min, 36% B; Wave Length: 254/220 nm; RT1 (min): 8.12) to afford 6-fluoro-5-[4-({6-fluoro-4-oxo-5H-pyrrolo[1,2-a]quinoxalin-7-yl}methyl)piperazin-1-yl]-N-methylpyridine-2-carboxamide (54 mg, 19.3%). LC-MS: (ES+H, m/z): $[M+H]^+$=453.15; $^1H$ NMR (300 MHz, DMSO-$d_6$) δ 11.30 (s, 1H), 8.40 (q, J=4.9 Hz, 1H), 8.20 (dd, J=2.9, 1.5 Hz, 1H), 7.96-7.77 (m, 2H), 7.56 (dd, J=10.6, 8.1 Hz, 1H), 7.23 (t, J=8.1 Hz, 1H), 7.09 (dd, J=3.9, 1.4 Hz, 1H), 6.72 (t, J=3.6 Hz, 1H), 3.66 (s, 2H), 3.17 (t, J=4.6 Hz, 4H), 2.76 (d, J=4.8 Hz, 3H), 2.60 (t, J=4.8 Hz, 4H). $^{19}F$ NMR (282 MHz, DMSO-$d_6$) δ −72.56, −131.51.

Examples 19 and 20

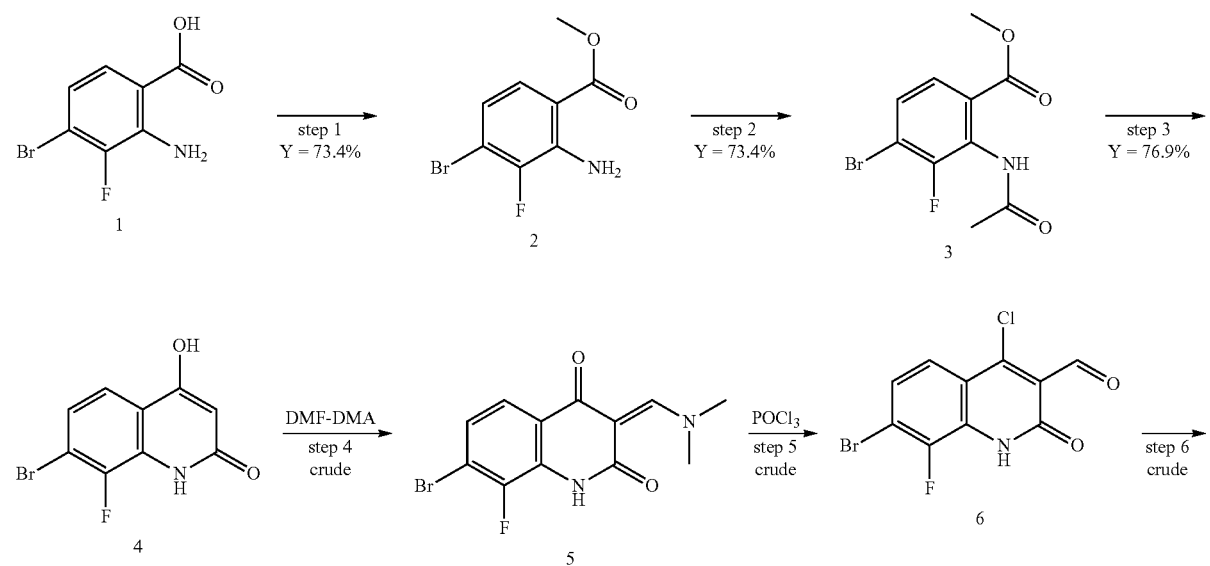

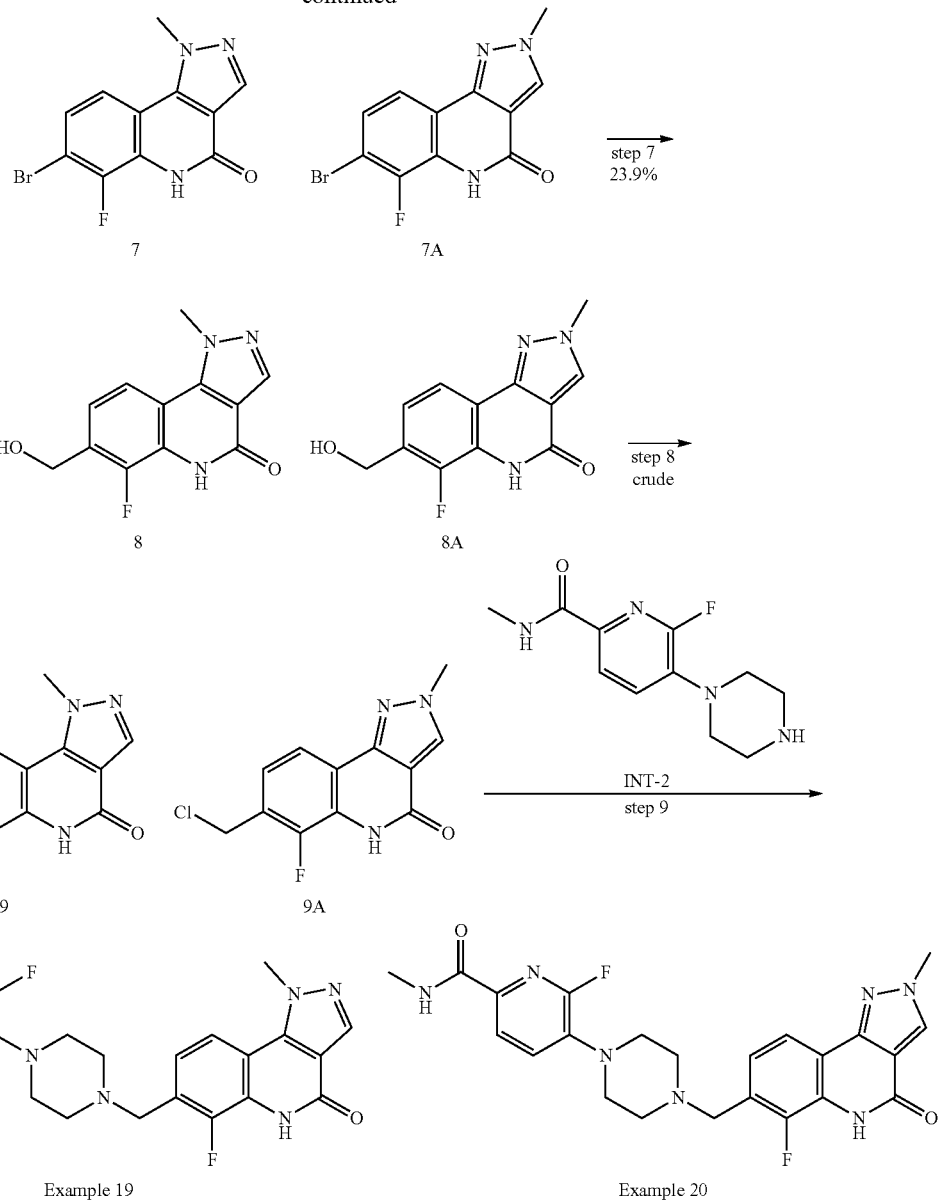

Step 1: Preparation of methyl 2-amino-4-bromo-3-fluorobenzoate

A solution of 2-amino-4-bromo-3-fluorobenzoic acid (15.00 g, 64.09 mmol, 1.00 equiv.) in DMF (200 mL) was treated with DIEA (33.14 g, 256.38 mmol, 4.00 equiv.) for 5 min at room temperature under nitrogen atmosphere followed by the addition of CH₃I (16.38 g, 115.37 mmol, 1.80 equiv.) dropwise at room temperature. The resulting mixture was stirred overnight at room temperature under nitrogen atmosphere. The reaction was monitored by LCMS. The resulting mixture was diluted with EtOAc (1000 mL). The resulting mixture was washed with brine (3×500 mL) and the combined organic layers were concentrated under reduced pressure. The residue was purified by silica gel column chromatography (PE/EtOAc (0% to 20% gradient in 30 min)) to afford methyl 2-amino-4-bromo-3-fluorobenzoate (12.30 g, 73.4%). LC-MS: (ES+H, m/z): [M+H]$^+$=247.8/249.8; $^1$H NMR (300 MHz, DMSO-d$_6$) δ 7.48 (dd, J=8.8, 1.7 Hz, 1H), 6.93-6.22 (m, 3H), 3.82 (s, 3H).

Step 2: Preparation of methyl 4-bromo-2-acetamido-3-fluorobenzoate

To a stirred solution of methyl 2-amino-4-bromo-3-fluorobenzoate (12.30 g, 49.58 mmol, 1.00 equiv.) in MeCN (100 mL) was added acetyl chloride (5.84 g, 74.38 mmol, 1.50 equiv.) dropwise at 0° C. under nitrogen atmosphere. The resulting mixture was stirred for 3 h at room temperature under nitrogen atmosphere. The reaction was monitored by LCMS. The resulting mixture was concentrated under reduced pressure. The residue was purified by trituration with EtOAc (50 mL) to afford methyl 4-bromo-2-acetamido-3-fluorobenzoate (9.00 g, 73.4%). LC-MS: (ES+H, m/z): [M+H]$^+$=290.2/290.2.

Step 3: Preparation of 7-bromo-8-fluoro-4-hydroxy-1H-quinolin-2-one

To a stirred solution of methyl 4-bromo-2-acetamido-3-fluorobenzoate (9.50 g, 32.74 mmol, 1.00 equiv.) in THF (80 mL) was added LiHMDS (81 mL, 1.0 mol/L, 2.50 equiv.) dropwise at −78° C. under nitrogen atmosphere. The resulting mixture was stirred for 2 h at 0° C. under nitrogen atmosphere. The reaction was monitored by LCMS. The reaction was quenched with water at 0° C. The resulting mixture was diluted with water (100 mL) and acidified to pH 5 with HCl (aq.). The precipitated solids were collected by filtration and washed with water (2×50 mL) to provide 7-bromo-8-fluoro-4-hydroxy-1H-quinolin-2-one (6.40 g, 76.9%). LC-MS: (ES+H, m/z): [M+H]$^+$=257.8/259.8.

Step 4: Preparation of (3Z)-7-bromo-3-[(dimethylamino)methylidene]-8-fluoro-1H-quinoline-2,4-dione A solution of 7-bromo-8-fluoro-4-hydroxy-1H-quinolin-2-one (6.50 g, 25.18 mmol, 1.00 equiv.) and DMF-DMA (4.50 g, 37.78 mmol, 1.50 equiv.) in toluene (70 mL) was stirred for 24 h at 80° C. under nitrogen atmosphere. The reaction was monitored by LCMS. The mixture was allowed to cool down to room temperature. The precipitated solids were collected by filtration, washed with toluene (3×30 mL), and dried under vacuum to afford (3Z)-7-bromo-3-[(dimethylamino)methylidene]-8-fluoro-1H-quinoline-2,4-dione (2.50 g, crude). The crude product was used in the next step directly without further purification. LC-MS: (ES+H, m/z): [M+H]$^+$=313.2/315.2.

Step 5: Preparation of 7-bromo-4-chloro-8-fluoro-2-oxo-1H-quinoline-3-carbaldehyde A solution of (3Z)-7-bromo-3-[(dimethylamino)methylidene]-8-fluoro-1H-quinoline-2,4-dione (2.50 g, 7.98 mmol, 1.00 equiv.) and POCl$_3$ (1.46 g, 9.58 mmol, 1.20 equiv.) in DMF (40 mL) was stirred for 10 min at 0° C. under nitrogen atmosphere. The resulting mixture was stirred for 24 h at 60° C. under nitrogen atmosphere. The reaction was monitored by LCMS. The resulting mixture was diluted with water (50 mL) at 0° C. The precipitated solids were collected by filtration and washed with water (3×20 mL) to afford 7-bromo-4-chloro-8-fluoro-2-oxo-1H-quinoline-3-carbaldehyde (2.25 g, crude). The crude product was used in the next step directly without further purification. LC-MS: (ES+H, m/z): [M+H]$^+$=303.8/305.8.

Step 6: Preparation of 7-bromo-6-fluoro-1-methyl-5H-pyrazolo[4,3-c]quinolin-4-one and 7-bromo-6-fluoro-2-methyl-5H-pyrazolo[4,3-c]quinolin-4-one A solution of 7-bromo-4-chloro-8-fluoro-2-oxo-1H-quinoline-3-carbaldehyde (2.25 g, 7.38 mmol, 1.00 equiv.), K$_2$CO$_3$ (2.04 g, 14.77 mmol, 2.00 equiv.) and methylhydrazine (1.28 g, 8.86 mmol, 1.20 equiv.) in DMF (25 mL) was stirred overnight at 80° C. under nitrogen atmosphere. The reaction was monitored by LCMS. The mixture was allowed to cool down to room temperature. The precipitated solids were collected by filtration and washed with water (3×50 mL). The resulting solid was dried under vacuum to afford a mixture of 7-bromo-6-fluoro-1-methyl-5H-pyrazolo[4,3-c]quinolin-4-one and 7-bromo-6-fluoro-2-methyl-5H-pyrazolo[4,3-c]quinolin-4-one (3.50 g, crude). The crude product was used in the next step directly without further purification. LC-MS: (ES+H, m/z): [M+H]$^+$=295.9/297.9. $^1$H NMR (300 MHz, DMSO-d$_6$) δ 11.38 (s, 1H), 8.15 (s, 1H), 7.97 (dd, J=8.8, 1.5 Hz, 1H), 7.55 (dd, J=8.8, 6.5 Hz, 1H), 4.35 (s, 3H).

Step 7: Preparation of 6-fluoro-7-(hydroxymethyl)-1-methyl-5H-pyrazolo[4,3-c]quinolin-4-one and 6-fluoro-7-(hydroxymethyl)-2-methyl-5H-pyrazolo[4,3-c]quinolin-4-one A solution of 7-bromo-6-fluoro-1-methyl-5H-pyrazolo[4,3-c]quinolin-4-one and 7-bromo-6-fluoro-2-methyl-5H-pyrazolo[4,3-c]quinolin-4-one (3.5 g, 11.82 mmol, 1.00 equiv.), 2nd Generation XPhos Precatalyst (930 mg, 1.18 mmol, 0.10 equiv.) and (tributylstannyl)methanol (4.55 g, 14.18 mmol, 1.20 equiv.) in dioxane (20 mL) was stirred overnight at 80° C. under nitrogen atmosphere. The reaction was monitored by LCMS. The mixture was allowed to cool down to room temperature. The resulting mixture was concentrated under vacuum and the crude residue was purified by silica gel column chromatography (CH$_2$Cl$_2$/MeOH (0% to 10% gradient in 20 min)) to afford 6-fluoro-7-(hydroxymethyl)-1-methyl-5H-pyrazolo[4,3-c]quinolin-4-one and 6-fluoro-7-(hydroxymethyl)-2-methyl-5H-pyrazolo[4,3-c]quinolin-4-one (mixture, 700 mg, 23.9%). LC-MS: (ES+H, m/z): [M+H]$^+$=247.9.

Step 8: Preparation of 7-(chloromethyl)-6-fluoro-1-methyl-5H-pyrazolo[4,3-c]quinolin-4-one and 7-(chloromethyl)-6-fluoro-2-methyl-5H-pyrazolo[4,3-c]quinolin-4-one To a stirred solution of 6-fluoro-7-(hydroxymethyl)-1-methyl-5H-pyrazolo[4,3-c]quinolin-4-one and 6-fluoro-7-(hydroxymethyl)-2-methyl-5H-pyrazolo[4,3-c]quinolin-4-one (700 mg, 2.83 mmol, 1.00 equiv.) and DMF (20 mg, 0.28 mmol, 0.10 equiv.) in DCM (10 mL) was added SOCl$_2$ (3368 mg, 28.31 mmol, 10.00 equiv.) dropwise at room temperature under nitrogen atmosphere. The resulting mixture was stirred for 2 h at room temperature under nitrogen atmosphere. The reaction was monitored by LCMS. The resulting mixture was concentrated under vacuum to afford 7-(chloromethyl)-6-fluoro-1-methyl-5H-pyrazolo[4,3-c]quinolin-4-one and 7-(chloromethyl)-6-fluoro-2-methyl-5H-pyrazolo[4,3-c]quinolin-4-one (700 mg, crude). The crude product was used in the next step directly without further purification. LC-MS: (ES+H, m/z): [M+H]$^+$=265.95.

Step 9: Preparation of 6-fluoro-5-[4-({6-fluoro-1-methyl-4-oxo-5H-pyrazolo[4,3-c]quinolin-7-yl}methyl)piperazin-1-yl]-N-methylpyridine-2-carboxamide and 6-fluoro-5-[4-({6-fluoro-2-methyl-4-oxo-5H-pyrazolo[4,3-c]quinolin-7-yl}methyl)piperazin-1-yl]-N-methylpyridine-2-carboxamide A solution of 7-(chloromethyl)-6-fluoro-1-methyl-5H-pyrazolo[4,3-c]quinolin-4-one and 7-(chloromethyl)-6-fluoro-2-methyl-5H-pyrazolo[4,3-c]quinolin-4-one (700 mg, 2.63 mmol, 1.00 equiv.), KI (43 mg, 0.26 mmol, 0.10 equiv.), DIEA (1702 mg, 13.17 mmol, 5.00 equiv.) and 6-fluoro-N-methyl-5-(piperazin-1-yl)pyridine-2-carboxamide (627 mg, 2.63 mmol, 1.00 equiv.) in MeCN (20 mL) was stirred for 3 h at 80° C. under nitrogen atmosphere. The reaction was monitored by LCMS. The mixture was allowed to cool down to room temperature. The precipitated solids were collected by filtration and washed with CH$_3$CN (3×10 mL) to afford the crude product. The crude products were further purified by HPLC (Column: YMC-Actus Triart C18 ExRS, 30*150 mm, 5 μm; Mobile Phase A: Water (10 mmol/L NH$_4$HCO$_3$+0.1% NH$_3$·H$_2$O), Mobile Phase B: MeOH—Preparative; Flow rate: 60 mL/min; Gradient: 45% B to 56% B in 13 min, 56% B; Wave Length: 254/220 nm) to afford 6-fluoro-5-[4-({6-fluoro-1-methyl-4-oxo-5H-pyrazolo[4,3-c]quinolin-7-yl}methyl)piperazin-1-yl]-N-methylpyridine-2-carboxamide (Example 19, 54 mg, 4.35%) and 6-fluoro-5-[4-({6-fluoro-2-methyl-4-oxo-5H-pyrazolo[4,3-c]quinolin-7-yl}methyl)piperazin-1-yl]-N-methylpyridine-2-carboxamide (Example 20, 1.8 mg, 0.14%).

Example 19: LC-MS: (ES+H, m/z): [M+H]$^+$=468.05; $^1$H NMR (400 MHz, DMSO-d$_6$) δ 11.34 (s, 1H), 8.40 (d, J=5.1 Hz, 1H), 8.13 (s, 1H), 8.02 (d, J=8.4 Hz, 1H), 7.84 (dd, J=8.0, 1.4 Hz, 1H), 7.56 (dd, J=10.6, 8.1 Hz, 1H), 7.34 (t, J=7.5 Hz, 1H), 4.36 (s, 3H), 3.74 (s, 2H), 3.23-3.11 (m, 4H), 2.76 (d, J=4.8 Hz, 3H), 2.66-2.56 (m, 4H). $^{19}$F NMR (377 MHz, DMSO-d$_6$) δ−72.56, −131.30.

Example 20: LC-MS: (ES+H, m/z): [M+H]$^+$=468.0; $^1$H NMR (400 MHz, DMSO-d$_6$) δ 11.05 (s, 1H), 8.59 (s, 1H), 8.40 (d, J=5.5 Hz, 1H), 7.82 (dd, J=16.8, 8.0 Hz, 2H), 7.55 (t J=9.4 Hz, 1H), 7.24 (t, J=7.4 Hz, 1H), 4.10 (s, 3H), 3.69 (s, 2H), 3.24-3.08 (m, 4H), 2.76 (d, J=4.7 Hz, 3H), 2.66-2.56 (m, 4H). $^{19}$F NMR (377 MHz, DMSO-d$_6$) δ−72.54, −132.86.

Example 25

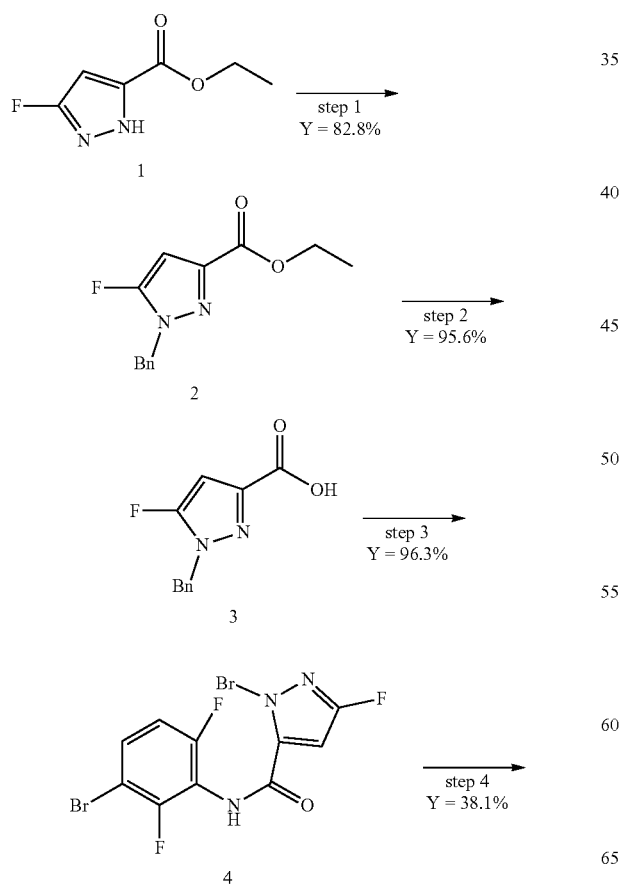

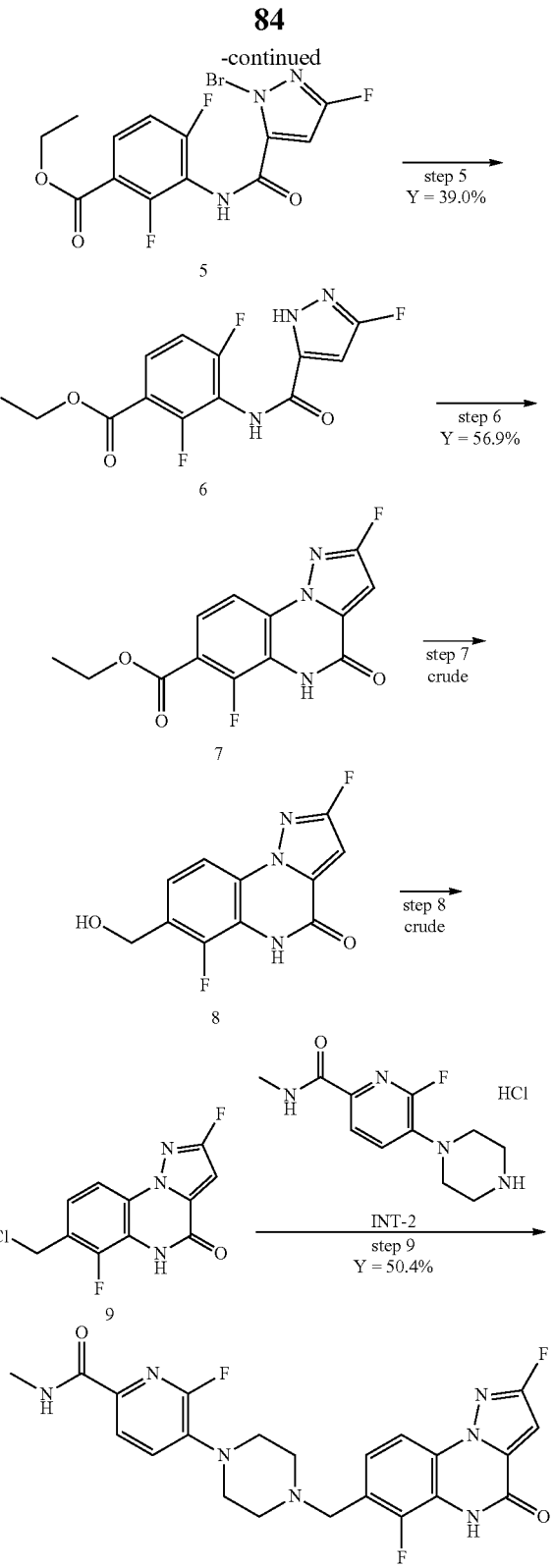

Step 1: Preparation of ethyl 1-benzyl-5-fluoro-1H-pyrazole-3-carboxylate

To a stirred solution of ethyl 3-fluoro-1H-pyrazole-5-carboxylate (1.00 g, 2.10 mmol, 1.00 equiv.) and K$_2$CO$_3$ (1.75 g, 12.64 mmol, 2.00 equiv.) in DMF (10 mL) was added BnBr (2.16 g, 12.64 mmol, 2.00 equiv.) at room temperature under nitrogen atmosphere. The resulting mixture was stirred for 1 h at room temperature under nitrogen atmosphere. The reaction was monitored by LCMS. The resulting mixture was diluted with water (120 mL). The resulting mixture was extracted with EtOAc (3×100 mL), dried over anhydrous $Na_2SO_4$, filtered and concentrated. The residue was purified by silica gel column chromatography (PE/EtOAc (0 to 30% gradient in 30 min)) to afford ethyl 1-benzyl-5-fluoro-1H-pyrazole-3-carboxylate (1.3 g, 82.8%). LC-MS: (ES+H, m/z): $[M+H]^+$=249.1; 1H NMR (300 MHz, DMSO-$d_6$) b 7.41-7.24 (m, 3H), 7.23-7.12 (m, 2H), 6.68 (d, J=6.1 Hz, 1H), 5.61 (s, 2H), 4.29 (q, J=7.1 Hz, 2H), 1.26 (t, J=7.1 Hz, 3H).

Step 2: Preparation of 1-benzyl-5-fluoro-1H-pyrazole-3-carboxylic Acid

To a stirred solution of ethyl 1-benzyl-5-fluoro-1H-pyrazole-3-carboxylate (1.30 g, 8.22 mmol, 1.00 equiv.) in THF (10 mL) were added LiOH (984 mg, 41.10 mmol, 5.00 equiv., 2 M in water) at room temperature. The resulting solution was stirred for 2 h at room temperature. The reaction was monitored by LCMS. The mixture was acidified to pH 3 with 2N HCl(aq.) and the resulting mixture was extracted with EtOAc (3×100 mL), dried over anhydrous $Na_2SO_4$, filtered and concentrated to afford 1-benzyl-5-fluoro-1H-pyrazole-3-carboxylic acid (1.10 g, 95.6%). LC-MS: (ES-H, m/z): $[M-H]^-$=219.0.

Step 3: Preparation of 1-benzyl-N-(3-bromo-2,6-difluorophenyl)-3-fluoro-1H-pyrazole-5-carboxamide To a stirred solution of 1-benzyl-5-fluoro-1H-pyrazole-3-carboxylic acid (1.00 g, 4.54 mmol, 1.00 equiv.) and 3-bromo-2,6-difluoroaniline (1.13 g, 5.44 mmol, 1.20 equiv.) in T3P (2 mL, 50% in EA) was added DIEA (1.76 g, 13.62 mmol, 3.00 equiv.) at room temperature under nitrogen atmosphere. The resulting mixture was stirred for 2 h at 100° C. under nitrogen atmosphere. The reaction was monitored by LCMS. The mixture was allowed to cool down to room temperature. The resulting mixture was diluted with water (20 mL) and extracted with EtOAc (3×20 mL). The combined organic layers were dried over anhydrous $Na_2SO_4$, filtered and concentrated. The residue was purified by silica gel column chromatography, eluted with PEI EtOAc (0 to 20% gradient in 30 min) to afford 1-benzyl-N-(3-bromo-2,6-difluorophenyl)-3-fluoro-1H-pyrazole-5-carboxamide (1.40 g, 96.3%). LC-MS: (ES+H, m/z): $[M+H]^+$=409.9; $^1$H NMR (400 MHz, DMSO-$d_6$) δ 10.58 (s, 1H), 7.80-7.78 (m, 1H), 7.39-7.26 (m, 4H), 7.26-7.14 (m, 2H), 6.85 (d, J=5.8 Hz, 1H), 5.61 (s, 2H).

Step 4: Preparation of ethyl 3-(2-benzyl-5-fluoropyrazole-3-amido)-2,4-difluorobenzoate To a stirred solution of 2-benzyl-N-(3-bromo-2,6-difluorophenyl)-5-fluoropyrazole-3-carboxamide (800 mg, 1.95 mmol, 1.00 equiv.) and Pd(dppf)Cl$_2$ (142 mg, 0.19 mmol, 0.10 equiv.) in EtOH (6 mL) was added TEA (592 mg, 5.85 mmol, 3.00 equiv.) at room temperature under nitrogen atmosphere. The resulting mixture was stirred for 2 days at 110° C. under a carbon monoxide atmosphere. The reaction was monitored by LCMS. The mixture was allowed to cool down to room temperature. The resulting mixture was concentrated under vacuum. The residue was purified by silica gel column chromatography (PE/EtOAc (0 to 20% gradient in 30 min)) to afford ethyl 3-(2-benzyl-5-fluoropyrazole-3-amido)-2,4-difluorobenzoate (300 mg, 38.1%). LC-MS: (ES-H, m/z): $[M-H]^-$=402.1; $^1$H NMR (300 MHz, DMSO-$d_6$) δ 10.52 (s, 1H), 7.99-7.91 (m, 1H), 7.45-7.24 (m, 4H), 7.23-7.17 (m, 2H), 6.85 (d, J=5.9 Hz, 1H), 5.62 (s, 2H), 4.34 (q, J=7.1 Hz, 2H), 1.32 (t, J=7.1 Hz, 3H).

Step 5: Preparation of ethyl 2,4-difluoro-3-(3-fluoro-1H-pyrazole-5-carboxamido)benzoate To a stirred solution of ethyl 3-(1-benzyl-3-fluoro-1H-pyrazole-5-carboxamido)-2,4-difluorobenzoate (200 mg, 0.51 mmol, 1.00 equiv.) in MeOH (3 mL) and 2 M HCl. (aq.) (0.2 mL) was added Pd(OH)$_2$/C (72 mg, 0.10 mmol, 0.20 equiv., 20%) at room temperature under nitrogen atmosphere. The resulting mixture was stirred overnight at room temperature under hydrogen atmosphere. The reaction was monitored by LCMS. The resulting mixture was filtered and the filter cake was washed with MeOH (3×3 mL). The filtrate was concentrated under reduced pressure and the crude residue was purified by silica gel column chromatography (PE/EtOAc (0 to 20% gradient in 30 min)) to afford ethyl 2,4-difluoro-3-(3-fluoro-1H-pyrazole-5-carboxamido)benzoate (240 mg, 39.0%). LC-MS: (ES-H, m/z): $[M-H]^-$=311.9; $^1$H NMR (300 MHz, DMSO-$d_6$) δ 13.57 (d, J=2.2 Hz, 1H), 10.46 (s, 1H), 8.07-7.80 (m, 1H), 7.44-7.37 (m, 1H), 6.76 (dd, J=6.2, 2.3 Hz, 1H), 4.34 (q, J=7.1 Hz, 2H), 1.32 (t, J=7.1 Hz, 3H).

Step 6: Preparation of ethyl 2,6-difluoro-4-oxo-4,5-dihydropyrazolo[1,5-a]quinoxaline-7-carboxylate To a stirred solution of ethyl 2,4-difluoro-3-(5-fluoro-2H-pyrazole-3-amido)benzoate (300 mg, 0.95 mmol, 1.00 equiv.) in DMA (4 mL) were added NaH (76 mg, 1.91 mmol, 2.00 equiv., 60% in mineral oil) at 0° C. under nitrogen atmosphere. The resulting mixture was stirred overnight at 120° C. under nitrogen atmosphere. The reaction was monitored by LCMS. The mixture was allowed to cool down to room temperature. The resulting mixture was diluted with water (40 mL). The resulting mixture was extracted with EtOAc (3×30 mL). The combined organic layers were washed with water (2×40 mL), dried over anhydrous $Na_2SO_4$, filtered and concentrated. The crude product was purified by silica gel column chromatography (PE/EtOAc (0 to 30% gradient in 30 min) to afford ethyl 2,6-difluoro-4-oxo-4,5-dihydropyrazolo[1,5-a]quinoxaline-7-carboxylate (160 mg, 56.9%). LC-MS: (ES-H, m/z): $[M-H]^-$=292.0; H NMR (300 MHz, DMSO-$d_6$) δ 12.32 (s, 1H), 7.88-7.83 (m, 1H), 7.80-7.75 (m, 1H), 7.08 (d, J=5.6 Hz, 1H), 4.36 (q, J=7.1 Hz, 2H), 1.34 (t, J=7.1 Hz, 3H).

Step 7: Preparation of 2,6-difluoro-7-(hydroxymethyl)pyrazolo[1,5-a]quinoxalin-4(5H)-one To a stirred solution of ethyl 2,6-difluoro-4-oxo-5H-pyrazolo[1,5-a]quinoxaline-7-carboxylate (150 mg, 0.10 mmol, 1.00 equiv.) in THF (4 mL) were added LiEt$_3$BH (1.5 mL, 1.53 mmol, 3.00 equiv., 1 M in THF) dropwise at 0° C. under nitrogen atmosphere. The resulting mixture was stirred for 2 h at 0° C. under nitrogen atmosphere. The reaction was monitored by LCMS. The reaction was quenched by the addition of water (1 mL) at 0° C. The resulting mixture was concentrated under reduced pressure. The residue was purified by silica gel column chromatography (PE/EtOAc (40 to 70% gradient in 30 min) to afford 2,6-difluoro-7-(hydroxymethyl)pyrazolo[1,5-a]quinoxalin-4(5H)-one (102 mg, crude). LC-MS: (ES-H, m/z): [M–H]⁻= 250.0.

Step 8: Preparation of 7-(chloromethyl)-2,6-difluoropyrazolo[1,5-a]quinoxalin-4(5H)-one To a stirred solution of 2,6-difluoro-7-(hydroxymethyl)-5H-pyrazolo[1,5-a]quinoxalin-4-one (90 mg, 0.35 mmol, 1.00 equiv.) and DMF (2 mg, 0.03 mmol, 0.10 equiv.) in CH$_2$Cl$_2$ (3 mL) were added SOCl$_2$ (255 mg, 2.14 mmol, 6.00 equiv.) dropwise at 0° C. under nitrogen atmosphere. The resulting mixture was stirred overnight at room temperature under nitrogen atmosphere. The reaction was monitored by LCMS. The filtrate was concentrated under reduced pressure to afford 7-(chloromethyl)-2,6-difluoropyrazolo[1,5-a]quinoxalin-4(5H)-one (90 mg, crude). LC-MS: (ES-H, m/z): [M–H]⁻=268.0.

Step 9: Preparation of 5-[4-({2,6-difluoro-4-oxo-5H-pyrazolo[1,5-a]quinoxalin-7-yl}methyl)piperazin-1-yl]-6-fluoro-N-methylpyridine-2-carboxamide To a stirred solution of 7-(chloromethyl)-2,6-difluoro-5H-pyrazolo[1,5-a]quinoxalin-4-one (90 mg, 0.33 mmol, 1.00 equiv.) and 6-fluoro-N-methyl-5-(piperazin-1-yl)picolinamide hydrochloride (79 mg, 0.33 mmol, 1.00 equiv.) in MeCN (5 mL) were added DIEA (215 mg, 1.67 mmol, 5.00 equiv.) and KI (5 mg, 0.03 mmol, 0.10 equiv.) at room temperature under nitrogen atmosphere. The resulting mixture was stirred for 3 h at 80° C. under nitrogen atmosphere. The reaction was monitored by LCMS. The mixture was allowed to cool down to room temperature. The precipitated solids were collected by filtration and washed with MeOH (3×5 mL). The precipitated solids were purified by trituration with MeOH (6 mL). The precipitated solids were filtered and washed with MeOH (3×5 mL) to afford 5-[4-({2,6-difluoro-4-oxo-5H-pyrazolo[1,5-a]quinoxalin-7-yl}methyl)piperazin-1-yl]-6-fluoro-N-methylpyridine-2-carboxamide (82.3 mg, 50.4%). LC-MS: (ES+H, m/z): [M+H]⁺=472.2; ¹H NMR (300 MHz, DMSO-d$_6$) δ 12.17 (s, 1H), 8.41 (d, J=4.9 Hz, 1H), 7.87-7.72 (m, 2H), 7.56 (dd, J=10.7, 8.1 Hz, 1H), 7.40-7.30 (m, 1H), 6.98 (d, J=5.7 Hz, 1H), 3.69 (s, 2H), 3.18-3.15 (m, 4H), 2.76 (d, J=4.8 Hz, 3H), 2.63-2.60 (m, 4H). ¹⁹F NMR (282 MHz, DMSO-d$_6$) δ –72.59, –126.66, –131.30.

Example 28

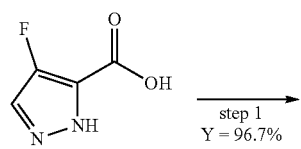

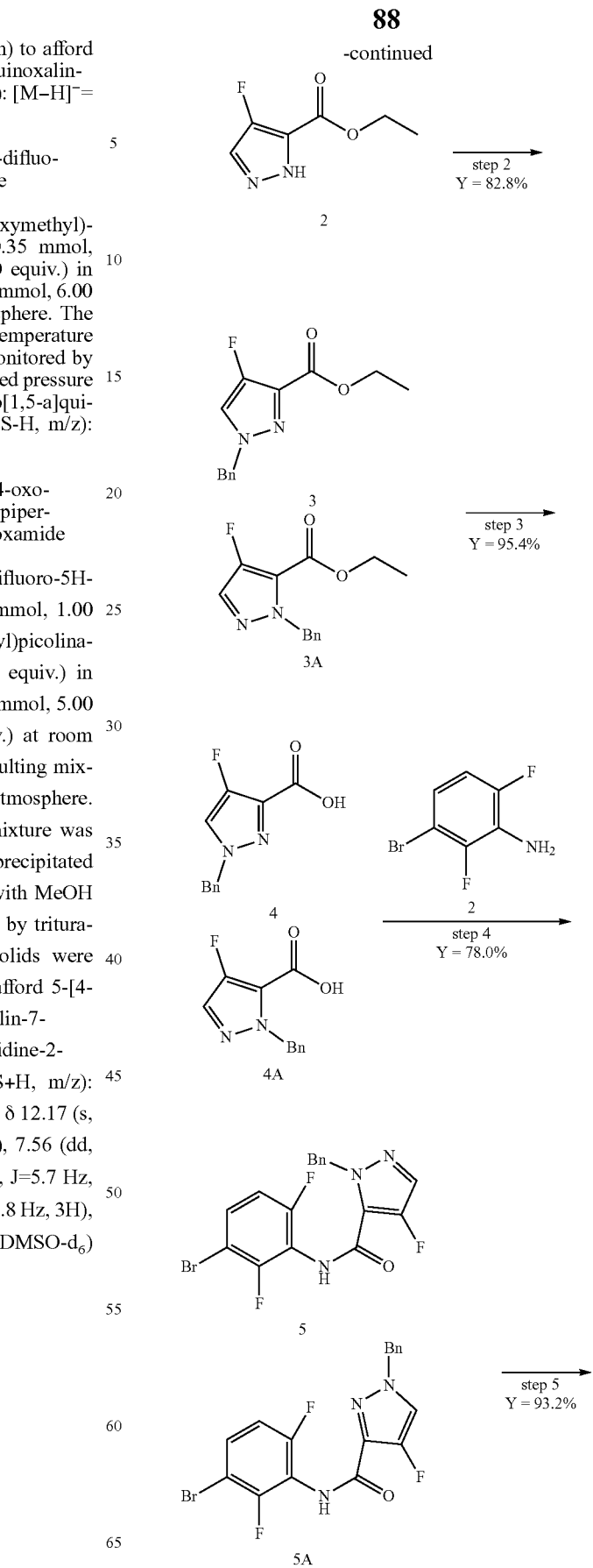

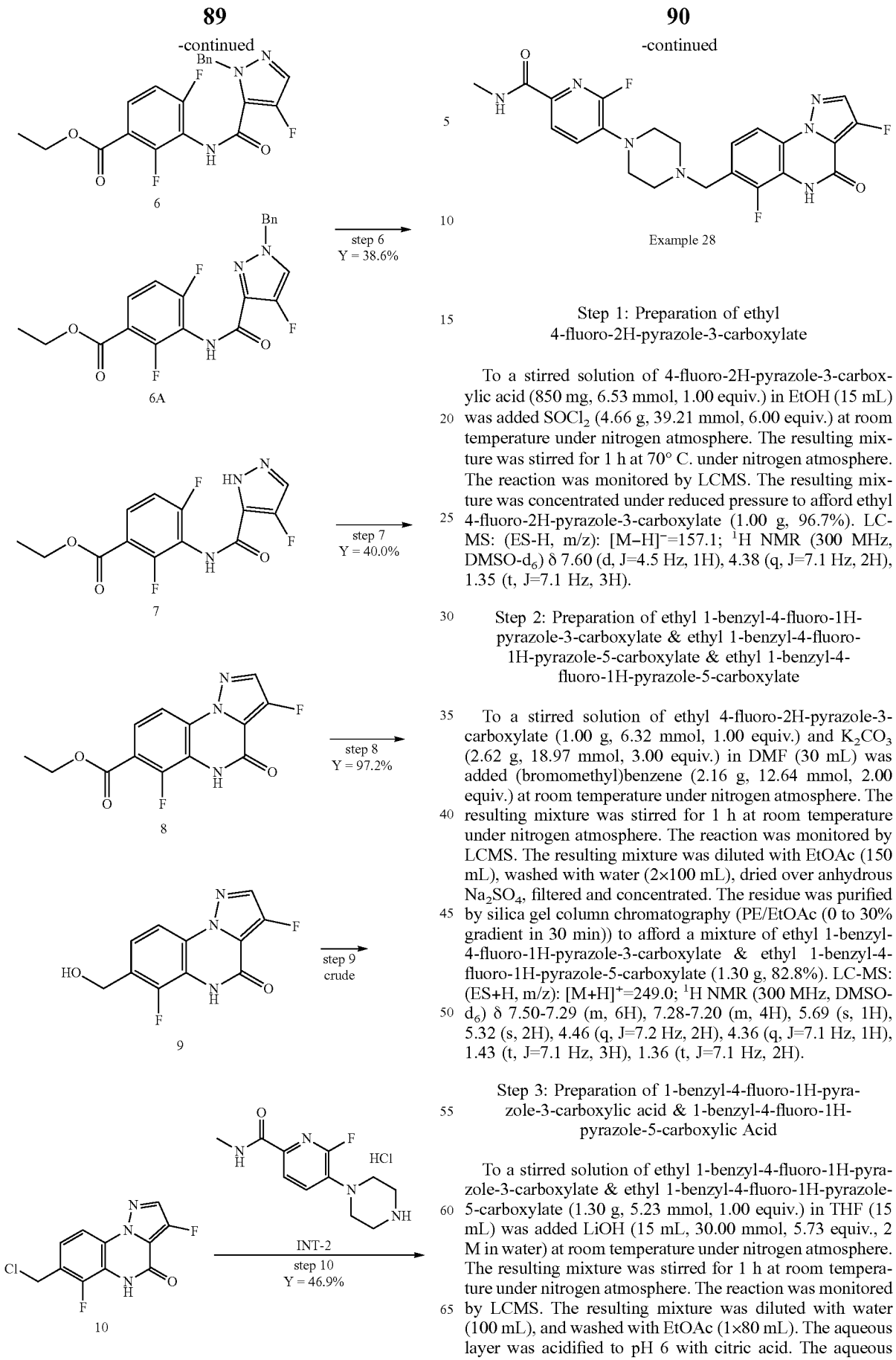

Example 28

Step 1: Preparation of ethyl 4-fluoro-2H-pyrazole-3-carboxylate

To a stirred solution of 4-fluoro-2H-pyrazole-3-carboxylic acid (850 mg, 6.53 mmol, 1.00 equiv.) in EtOH (15 mL) was added SOCl$_2$ (4.66 g, 39.21 mmol, 6.00 equiv.) at room temperature under nitrogen atmosphere. The resulting mixture was stirred for 1 h at 70° C. under nitrogen atmosphere. The reaction was monitored by LCMS. The resulting mixture was concentrated under reduced pressure to afford ethyl 4-fluoro-2H-pyrazole-3-carboxylate (1.00 g, 96.7%). LC-MS: (ES-H, m/z): [M−H]$^-$=157.1; $^1$H NMR (300 MHz, DMSO-d$_6$) δ 7.60 (d, J=4.5 Hz, 1H), 4.38 (q, J=7.1 Hz, 2H), 1.35 (t, J=7.1 Hz, 3H).

Step 2: Preparation of ethyl 1-benzyl-4-fluoro-1H-pyrazole-3-carboxylate & ethyl 1-benzyl-4-fluoro-1H-pyrazole-5-carboxylate & ethyl 1-benzyl-4-fluoro-1H-pyrazole-5-carboxylate To a stirred solution of ethyl 4-fluoro-2H-pyrazole-3-carboxylate (1.00 g, 6.32 mmol, 1.00 equiv.) and K$_2$CO$_3$ (2.62 g, 18.97 mmol, 3.00 equiv.) in DMF (30 mL) was added (bromomethyl)benzene (2.16 g, 12.64 mmol, 2.00 equiv.) at room temperature under nitrogen atmosphere. The resulting mixture was stirred for 1 h at room temperature under nitrogen atmosphere. The reaction was monitored by LCMS. The resulting mixture was diluted with EtOAc (150 mL), washed with water (2×100 mL), dried over anhydrous Na$_2$SO$_4$, filtered and concentrated. The residue was purified by silica gel column chromatography (PE/EtOAc (0 to 30% gradient in 30 min)) to afford a mixture of ethyl 1-benzyl-4-fluoro-1H-pyrazole-3-carboxylate & ethyl 1-benzyl-4-fluoro-1H-pyrazole-5-carboxylate (1.30 g, 82.8%). LC-MS: (ES+H, m/z): [M+H]$^+$=249.0; $^1$H NMR (300 MHz, DMSO-d$_6$) δ 7.50-7.29 (m, 6H), 7.28-7.20 (m, 4H), 5.69 (s, 1H), 5.32 (s, 2H), 4.46 (q, J=7.2 Hz, 2H), 4.36 (q, J=7.1 Hz, 1H), 1.43 (t, J=7.1 Hz, 3H), 1.36 (t, J=7.1 Hz, 2H).

Step 3: Preparation of 1-benzyl-4-fluoro-1H-pyrazole-3-carboxylic acid & 1-benzyl-4-fluoro-1H-pyrazole-5-carboxylic Acid To a stirred solution of ethyl 1-benzyl-4-fluoro-1H-pyrazole-3-carboxylate & ethyl 1-benzyl-4-fluoro-1H-pyrazole-5-carboxylate (1.30 g, 5.23 mmol, 1.00 equiv.) in THF (15 mL) was added LiOH (15 mL, 30.00 mmol, 5.73 equiv., 2 M in water) at room temperature under nitrogen atmosphere. The resulting mixture was stirred for 1 h at room temperature under nitrogen atmosphere. The reaction was monitored by LCMS. The resulting mixture was diluted with water (100 mL), and washed with EtOAc (1×80 mL). The aqueous layer was acidified to pH 6 with citric acid. The aqueous layer was extracted with EtOAc (3×100 mL) and the combined organic layers were dried over $Na_2SO_4$, filtered and concentrated afford 1-benzyl-4-fluoro-1H-pyrazole-3-carboxylic acid & 1-benzyl-4-fluoro-1H-pyrazole-5-carboxylic acid (1.10 g, 95.4%). LC-MS: (ES-H, m/z): $[M-H]^-$=219.1.

Step 4: Preparation of 2-benzyl-N-(3-bromo-2,6-difluorophenyl)-5-fluoropyrazole-3-carboxamide & 1-benzyl-N-(3-bromo-2,6-difluorophenyl)-4-fluoro-1H-pyrazole-3-carboxamide To a stirred solution of 1-benzyl-4-fluoro-1H-pyrazole-3-carboxylic acid & 1-benzyl-4-fluoro-1H-pyrazole-5-carboxylic acid (1.10 g, 4.99 mmol, 1.00 equiv.) in $T_3P$ (40 mL, 50% in EA) were added DIEA (1.94 g, 14.98 mmol, 3.00 equiv.) and 3-bromo-2,6-difluoroaniline (1.25 g, 5.99 mmol, 1.20 equiv.) at room temperature under nitrogen atmosphere. The resulting mixture was stirred for overnight at 100° C. under nitrogen atmosphere. The reaction was monitored by LCMS. The mixture was allowed to cool down to room temperature. The resulting mixture was diluted with EtOAc (120 mL). The resulting mixture was washed with 2×100 mL of water, dried over anhydrous $Na_2SO_4$, filtered and concentrated. The crude product was purified by silica gel column chromatography (PE/EtOAc (0 to 30% gradient in 30 min)) to afford a mixture of 2-benzyl-N-(3-bromo-2,6-difluorophenyl)-5-fluoropyrazole-3-carboxamide & 1-benzyl-N-(3-bromo-2,6-difluorophenyl)-4-fluoro-1H-pyrazole-3-carboxamide (1.60 g, 78.0%). LC-MS: (ES+H, m/z): $[M+H]^+$=410.0/412.0; $^1H$ NMR (300 MHz, DMSO-$d_6$) δ 10.25 (s, 1H), 10.06 (s, 1H), 8.22 (d, J=4.4 Hz, 1H), 7.84-7.67 (m, 2H), 7.45-7.28 (m, 7H), 7.28-7.15 (m, 3H), 5.56 (s, 1H), 5.40 (s, 2H).

Step 5: Preparation of ethyl 3-(2-benzyl-4-fluoropyrazole-3-amido)-2,4-difluorobenzoate & ethyl 3-(1-benzyl-4-fluoro-1H-pyrazole-3-carboxamido)-2,4-difluorobenzoate To a solution of 2-benzyl-N-(3-bromo-2,6-difluorophenyl)-5-fluoropyrazole-3-carboxamide & 1-benzyl-N-(3-bromo-2,6-difluorophenyl)-4-fluoro-1H-pyrazole-3-carboxamide (1.20 g, 2.92 mmol, 1.00 equiv.) in EtOH (8 mL) was added $Pd(dppf)Cl_2$ (214 mg, 0.29 mmol, 0.10 equiv.) in a pressure tank. The mixture was purged with nitrogen for 10 min and then was pressurized to 50 atm with carbon monoxide at 120° C. overnight. The reaction mixture was cooled to room temperature and filtered to remove insoluble solids. The resulting mixture was concentrated under reduced pressure and purified by silica gel column chromatography (PE/EtOAc (0 to 40% gradient in 40 min)) to afford a mixture of ethyl 3-(2-benzyl-4-fluoropyrazole-3-amido)-2,4-difluorobenzoate & ethyl 3-(1-benzyl-4-fluoro-1H-pyrazole-3-carboxamido)-2,4-difluorobenzoate (1.10 g, 93.2%). LC-MS: (ES+H, m/z): $[M+H]^-$=404.1; $^1H$ NMR (400 MHz, DMSO-$d_6$) δ 10.18 (s, 1H), 10.00 (s, 2H), 8.21 (d, J=4.4 Hz, 2H), 7.99-7.86 (m, 3H), 7.78 (d, J=4.3 Hz, 1H), 7.46-7.25 (m, 16H), 7.23-7.16 (m, 2H), 5.56 (s, 2H), 5.40 (s, 4H), 4.38-4.3 (m, 6H), 1.35-1.28 (m, 9H).

Step 6: Preparation of ethyl 2,4-difluoro-3-(4-fluoro-2H-pyrazole-3-amido)benzoate To a solution of ethyl 3-(2-benzyl-4-fluoropyrazole-3-amido)-2,4-difluorobenzoate & ethyl 3-(1-benzyl-4-fluoro-1H-pyrazole-3-carboxamido)-2,4-difluorobenzoate (500 mg, 1.24 mmol, 1.00 equiv.) in 20 mL MeOH/HCl=10:1 was added $Pd(OH)_2$/C (1.04 g, 1.49 mmol, 1.20 equiv., 20%) in a pressure tank. The mixture was hydrogenated at room temperature under 30 psi of hydrogen pressure overnight and then filtered through a Celite® pad which was further washed with DCM:MeOH=10:1 (3×50 mL). The resulting mixture was concentrated under reduced pressure. The residue was purified by silica gel column chromatography (PE/EtOAc (30 to 60% gradient in 30 min)) to afford ethyl 2,4-difluoro-3-(4-fluoro-2H-pyrazole-3-amido)benzoate (150 mg, 38.6%). LC-MS: (ES+H, m/z): $[M+H]^+$=314.1.

Step 7: Preparation of ethyl 3,6-difluoro-4-oxo-5H-pyrazolo[1,5-a]quinoxaline-7-carboxylate To a stirred solution of ethyl 2,4-difluoro-3-(4-fluoro-2H-pyrazole-3-amido)benzoate (160 mg, 0.51 mmol, 1.00 equiv.) in DMF (10 mL) was added $Cs_2CO_3$ (499 mg, 1.53 mmol, 3.00 equiv.) at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was diluted with water (40 mL). The resulting mixture was extracted with $CH_2Cl_2$:IPA=10:1 (3×30 mL). The combined organic layers were washed with water (2×40 mL), dried over anhydrous $Na_2SO_4$, filtered and concentrated. The residue was purified by silica gel column chromatography (PE/EtOAc (0 to 40% gradient in 40 min)) to afford ethyl 3,6-difluoro-4-oxo-5H-pyrazolo[1,5-a]quinoxaline-7-carboxylate (60 mg, 40.0%). LC-MS: (ES-H, m/z): $[M-H]^-$=292.0; $^1H$ NMR (300 MHz, DMSO-$d_6$) δ 12.11 (s, 1H), 8.32 (d, J=3.8 Hz, 1H), 7.99 (dd, J=8.8, 1.3 Hz, 1H), 7.77 (dd, J=8.8, 6.9 Hz, 1H), 4.37 (q, J=7.1 Hz, 2H), 1.34 (t, J=7.1 Hz, 3H).

Step 8: Preparation of 3,6-difluoro-7-(hydroxymethyl)-5H-pyrazolo[1,5-a]quinoxalin-4-one To a stirred solution of ethyl 3,6-difluoro-4-oxo-5H-pyrazolo[1,5-a]quinoxaline-7-carboxylate (60 mg, 0.20 mmol, 1.00 equiv.) in THF (4 mL) was added $LiEt_3BH$ (0.61 mL, 0.61 mmol, 3.00 equiv., 1 M in THF) dropwise at 0° C. under nitrogen atmosphere. The resulting mixture was stirred for 2 h at 0° C. under nitrogen atmosphere. The reaction was monitored by LCMS. The reaction was quenched by the addition of water (0.2 mL) at 0° C. The resulting mixture was concentrated under reduced pressure. The residue was purified by silica gel column chromatography ($CH_2Cl_2$/MeOH (0 to 10% gradient in 30 min)) to afford 3,6-difluoro-7-(hydroxymethyl)-5H-pyrazolo[1,5-a]quinoxalin-4-one (50 mg, 97.2%). LC-MS: (ES-H, m/z): $[M-H]^-$=249.9.

Step 9: Preparation of 7-(chloromethyl)-3,6-difluoro-5H-pyrazolo[1,5-a]quinoxalin-4-one To a stirred solution of 3,6-difluoro-7-(hydroxymethyl)-5H-pyrazolo[1,5-a]quinoxalin-4-one (50 mg, 0.19 mmol, 1.00 equiv.) and DMF (1 mg, 0.02 mmol, 0.10 equiv.) in DCM (1 mL) was added $SOCl_2$ (118 mg, 0.99 mmol, 5.00 equiv.) at room temperature under nitrogen atmosphere. The resulting mixture was stirred for 2 h at room temperature under nitrogen atmosphere. The reaction was monitored by LCMS. The resulting mixture was concentrated under reduced pressure to afford 7-(chloromethyl)-3,6-difluoro-5H-pyrazolo[1,5-a]quinoxalin-4-one (50 mg, crude). LC-MS: (ES-H, m/z): $[M-H]^-$=268.0.

Step 10: Preparation of 5-[4-({3,6-difluoro-4-oxo-5H-pyrazolo[1,5-a]quinoxalin-7-yl}methyl)piperazin-1-yl]-6-fluoro-N-methylpyridine-2-carboxamide To a stirred solution of 7-(chloromethyl)-3,6-difluoro-5H-pyrazolo[1,5-a]quinoxalin-4-one (50 mg, 0.18 mmol, 1.00 equiv.) and 6-fluoro-N-methyl-5-(piperazin-1-yl)pyridine-2-carboxamide hydrochloride (50 mg, 0.18 mmol, 1.00 equiv.) in MeCN (3 mL) were added KI (3 mg, 0.01 mmol, 0.10 equiv.) and DIEA (95 mg, 0.74 mmol, 4.00 equiv.) at room temperature under nitrogen atmosphere. The resulting mixture was stirred for 2 h at 80° C. under nitrogen atmosphere. The reaction was monitored by LCMS. The mixture was allowed to cool down to room temperature. The resulting mixture was diluted with MeCN (5 mL) and the precipitated solids were collected by filtration and washed with MeOH (3×3 mL). The precipitated solids were then purified by trituration with MeOH (4 mL), filtered, and washed with MeOH (3×2 mL). The precipitated solids were then further purified by trituration with hexane (4 mL). The precipitated solids were collected by filtration and washed with MeOH (3×2 mL) to afford 5-[4-({3,6-difluoro-4-oxo-5H-pyrazolo[1,5-a]quinoxalin-7-yl}methyl)piperazin-1-yl]-6-fluoro-N-methylpyridine-2-carboxamide (42 mg, 46.9%). LC-MS: (ES+H, m/z): [M+H]$^+$=472.1; $^1$H NMR (300 MHz, DMSO-d$_6$) δ 11.95 (s, 1H), 8.40 (q, J=4.6 Hz, 1H), 8.22 (d, J=3.8 Hz, 1H), 7.91 (dd, J=8.5, 1.3 Hz, 1H), 7.84 (dd, J=8.0, 1.5 Hz, 1H), 7.56 (dd, J=10.6, 8.1 Hz, 1H), 7.35 (dd, J=8.6, 6.8 Hz, 1H), 3.69 (s, 2H), 3.19-3.16 (m, 4H), 2.76 (d, J=4.8 Hz, 3H), 2.63-2.59 (m, 4H). $^{19}$F NMR (282 MHz, DMSO-d$_6$) δ −72.59, −130.76, −168.39.

The following examples were made using similar procedures shown for Example 28.

Example 31

Step 1: Preparation of 7-bromo-8-fluoro-1H-3,1-benzoxazine-2,4-dione

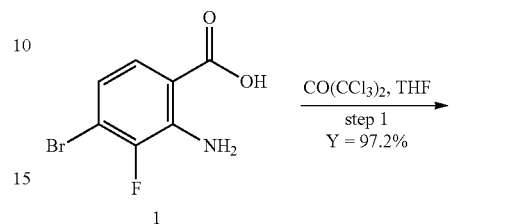

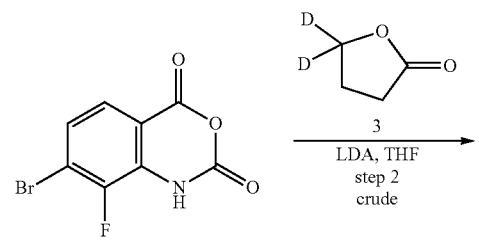

| Ex | Structure | NMR | LCMS (ESI) m/z |
|---|---|---|---|
| 33 | 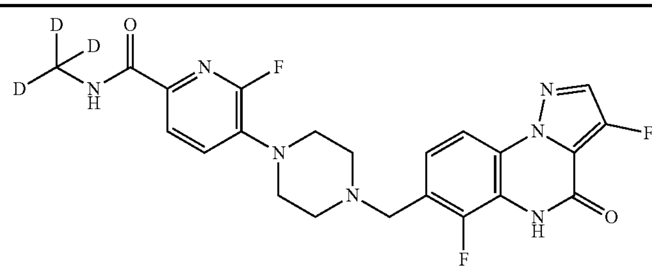 | $^1$H NMR (300 MHz, DMSO-d$_6$) δ 11.98 (s, 1H), 8.37 (s, 1H), 8.22 (d, J = 3.8 Hz, 1H), 7.90 (dd, J = 8.5, 1.3 Hz, 1H), 7.84 (dd, J = 8.0, 1.5 Hz, 1H), 7.56 (dd, J = 10.6, 8.1 Hz, 1H), 7.34 (dd, J = 8.5, 6.9 Hz, 1H), 3.69 (s, 2H), 3.17 (m, 4H), 2.60 (m, 4H).$^{19}$F NMR (282 MHz, DMSO-d$_6$) δ −72.59, −130.76, −168.39. | [M + H]$^+$ = 475.1 |
| 34 | 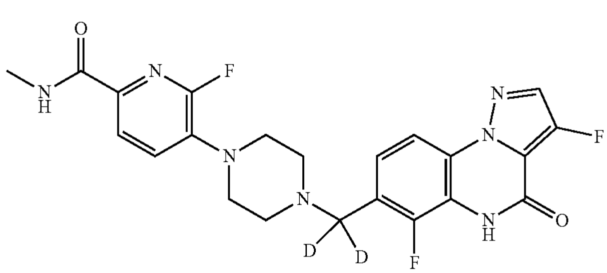 [SMILES: [2H]C([2H])(c1ccc2c([nH]c(=O)c3c(F)cnn32)c1F)N1CCN(c2ccc(C(=O)NC)nc2F)CC1] | $^1$H NMR (400 MHz, DMSO-d$_6$) δ 11.99 (s, 1H), 8.41 (q, 1H), 8.22 (d, J = 3.8 Hz, 1H), 7.91 (dd, J = 8.5, 1.2 Hz, 1H), 7.84 (dd, J = 8.0, 1.4 Hz, 1H), 7.56 (dd, J = 10.6, 8.1 Hz, 1H), 7.34 (dd, J = 8.5, 6.8 Hz, 1H), 3.22-3.12 (m, 4H), 2.76 (d, J = 4.8 Hz, 3H), 2.60 (m, 4H).$^{19}$F NMR (282 MHz, DMSO-d$_6$) δ −168.39, −130.79, −72.59 | [M + H]$^+$ = 474.15 |

-continued

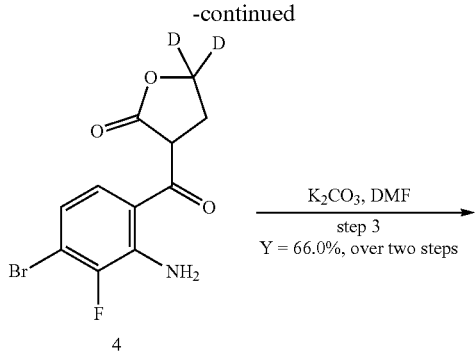

4

K₂CO₃, DMF
step 3
Y = 66.0%, over two steps

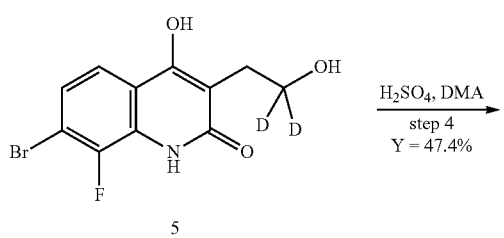

5

H₂SO₄, DMA
step 4
Y = 47.4%

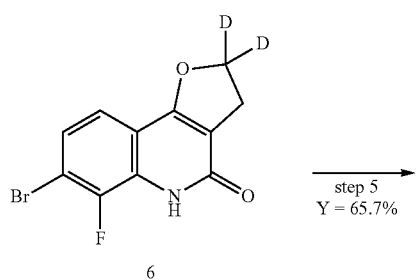

6 step 5
Y = 65.7%

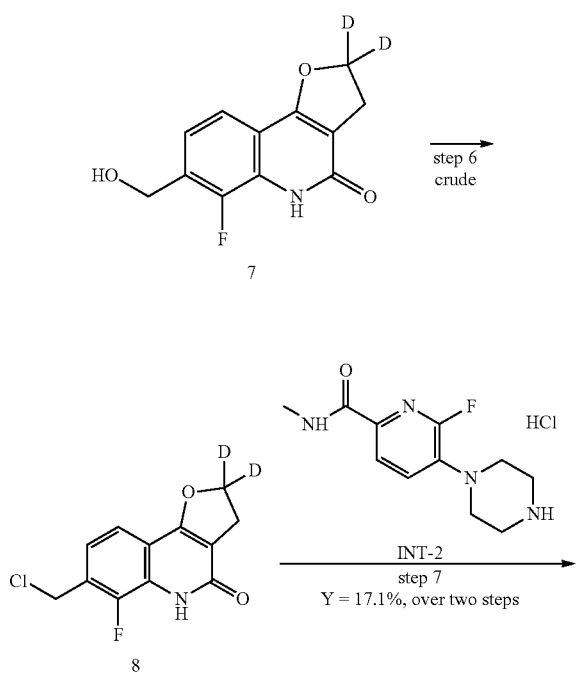

7 step 6
crude

8

INT-2
step 7
Y = 17.1%, over two steps

-continued

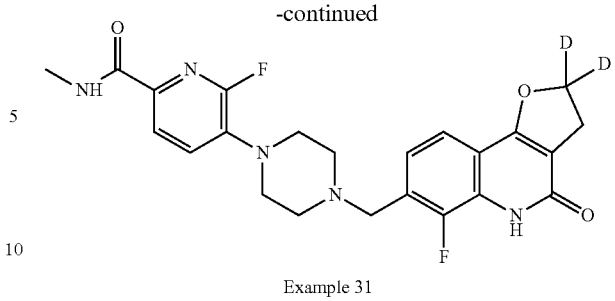

Example 31

To a stirred mixture of 2-amino-4-bromo-3-fluorobenzoic acid (50.00 g, 213.65 mmol, 1.00 equiv.) in THF (500 mL) was added ditrichloromethyl carbonate (31.70 g, 106.82 mmol, 0.50 equiv.) in THF (200 mL) dropwise at 0° C. under nitrogen atmosphere. The resulting mixture was stirred for 2 h at room temperature under nitrogen atmosphere. The reaction was monitored by LCMS. The resulting mixture was concentrated under reduced pressure. The residue was dissolved in THF (100 mL), stirred for 30 min, and then concentrated. The residue was then dissolved in hexane (100 mL). The resulting mixture was stirred for 30 min at room temperature under nitrogen atmosphere. The precipitated solids were collected by filtration and washed with hexane (3×100 mL). The resulting mixture was concentrated under reduced pressure to afford 7-bromo-8-fluoro-1H-3,1-benzoxazine-2,4-dione (54 g, 97.2%). LC-MS: (ES-H, m/z): [M−H]⁻=257.8/259.8; ¹H NMR (400 MHz, DMSO-d₆) δ 12.15 (s, 1H), 7.68 (dt, J=8.6, 1.6 Hz, 1H), 7.53 (ddd, J=8.4, 6.0, 1.9 Hz, 1H). ¹⁹F NMR (377 MHz, DMSO-d₆) δ−122.54.

Step 2: Preparation of 3-(2-amino-4-bromo-3-fluorobenzoyl)dihydrofuran-2(3H)-one-5,5-d2

Preparation of dihydrofuran-2(3H)-one-5,5-d2: To a stirred solution of succinic anhydride (10.00 g, 100.02 mmol, 1.00 equiv.) in THF (200 mL) was added LiAlD₄ (60 mL, 60.01 mmol, 0.60 equiv., 1 M in THF) dropwise at −55° C. under nitrogen atmosphere. The mixture was allowed to warm to 0° C. and stirred for 1.5 h. The reaction was monitored by TLC (PE:EA=1:1). The reaction was quenched by the addition of HCl (aq. 6 M) (35 mL) at −15° C. The resulting mixture was extracted with CH₂Cl₂ (3×500 mL). The combined organic layers were washed with brine (2×300 mL), dried over anhydrous MgSO₄, filtered and concentrated to afford dihydrofuran-2(3H)-one-5,5-d2 (4.5 g, 51.0%). ¹H NMR (400 MHz, CDCl₃) δ 2.56-2.47 (m, 2H), 2.31-2.20 (m, 2H).

To a stirred mixture of 7-bromo-8-fluoro-1H-3,1-benzoxazine-2,4-dione (4.50 g, 17.30 mmol, 1.00 equiv.) and dihydrofuran-2(3H)-one-5,5-d2 (2.29 g, 25.95 mmol, 1.50 equiv.) in THF (90 mL) was added LDA (30.29 mL, 60.57 mmol, 3.50 equiv., 2 M in THF) dropwise at −70° C. under nitrogen atmosphere. The resulting mixture was stirred for 1 h at 0° C. under nitrogen atmosphere. The reaction was monitored by LCMS. The reaction was quenched by the addition of MeOH (30 mL) at −15° C. The resulting mixture was concentrated under reduced pressure. The crude product was used in the next step directly without further purification. LC-MS: (ES-H, m/z): [M−H]⁻=301.9/303.9.

Step 3: Preparation of 7-bromo-8-fluoro-4-hydroxy-3-(2-hydroxyethyl-2,2-d2)quinolin-2(1H)-one To a stirred solution of 3-(2-amino-4-bromo-3-fluorobenzoyl)dihydrofuran-2(3H)-one-5,5-d2 (5.3 g, assumed 100% yield, 17.42 mmol, 1.00 equiv.) in DMF (100 mL) was added K$_2$CO$_3$ (4.82 g, 34.85 mmol, 2.00 equiv.) at room temperature under nitrogen atmosphere. The resulting mixture was stirred for 2 h at 80° C. under nitrogen atmosphere. The reaction was monitored by LCMS. The mixture was allowed to cool down to room temperature. The mixture was diluted with ice water (800 mL) and then acidified to pH 4 with citric acid. The resulting mixture was stirred for 1 h at room temperature. The precipitated solids were collected by filtration, washed with water (3×100 mL), and dried to afford 7-bromo-8-fluoro-4-hydroxy-3-(2-hydroxyethyl-2,2-d2) quinolin-2(1lH)-one (3.5 g, 66.0%). LC-MS: (ES+H, m/z): [M+H]$^+$=304.0/306.0; $^1$H NMR (400 MHz, DMSO-d$_6$) δ 11.55 (s, 1H), 7.60 (dd, J=8.7, 1.4 Hz, 1H), 7.39 (dd, J=8.7, 6.2 Hz, 1H), 2.79 (s, 2H).

Step 4: Preparation of 7-bromo-6-fluoro-3,5-dihydrofuro[3,2-c]quinolin-4(2H)-one-2,2-d2

To a stirred mixture of 7-bromo-8-fluoro-4-hydroxy-3-(2-hydroxyethyl-2,2-d2)quinolin-2(1H)-one (3.00 g, 9.86 mmol, 1.00 equiv.) in DMA (30 mL) was added H$_2$SO$_4$ (3 mL) dropwise at room temperature under nitrogen atmosphere. The resulting mixture was stirred for 3 h at 140° C. under nitrogen atmosphere. The reaction was monitored by LCMS. The mixture was allowed to cool down to room temperature. The resulting mixture was diluted with ice water (500 mL) and stirred for 1 h at room temperature. The precipitated solids were collected by filtration and washed with water (3×100 mL). MeOH (30 mL) was added and the precipitated solids were collected by filtration and washed with MeOH (3×5 mL). The resulting solid was dried to afford 7-bromo-6-fluoro-3,5-dihydrofuro[3,2-c]quinolin-4 (2H)-one-2,2-d2 (1.34 g, 47.4%). LC-MS: (ES+H, m/z): [M+H]+ 285.9/287.9. $^1$H NMR (400 MHz, DMSO-d$_6$) δ 11.63 (s, 1H), 7.43 (dd, J=8.6, 6.0 Hz, 1H), 7.36 (dd, J=8.6, 1.2 Hz, 1H), 3.05 (s, 2H).

Step 5: Preparation of 6-fluoro-7-(hydroxymethyl)-3,5-dihydrofuro[3,2-c]quinolin-4(2H)-one-2,2-d2

To a stirred mixture of 7-bromo-6-fluoro-3,5-dihydrofuro[3,2-c]quinolin-4(2H)-one-2,2-d2 (1.34 g, 4.68 mmol, 1.00 equiv.) and (tributylstannyl)methanol (3.01 g, 9.36 mmol, 2.00 equiv.) in dioxane (10 mL) was added 2nd Generation XPhos Precatalyst (737 mg, 0.93 mmol, 0.20 equiv.) at room temperature under nitrogen atmosphere. The resulting mixture was stirred overnight at 80° C. under nitrogen atmosphere. The reaction was monitored by LCMS. The resulting mixture was concentrated under reduced pressure. The residue was purified by silica gel column chromatography (CH$_2$Cl$_2$/MeOH (0% to 5% gradient in 30 min)) to afford 6-fluoro-7-(hydroxymethyl)-3,5-dihydrofuro[3,2-c]quinolin-4(2H)-one-2,2-d2 (730 mg, 65.7%). LC-MS: (ES-H, m/z): [M-H]$^-$=238.0; $^1$H NMR (300 MHz, DMSO-d$_6$) δ 11.38 (s, 1H), 7.40 (d, J=8.1 Hz, 1H), 7.26 (dd, J=8.2, 6.3 Hz, 1H), 5.44 (s, 1H), 4.64 (s, 2H), 3.05 (s, 2H). $^{19}$F NMR (282 MHz, DMSO-d$_6$) δ−134.69.

Step 6: Preparation of 7-(chloromethyl)-6-fluoro-3,5-dihydrofuro[3,2-c]quinolin-4(2H)-one-2,2-d2

To a stirred mixture of 6-fluoro-7-(hydroxymethyl)(2,2-2H2)-3H,5H-furo[3,2-c]quinolin-4-one (711 mg, 2.99 mmol, 1.00 equiv.) in DCM (10 mL) was added SOCl$_2$ (2139 mg, 17.98 mmol, 6.00 equiv.) dropwise at 0° C. under nitrogen atmosphere. The resulting mixture was stirred overnight at room temperature under nitrogen atmosphere. The reaction was monitored by LCMS. The resulting mixture was concentrated under reduced pressure to afford 7-(chloromethyl)-6-fluoro-3,5-dihydrofuro[3,2-c]quinolin-4 (2H)-one-2,2-d2 (779 mg, crude). LC-MS: (ES+H, m/z): [M+H]$^+$=256.0.

Step 7: Preparation of 6-fluoro-5-(4-((6-fluoro-4-oxo-2,3,4,5-tetrahydrofuro[3,2-c]quinolin-7-yl-2,2-d2)methyl)piperazin-1-yl)-N-methylpicolinamide To a stirred mixture of 7-(chloromethyl)-6-fluoro-3,5-dihydrofuro[3,2-c]quinolin-4(2H)-one-2,2-d2 (779 mg, assumed 100% yield, 3.04 mmol, 1.00 equiv.) and 6-fluoro-N-methyl-5-(piperazin-1-yl)pyridine-2-carboxamide hydrochloride (837 mg, 3.04 mmol, 1.00 equiv.) in MeCN (30 mL) were added DIEA (1.58 g, 12.18 mmol, 4.00 equiv.) and KI (51 mg, 0.30 mmol, 0.10 equiv.) at room temperature under nitrogen atmosphere. The resulting mixture was stirred for 2 h at 80° C. under nitrogen atmosphere. The reaction was monitored by LCMS. The precipitated solids were collected by filtration and washed with MeCN (3×20 mL). The residue was triturated with DMSO (15 mL) and the precipitated solids were collected by filtration and washed with MeOH (3×20 mL). The crude product (400 mg) was purified by Prep-HPLC (Column: XBridge Shield C18 OBD Column, 19*250 mm, 10 μm; Mobile Phase A: Water (10 mmol/L NH$_4$HCO$_3$+0.1% NH$_3$H$_2$O), Mobile Phase B: MeCN; Flow rate: 100 mL/min; Gradient: 10% B to 40% B in 30 min; Wave Length: 254/220 nm; RT1 (min): 10) to afford 6-fluoro-5-(4-((6-fluoro-4-oxo-2,3,4,5-tetrahydrofuro [3,2-c]quinolin-7-yl-2,2-d2)methyl)piperazin-1-yl)-N-methylpicolinamide (239.5 mg, 17.1%, over two steps). LC-MS: (ES+H, m/z): [M+H]$^+$=458.15; $^1$H NMR (400 MHz, DMSO-d$_6$) δ 11.42 (s, 1H), 8.41 (d, J=4.9 Hz, 1H), 7.84 (dd, J=8.2, 1.4 Hz, 1H), 7.55 (dd, J=10.6, 8.1 Hz, 1H), 7.41 (d, J=8.1 Hz, 1H), 7.23 (dd, J=8.2, 6.1 Hz, 1H), 3.69 (s, 2H), 3.17 (d, J=5.1 Hz, 4H), 3.06 (s, 2H), 2.76 (d, J=4.8 Hz, 3H), 2.58 (s, 4H). $^{19}$F NMR (282 MHz, DMSO-d$_6$) δ−72.56, −132.97.

Example 32

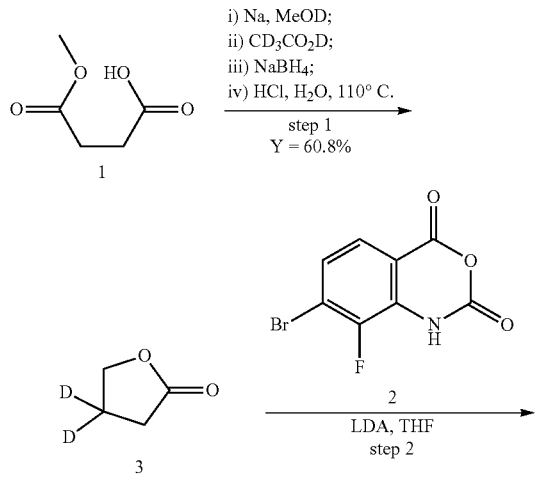

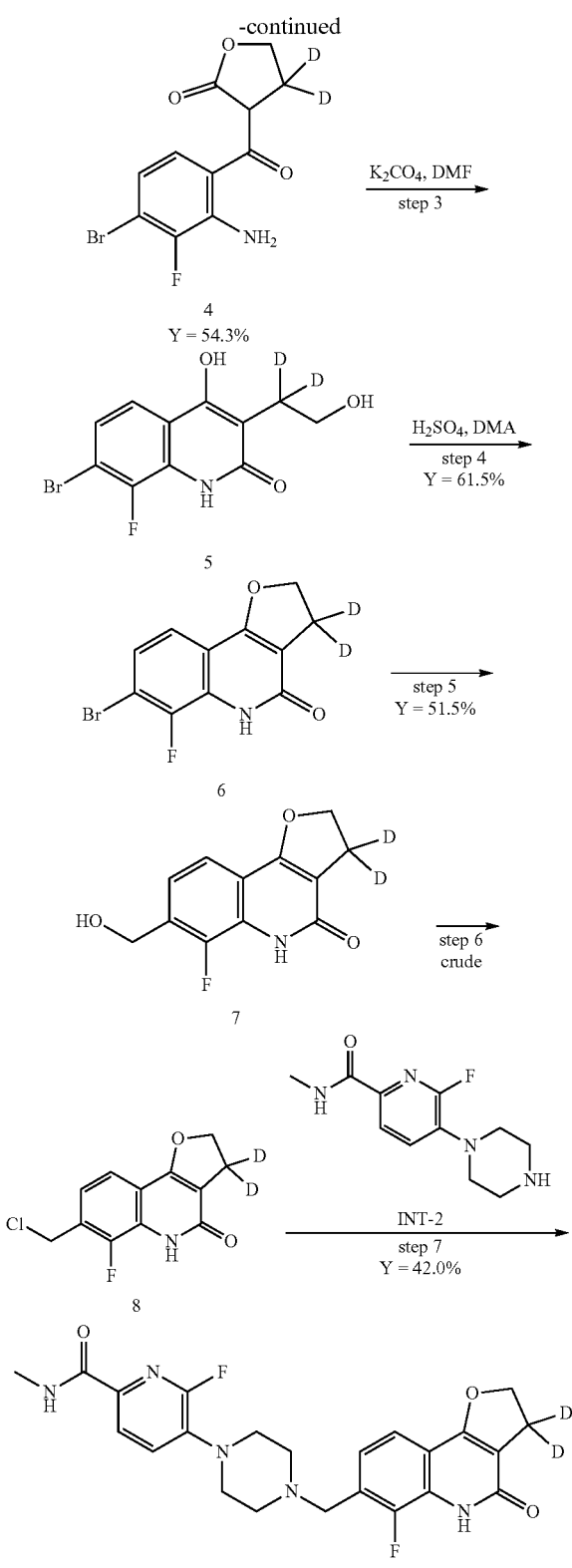

butanedioic acid, monomethyl ester (4.4 g, 33.61 mmol, 1.00 equiv.) was added, followed by methan-d3-ol-d (68 mL). The solution was heated to reflux for 24 h and then cooled in ice, and acetic-d3 acid-d (1.2 g, 18.15 mmol, 0.54 equiv.) was added. The solution was stirred for 20 min, and the solvent was then removed in vacuo. The white solid was dissolved in water (50 mL) and cooled in a water bath while NaBH$_4$ (10.9 g, 289.02 mmol, 8.60 equiv.) was added slowly, followed by more water (15 mL). The reaction was stirred at room temperature for 12.5 h and then cooled in ice. Conc. HCl (29 mL) was added, followed by additional conc. HCl (5.9 mL) and the solution was heated to 110° C. for 1 h. It was then cooled to room temperature, saturated with NaCl, and extracted with DCM (4×150 mL). The combined organic extracts were dried over MgSO$_4$ and concentrated to afford dihydrofuran-2(3H)-one-4,4-d2 (1.8 g, 60.8%). $^1$H NMR (300 MHz, CDCl$_3$) δ 4.35 (s, 2H), 2.49 (s, 2H).

Step 2 & 3: Preparation of 7-bromo-8-fluoro-4-hydroxy-3-(2-hydroxyethyl-1,1-d2)quinolin-2(1H)-one To a stirred mixture of 7-bromo-8-fluoro-1H-3,1-benzoxazine-2,4-dione (3.00 g, 11.54 mmol, 1.00 equiv.) in THF (20 mL) was added dihydrofuran-2(3H)-one-4,4-d2 (1.20 g, 13.85 mmol, 1.20 equiv.) at room temperature under nitrogen atmosphere. The mixture was allowed to cool down to −70° C. To the above mixture was added LDA (20 mL, 40.38 mmol, 3.50 equiv., 2 M in THF) dropwise over 1 h at −70° C. The resulting mixture was stirred for additional 3 h at 0° C. The reaction was monitored by LCMS. The reaction was quenched by the addition of MeOH (20 mL) at 0° C. and then concentrated. DMF (50 mL) was added to the residue followed by K$_2$CO$_3$ (3.20 g, 23.15 mmol, 2.00 equiv.) at room temperature under nitrogen atmosphere. The resulting mixture was stirred for additional 3 h at 80° C. under nitrogen atmosphere and the cooled to room temperature. The mixture was diluted with ice water (500 mL), acidified to pH 4 with citric acid, and stirred for 1 h at room temperature. The precipitated solids were collected by filtration, washed with water (3×50 mL), and dried at 45° C. to afford 7-bromo-8-fluoro-4-hydroxy-3-(2-hydroxyethyl-1,1-d2)quinolin-2(1H)-one (1.9 g, 54.3%, over two steps). LC-MS: (ES+H, m/z): [M+H]$^+$=303.9.

Step 4: Preparation of 7-bromo-6-fluoro-3,5-dihydrofuro[3,2-c]quinolin-4(2H)-one-3,3-d2

To a stirred mixture of 7-bromo-8-fluoro-4-hydroxy-3-(2-hydroxyethyl-1,1-d2)quinolin-2(1H)-one (1.90 g, 6.25 mmol, 1.00 equiv.) in DMA (30 mL) was added conc. H$_2$SO$_4$ (3 mL) dropwise at room temperature under nitrogen atmosphere (note: exothermic). The resulting mixture was stirred for 3 h at 140° C. under nitrogen atmosphere, cooled to room temperature, and then poured into ice water. The resulting mixture was stirred for additional 30 min at room temperature. The precipitated solids were collected by filtration, washed with water (3×20 mL) and dried at 45° C. to afford 7-bromo-6-fluoro-3,5-dihydrofuro[3,2-c]quinolin-4(2H)-one-3,3-d2 (1.1 g, 61.5%). LC-MS: (ES+H, m/z): [M+H]$^+$=285.9/287.9; $^1$H NMR (300 MHz, DMSO-d$_6$) δ 11.61 (s, 1H), 7.53-7.26 (m, 2H), 4.82 (s, 2H). $^{19}$F NMR (282 MHz, DMSO-d$_6$) δ−121.96.

Step 5: Preparation of 6-fluoro-7-(hydroxymethyl)-3,5-dihydrofuro[3,2-c]quinolin-4(2H)-one-3,3-d2

To a stirred mixture of 7-bromo-6-fluoro-3,5-dihydrofuro[3,2-c]quinolin-4(2H)-one-3,3-d2 (1.10 g, 3.85 mmol, 1.00

Step 1: Preparation of dihydrofuran-2(3H)-one-4,4-d2

Sodium (1.2 g, 51.76 mmol, 1.54 equiv.) was dissolved in methan-d3-ol-d (128 mL). Once the sodium was consumed, equiv.) and 2nd Generation XPhos Precatalyst (303 mg, 0.39 mmol, 0.10 equiv.) in dioxane (15 mL) were added (Tributylstannyl)methanol (1.50 g, 4.61 mmol, 1.20 equiv.) at room temperature under nitrogen atmosphere. The resulting mixture was stirred for 3 h at 80° C. under nitrogen atmosphere. The mixture was allowed to cool down to room temperature. The reaction was monitored by LCMS. The resulting mixture was concentrated under reduced pressure and the crude product was purified by silica gel column chromatography ($CH_2Cl_2$/MeOH (0%-10% in 30 min)) to afford 6-fluoro-7-(hydroxymethyl)-3,5-dihydrofuro[3,2-c] quinolin-4(2H)-one-3,3-d2 (470 mg, 51.5%). LC-MS: (ES+ H, m/z): $[M+H]^+$=238.0; $^1$H NMR (300 MHz, DMSO-$d_6$) δ 11.37 (s, 1H), 7.41 (dd, J=8.2, 1.0 Hz, 1H), 7.26 (dd, J=8.2, 6.3 Hz, 1H), 5.43 (t, J=5.8 Hz, 1H), 4.81 (s, 2H), 4.64 (dd, J=5.8, 1.6 Hz, 2H). $^{19}$F NMR (282 MHz, DMSO-$d_6$) δ−135.04.

Step 6: Preparation of 7-(chloromethyl)-6-fluoro-3,5-dihydrofuro[3,2-c]quinolin-4(2H)-one-3,3-d2

To a stirred mixture of 6-fluoro-7-(hydroxymethyl)-3,5-dihydrofuro[3,2-c]quinolin-4(2H)-one-3,3-d2 (470 mg, 1.98 mmol, 1.00 equiv.) in DCM (15 mL) was added $SOCl_2$ (0.9 mL, 11.89 mmol, 6.00 equiv.) dropwise at 0° C. under nitrogen atmosphere. The resulting mixture was stirred for 5 h at room temperature under nitrogen atmosphere. The reaction was monitored by LCMS. The resulting mixture was diluted with $CH_2Cl_2$ (10 mL) and then concentrated under reduced pressure. The crude product was diluted with THF (40 mL) and then concentrated under reduced pressure. The product was further purified by trituration with MeCN (10 mL) to afford 7-(chloromethyl)-6-fluoro-3,5-dihydrofuro[3,2-c]quinolin-4(2H)-one-3,3-d2 (560 mg, crude). LC-MS: (ES+H, m/z): $[M+H]^+$=256.1

Step 7: Preparation of 6-fluoro-5-(4-((6-fluoro-4-oxo-2,3,4,5-tetrahydrofuro[3,2-c]quinolin-7-yl-3,3-d2)methyl)piperazin-1-yl)-N-methylpicolinamide To a stirred mixture of 7-(chloromethyl)-6-fluoro-3,5-dihydrofuro[3,2-c]quinolin-4(2H)-one-3,3-d2 (540 mg, 2.11 mmol, 1.00 equiv.) and 6-fluoro-N-methyl-5-(piperazin-1-yl)pyridine-2-carboxamide hydrochloride (580 mg, 2.11 mmol, 1.00 equiv.) in MeCN (15 mL) were added DIEA (1.10 g, 8.45 mmol, 4.00 equiv.) and KI (175 mg, 1.06 mmol, 0.50 equiv.) at room temperature. The resulting mixture was stirred for 2 h at 80° C. under nitrogen atmosphere. The mixture was allowed to cool down to room temperature. The reaction was monitored by LCMS. The resulting mixture was diluted with MeCN (10 mL) and the precipitated solids were collected by filtration and washed with MeCN (3×5 mL). The residue was purified by trituration with MeOH (10 mL). The precipitated solids were collected by filtration and washed with MeOH (3×10 mL). The residue was purified by trituration with DMSO (5 mL). The precipitated solids were collected by filtration and washed with MeOH (3×10 mL). The resulting solid was dried under reduced pressure and the crude product (550 mg) was purified by Prep-HPLC (Column: XBridge Shield C18 OBD Column, 19*250 mm, 10 m; Mobile Phase A: Water (10 mmol/L $NH_4HCO_3$+0.1% $NH_3H_2O$), Mobile Phase B: MeCN; Flow rate: 100 mL/min; Gradient: 10% B to 40% B in 30 min; Wave Length: 254/220 nm) to afford 6-fluoro-5-(4-((6-fluoro-4-oxo-2,3,4,5-tetrahydrofuro[3,2-c]quinolin-7-yl-3,3-d2)methyl)piperazin-1-yl)-N-methylpicolinamide (409.8 mg, 42.0%). LC-MS: (ES+H, m/z): [M+H]-=458.15; $^1$H NMR (300 MHz, DMSO-$d_6$) δ 11.42 (s, 1H), 8.40 (d, J=5.0 Hz, 1H), 7.84 (dd, J=8.0, 1.5 Hz, 1H), 7.55 (dd, J=10.6, 8.1 Hz, 1H), 7.40 (d, J=8.1 Hz, 1H), 7.22 (dd, J=8.2, 6.1 Hz, 1H), 4.81 (s, 2H), 3.69 (s, 2H), 3.16 (d, J=5.4 Hz, 4H), 2.76 (d, J=4.8 Hz, 3H), 2.59 (d, J=4.8 Hz, 4H). $^{19}$F NMR (282 MHz, DMSO-$d_6$) δ−72.56, −133.00.

COMPARATIVE EXAMPLES

Comparative Example 1 (Example 19 in WO2023025307

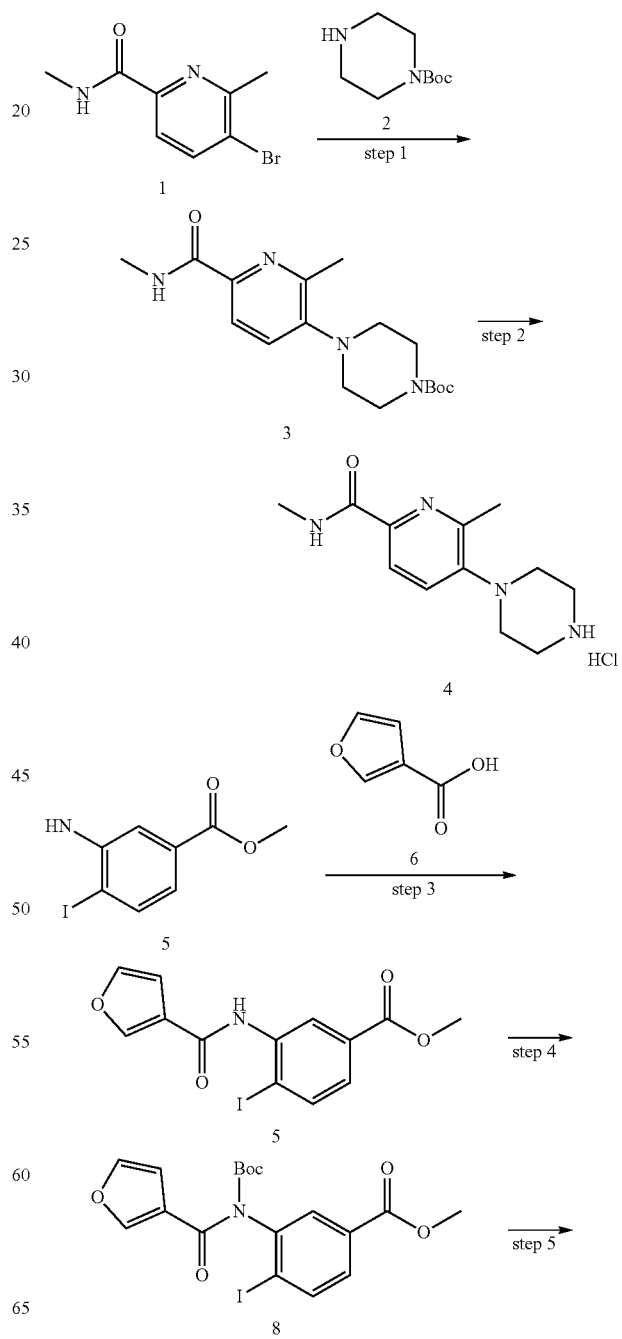

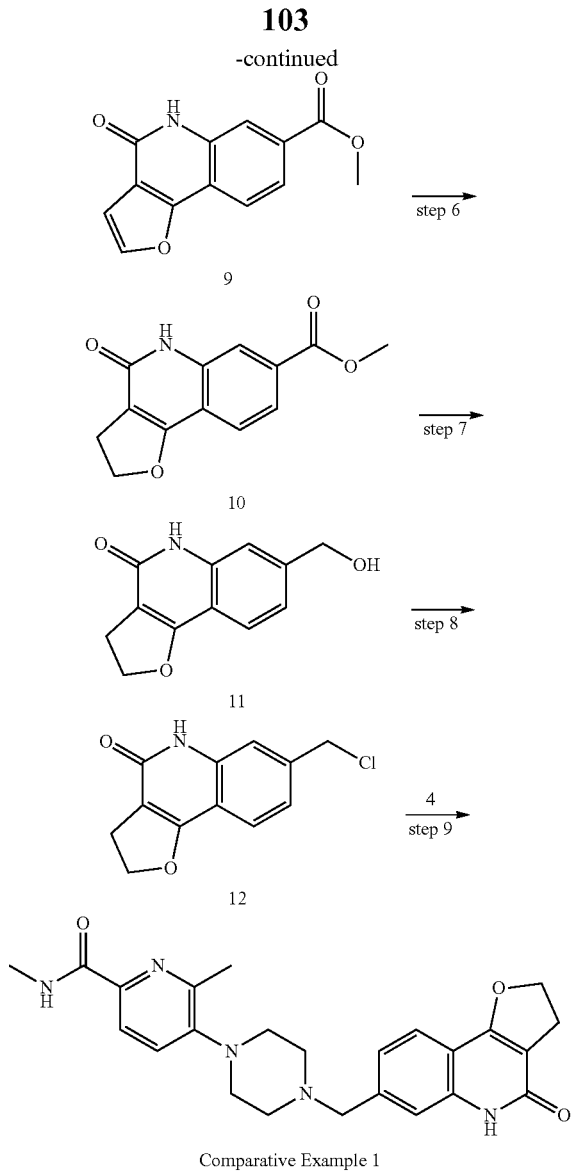

Comparative Example 1

Step 1: Preparation of tert-butyl 4-[2-methyl-6-(methylcarbamoyl)pyridin-3-yl]piperazine-1-carboxylate A mixture of 5-bromo-N,6-dimethylpyridine-2-carboxamide (1.00 g, 4.37 mmol, 1.00 equiv), tert-butyl piperazine-1-carboxylate (975 mg, 5.23 mmol, 1.20 equiv), BINAP (272 mg, 0.44 mmol, 0.10 equiv), Pd(OAc)$_2$ (98 mg, 0.44 mmol, 0.10 equiv) and Cs$_2$CO$_3$ (3.56 g, 10.91 mmol, 2.50 equiv) in toluene (20.00 mL) was stirred for h at 80° C. under nitrogen atmosphere. The reaction was cooled to room temperature. The resulting mixture was filtered, the filter cake was washed with EtOAc (100 mL). The filtrate was concentrated under reduced pressure. The residue was purified by reversed combi-flash with the following conditions (70% MeOH in water with 0.1% NH$_3$H$_2$O) to afford tert-butyl 4-[2-methyl-6-(methylcarbamoyl)pyridin-3-yl]piperazine-1-carboxylate (1.17 g, 79.9%) as a white solid. LC-MS: (ES+H, m/z): [M+H]$^+$=335.3. $^1$H NMR (300 MHz, CD$_4$OD) δ 7.89 (d, J=8.2 Hz, 1H), 7.51 (d, J=8.3 Hz, 1H), 3.63 (t, J=5.0 Hz, 4H), 2.97 (d, J=4.4 Hz, 7H), 2.59 (s, 3H), 1.51 (s, 9H).

Step 2: Preparation of N,6-dimethyl-5-(piperazin-1-yl)picolinamide hydrochloride To a stirred solution of tert-butyl 4-[2-methyl-6-(methylcarbamoyl)pyridin-3-yl]piperazine-1-carboxylate (200 mg, 0.60 mmol, 1 equiv) in DCM (4 mL) were added HCl (gas) in 1,4-dioxane (4 mL, 16.00 mmol, 26.75 equiv, 4 M) at room temperature. The resulting solution was stirred at rt for 1 h. LCMS was ok. The resulting mixture was concentrated under reduced pressure to afford N,6-dimethyl-5-(piperazin-1-yl)picolinamide hydrochloride (160 mg, crude) as a white solid which was used directly in next step without further purification. LC-MS: (ES+H, m/z): [M+H]$^+$=235.2

Step 3: Preparation of methyl 3-(furan-3-amido)-4-iodobenzoate

A mixture of methyl 3-amino-4-iodobenzoate (10.00 g, 36.09 mmol, 1.00 equiv), 3-furoic acid (8.09 g, 72.18 mmol, 2.00 equiv), T3P (114.84 g, 180.46 mmol, 5.00 equiv, 50% wt in EA) and DIEA (23.32 g, 180.46 mmol, 5.00 equiv) in DCM (100 mL) was stirred overnight at 60° C. under nitrogen atmosphere. The mixture was allowed to cool down to room temperature. The resulting mixture was diluted with water (150 mL), and was extracted with EtOAc (3×150 mL). The combined organic layers were washed with brine (2×200 mL), dried over anhydrous Na$_2$SO$_4$. After filtration, the filtrate was concentrated under reduced pressure. The residue was purified by silica gel column chromatography, eluted with PE/EA (PE to 5:1) to afford methyl 3-(furan-3-amido)-4-iodobenzoate (6.80 g, 50.76%) as a white solid. LC-MS: (ES+H, in z): [M+H]$^+$=3720.

Step 4: Preparation of methyl 3-[N-(tert-butoxycarbonyl)furan-3-amido]-4-iodobenzoate A solution of methyl 3-(furan-3-amido)-4-iodobenzoate (6.00 g, 16.167 mmol, 1.00 equiv), (Boc)$_2$O (7.06 g, 32.34 mmol, 2.00 equiv) and DMAP (1.98 g, 16.17 mmol, 1.00 equiv) in DCE (100 mL) was stirred overnight at room temperature under nitrogen atmosphere. The resulting mixture was diluted with EtOAc (250 mL), and was washed with water (2×200 mL). The combined organic layers were washed with brine (2×200 mL), dried over anhydrous Na$_2$SO$_4$. After filtration, the filtrate was concentrated under reduced pressure. The residue was purified by silica gel column chromatography, eluted with PE/EtOAc (PE to 3:1) to afford methyl 3-[N-(tert-butoxycarbonyl)furan-3-amido]-4-iodobenzoate (5.00 g, 65.63%) as a white solid. $^1$H NMR (300 MHz, DMSO-d$_6$) δ 8.31 (dd, 1H), 8.13 (d, 1H), 7.90 (d, 11H), 7.79 (t, 1H), 7.69 (dd, 111), 6.79 (dd, 1H), 3.87 (s, 3H), 1.34 (s, 9H).

Step 5: Preparation of methyl 4-oxo-5H-furo[3,2-c]quinoline-7-carboxylate

To a mixture of methyl 3-[N-(tert-butoxycarbonyl)furan-3-amido]-4-iodobenzoate (400 mg, 0.85 mmol, 1.00 equiv) and PCy$_3$ (48 mg, 0.17 mmol, 0.20 equiv) in DMF (12 mL) were added Pd(OAc)$_2$ (38 mg, 0.17 mmol, 0.20 equiv) and K$_2$CO$_3$ (235 mg, 1.70 mmol, 2.00 equiv) at room temperature under nitrogen atmosphere. The final reaction mixture was irradiated with microwave radiation for 2 h at 100° C. The mixture was allowed to cool down to room temperature. The resulting mixture was diluted with EtOAc (50 mL). The resulting mixture was washed with water (2×25 mL). The combined organic layers were washed with brine (2×25 mL), dried over anhydrous Na$_2$SO$_4$. After filtration, the filtrate was concentrated under reduced pressure. The residue was purified by silica gel column chromatography, eluted with PE/EtOAc (100:1 to 1:2) to afford methyl 4-oxo-5H-furo[3,2-c]quinoline-7-carboxylate (120 mg, 58.13%) as a yellow solid. LC-MS: (ES+H, m/z): [M+H]$^+$=244.0.

Step 6: Preparation of methyl 4-oxo-2H,3H,5H-furo [3,2-c]quinoline-7-carboxylate To a solution of methyl 4-oxo-5H-furo[3,2-c]quinoline-7-carboxylate (480 mg, 1.97 mmol, 1.00 equiv) in MeOH/DCM (80 mL/20 mL) was added Pd/C (200 mg, 10% wt) under nitrogen atmosphere. The mixture was hydrogenated at room temperature for 2 days under hydrogen atmosphere. The reaction mixture was filtered through a Celite pad and the filtrate was concentrated under reduced pressure. The residue was purified by reversed combi-flash chromatography with the following conditions: column, C18; mobile phase, MeCN in water, 20% to 50% gradient in 10 min; detector, UV 220 nm to afford methyl 4-oxo-2H,3H,5H-furo [3,2-c]quinoline-7-carboxylate (170 mg, 35%) as a white solid. LC-MS: (ES+H, m/z): [M+H]$^+$=246.2.

Step 7: Preparation of 7-(hydroxymethyl)-2H,3H, 5H-furo[3,2-c]quinolin-4-one

To a stirred solution of methyl 4-oxo-2H,3H,5H-furo[3, 2-c]quinoline-7-carboxylate (170 mg, 0.69 mmol, 1.00 equiv) in THF (8 mL) was added LiAlH$_4$ (0.55 mL, 1.39 mmol, 2.00 equiv, 2.5 M in THF) dropwise at 0° C. under nitrogen atmosphere. The resulting mixture was stirred for 2 h at 0° C. under nitrogen atmosphere. The reaction was quenched by the addition of 1 M aq HCl (10 mL) at 0° C. The resulting mixture was concentrated under reduced pressure. The residue was purified by silica gel column chromatography, eluted with CH$_2$Cl$_2$/MeOH (10:1 to 2:1) to afford 7-(hydroxymethyl)-2H,3H,5H-furo[3,2-c]quinolin-4-one (150 mg, 100%) as a white solid. LC-MS: (ES+H, m/z): [M+H]$^+$=218.0. $^1$H NMR (400 MHz, DMSO-d$_6$) δ 11.38 (s, 1H), 7.53 (d, 1H), 7.34 (s, 1H), 7.09 (dd, 1H), 5.40-5.36 (m, 1H), 4.79 (t, 2H), 4.56 (s, 2H), 3.03 (t, 2H).

Step 8: Preparation of 7-(chloromethyl)-2H,3H,5H-furo[3,2-c]quinolin-4-one

To a stirred solution of 7-(hydroxymethyl)-2H,3H,5H-furo[3,2-c]quinolin-4-one (170 mg, 0.78 mmol, 1.00 equiv) and DMF (29 mg, 0.39 mmol, 0.50 equiv) in DCM (6 mL) was added thionyl chloride (744 mg, 6.26 mmol, 8.00 equiv) dropwise at 0° C. under nitrogen atmosphere. The resulting mixture was stirred overnight at room temperature under nitrogen atmosphere. The resulting mixture was concentrated under vacuum. The residue was purified by silica gel column chromatography, eluted with CH$_2$Cl$_2$/MeOH (30:1 to 10:1) to afford 7-(chloromethyl)-2H,3H,5H-furo[3,2-c] quinolin-4-one (160 mg, 87%) as a white solid. LC-MS: (ES+H, m/z): [M+H]$^+$=236.0.

Step 9: Preparation of N,6-dimethyl-5-[4-({4-oxo-2H,3H,5H-furo[3,2-c]quinolin-7-yl}methyl)piperazin-1-yl]pyridine-2-carboxamide A mixture of 7-(chloromethyl)-2H,3H,5H-furo[3,2-c]quinolin-4-one (200 mg, 0.849 mmol, 1.00 equiv), N,6-dim-ethyl-5-(piperazin-1-yl)pyridine-2-carboxamide hydrochloride (299 mg, assumed 100% yield, 1.10 mmol, 1.30 equiv), DIEA (438.74 mg, 3.396 mmol, 4 equiv) and KI (14.09 mg, 0.085 mmol, 0.10 equiv) in MeCN (5 mL) was stirred for 2 h at 80° C. under nitrogen atmosphere. The resulting mixture was diluted with water (15 mL) and extracted with CH$_2$Cl$_2$: MeOH=10:1 (3×20 mL). The combined organic layers were washed with CH$_2$Cl$_2$ (3×5 mL), dried over anhydrous Na$_2$SO$_4$ and filtered. The filtrate was concentrated under reduced pressure. The residue was purified by silica gel column chromatography, eluted with CH$_2$Cl$_2$/MeOH (0 to 10% gradient in 30 min) to afford N,6-dimethyl-5-[4-({4-oxo-2H,3H,5H-furo[3,2-c]quinolin-7-yl}methyl)piperazin-1-yl]pyridine-2-carboxamide (100 mg) as yellow solid. The residue was purified by trituration with MeCN (5 mL). The precipitated solids were collected by filtration and washed with MeCN (1×1 mL) to afford N,6-dimethyl-5-[4-({4-oxo-2H,3H,5H-furo[3,2-c]quinolin-7-yl}methyl)piperazin-1-yl] pyridine-2-carboxamide (72 mg, 19.3%) as a white solid. LC-MS: (ES+H, m/z): [M+H]$^+$=434.15. $^1$H NMR (400 MHz, DMSO-d$_6$) δ 11.34 (s, 1H), 8.41 (q, J=4.8 Hz, 1H), 7.79 (d, J=8.2 Hz, 1H), 7.56 (d, J=8.1 Hz, 1H), 7.48 (d, J=8.3 Hz, 1H), 7.35 (d, J=1.5 Hz, 1H), 7.17 (dd, J=8.2, 1.5 Hz, 1H), 4.79 (t, J=9.2 Hz, 2H), 3.62 (s, 2H), 3.04 (t, J=9.2 Hz, 2H), 2.95 (t, J=4.7 Hz, 4H), 2.80 (d, J=4.8 Hz, 3H), 2.58 (s, 4H), 2.49 (s, 3H).

Comparative Example 2 (Example 18 in WO2023025307

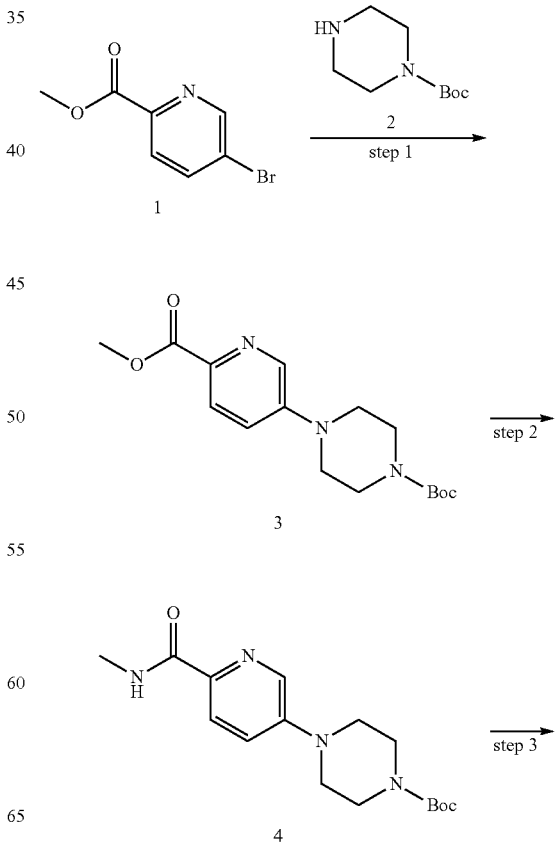

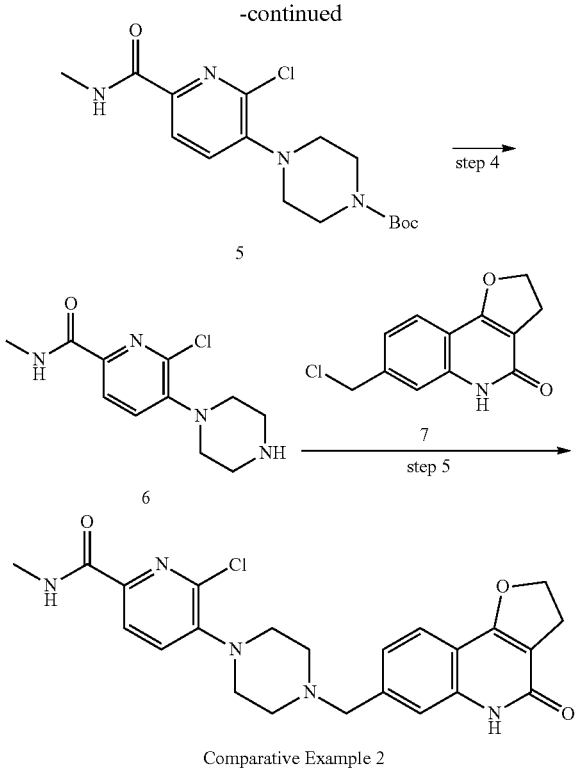

Comparative Example 2

Step 1: Preparation of tert-butyl 4-[6-(methoxycarbonyl)pyridin-3-yl]piperazine-1-carboxylate To a stirred mixture of methyl 5-bromopyridine-2-carboxylate (10.00 g, 46.28 mmol, 1.00 equiv) and tert-butyl piperazine-1-carboxylate (12.93 g, 69.43 mmol, 1.50 equiv) in 1,4-dioxane (100 mL) were added $Cs_2CO_3$ (30.16 g, 92.57 mmol, 2.00 equiv) and RuPhos Palladacycle Gen.3 (1.94 g, 2.31 mmol, 0.05 equiv) at room temperature under nitrogen atmosphere. The resulting mixture was stirred for 5 h at 100° C. under nitrogen atmosphere. The mixture was allowed to cool down to room temperature. The resulting mixture was filtered and the filter cake was washed with EA (300 mL). The filtrate was concentrated under reduced pressure. The residue was purified by silica gel column chromatography, eluted with PE/EA (20~50% in 25 min), the pure fraction was concentrated under vacuum to afford tert-butyl 4-[6-(methoxycarbonyl)pyridin-3-yl]piperazine-1-carboxylate (11 g, Y=67.2%) as a white solid. LC-MS: (ES+H, m/z): $[M+H]^+$=322.2.

Step 2: Preparation of tert-butyl 4-[6-(methylcarbamoyl)pyridin-3-yl]piperazine-1-carboxylate A solution of tert-butyl 4-[6-(methoxycarbonyl)pyridin-3-yl]piperazine-1-carboxylate (5.00 g, 15.55 mmol, 1.00 equiv) in MeOH (50 mL) was treated with $CH_3NH_2$ (15 mL, 25~30% in water) for 10 min at room temperature under nitrogen atmosphere. The resulting mixture was stirred overnight at room temperature under nitrogen atmosphere. The resulting mixture was concentrated under vacuum to afford tert-butyl 4-[6-(methylcarbamoyl)pyridin-3-yl]piperazine-1-carboxylate (5 g, Y=96.8%) as a yellow solid. The resulting mixture was used in the next step directly without further purification. LC-MS: (ES+H, m/z): $[M+H]^+$=321.3.

Step 3: Preparation of tert-butyl 4-[2-chloro-6-(methylcarbamoyl)pyridin-3-yl]piperazine-1-carboxylate A solution of tert-butyl 4-[6-(methylcarbamoyl)pyridin-3-yl]piperazine-1-carboxylate (5 g, 15.60 mmol, 1.00 equiv) in MeCN (30 mL) was treated with NCS (2.71 g, 20.28 mmol, 1.30 equiv) in MeCN (20 mL) for 10 min at room temperature under nitrogen atmosphere. The resulting mixture was stirred overnight at room temperature under nitrogen atmosphere. The resulting mixture was concentrated under reduced pressure. The residue was purified by silica gel column chromatography, eluted with PE/EA (20~50% in 25 min), the pure fraction was concentrated under vacuum to afford tert-butyl 4-[2-chloro-6-(methylcarbamoyl)pyridin-3-yl]piperazine-1-carboxylate (3.5 g, Y=63.2%) as a yellow solid. LC-MS: (ES+H, m/z): $[M+H]^+$=355.1. $^1H$ NMR (400 MHz, DMSO-$d_6$) δ 8.45 (q, J=4.7 Hz, 1H), 7.95 (d, J=8.1 Hz, 1H), 7.68 (d, J=8.2 Hz, 1H), 3.60-3.44 (m, 4H), 3.13-3.01 (m, 4H), 2.79 (d, J=4.8 Hz, 3H), 1.43 (s, 9H).

Step 4: Preparation of 6-chloro-N-methyl-5-(piperazin-1-yl)pyridine-2-carboxamide Hydrochloride A solution of tert-butyl 4-[2-chloro-6-(methylcarbamoyl)pyridin-3-yl]piperazine-1-carboxylate (300 mg, 0.84 mmol, 1.00 equiv) in DCM (3 mL) was treated with HCl in 1,4-dioxane (2 mL) for 1 min at room temperature under nitrogen atmosphere. The resulting mixture was stirred overnight at room temperature under nitrogen atmosphere. The resulting mixture was concentrated under vacuum to afford 6-chloro-N-methyl-5-(piperazin-1-yl)pyridine-2-carboxamide hydrochloride (251 mg, crude) as a yellow solid. The resulting mixture was used in the next step directly without further purification. LC-MS: (ES+H, m/z): $[M+H]^+$= 255.1.

Step 5: Preparation of 6-chloro-N-methyl-5-[4-({4-oxo-2H,3H,5H-furo[3,2-c]quinolin-7-yl}methyl)piperazin-1-yl]pyridine-2-carboxamide To a stirred mixture of 6-chloro-N-methyl-5-(piperazin-1-yl)pyridine-2-carboxamide hydrochloride (203 mg, 0.70 mmol, 1.50 equiv) and 7-(chloromethyl)-2H,3H,5H-furo[3,2-c]quinolin-4-one (110 mg, 0.46 mmol, 1.00 equiv) in MeCN (5 mL) was added KI (15 mg, 0.09 mmol, 0.20 equiv) and DIEA (301 mg, 2.33 mmol, 5.00 equiv) at room temperature under nitrogen atmosphere. The resulting mixture was stirred for 2 h at 80° C. under nitrogen atmosphere. The mixture was allowed to cool down to room temperature. The resulting mixture was filtered, the filter cake was washed with $CH_2Cl_2$/MeOH (10:1, 10 mL). The filtrate was concentrated under reduced pressure. The crude product was purified by Prep-HPLC with the following conditions (Column: XBridge Prep OBD C18 Column, 30*150 mm, 10 m; Mobile Phase A: Water (10 mmol/L $NH_4HCO_3$+0.05% $NH_3H_2O$), Mobile Phase B: MeOH; Flow rate: 60 mL/min; Gradient: 53% B to 68% B in 8 min; Wave Length: 254 nm/220 nm; RT1 (min): 9.27). The pure fraction was concentrated under vacuum and lyophilized to afford 6-chloro-N-methyl-5-[4-({4-oxo-2H,3H,5H-furo[3,2-c]quinolin-7-yl}methyl)piperazin-1-yl]pyridine-2-carboxamide (77.8 mg, Y=36.4%) as white solid. LC-MS: (ES+H, m/z): $[M+H]^+$=454.20. $^1H$ NMR (400 MHz, DMSO-$d_6$) δ 11.36 (s, 1H), 8.43 (q, J=4.7 Hz, 1H), 7.94 (d, J=8.1 Hz, 1H), 7.70-7.63 (m, 1H), 7.56 (d, J=8.0 Hz, 1H), 7.34 (d, J=1.4 Hz, 1H), 7.16 (d, J=8.1, 1.7 Hz, 1H), 4.79 (t, J=9.2 Hz, 2H), 3.61 (s, 2H), 3.16-2.99 (m, 6H), 2.79 (d, J=4.7 Hz, 3H), 2.58 (s, 4H).

Comparative Example 3 (Example 64 in WO2023025307)

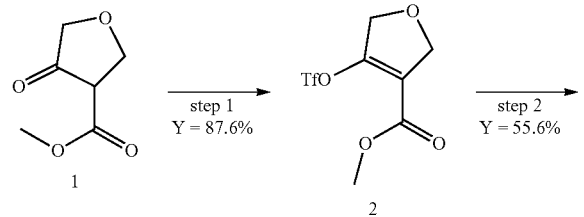

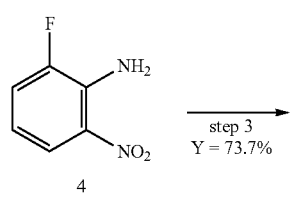

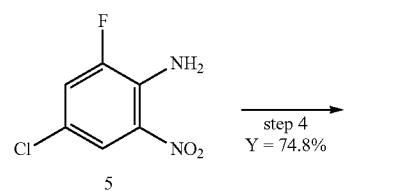

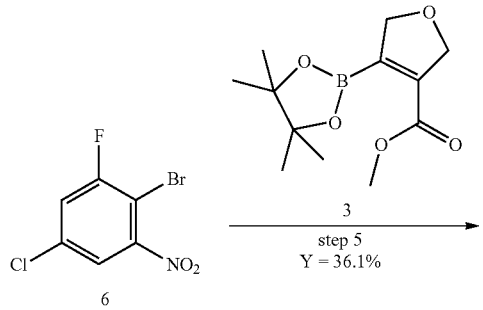

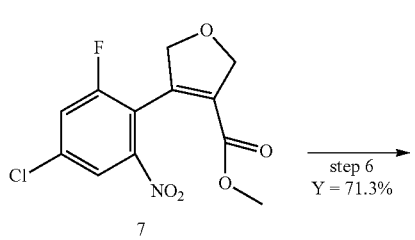

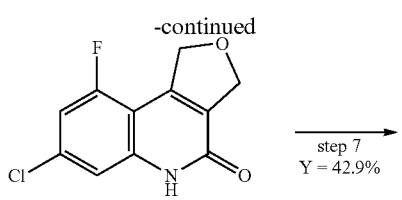

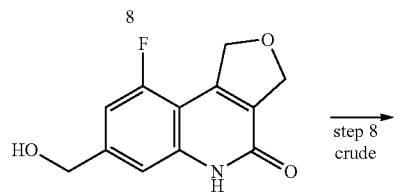

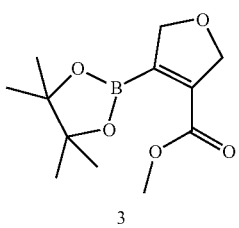

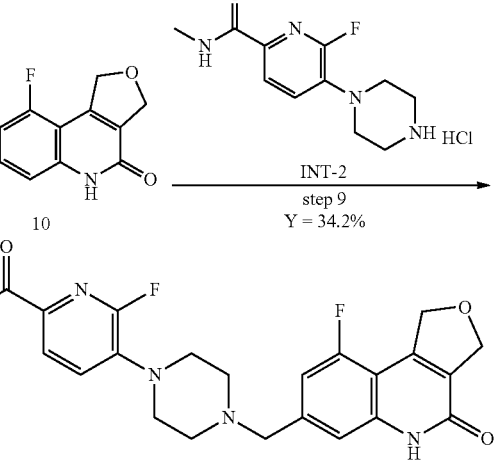

Comparative Example 3

Step 1: Preparation of methyl 4-(((trifluoromethyl)sulfonyl)oxy)-2,5-dihydrofuran-3-carboxylate To a stirred mixture of methyl 4-oxotetrahydrofuran-3-carboxylate (5.00 g, 34.69 mmol, 1.00 equiv) in $CH_2Cl_2$ (50 mL) was added DIEA (7 mL, 41.63 mmol, 1.20 equiv) dropwise at −78° C. under nitrogen atmosphere. The resulting mixture was stirred for 10 min at −78° C. under nitrogen atmosphere. To the above mixture was added $Tf_2O$ (7 mL, 41.63 mmol, 1.20 equiv) dropwise at −78° C. The resulting mixture was stirred for 2 h at room temperature under nitrogen atmosphere. The resulting mixture was concentrated under reduced pressure. The residue was purified by silica gel column chromatography, eluted with PE/EtOAc (0 to 20% gradient in 30 min) to afford methyl 4-(((trifluoromethyl)sulfonyl)oxy)-2,5-dihydrofuran-3-carboxylate (8.40 g, 87.6%) as a red liquid. 1H NMR (400 MHz, $CDCl_3$) δ 4.91 (dd, J=5.8, 4.5 Hz, 2H), 4.79 (dd, J=5.9, 4.5 Hz, 2H), 3.83 (s, 3H). $^{19}F$ NMR (377 MHz, $CDCl_3$) δ −73.79.

Step 2: Preparation of methyl 4-(4,4,5,5-tetramethyl-1,3,2-dioxaborolan-2-yl)-2,5-dihydrofuran-3-carboxylate To a stirred mixture of methyl 4-(((trifluoromethyl)sulfonyl)oxy)-2,5-dihydrofuran-3-carboxylate (8.20 g, 29.69 mmol, 1.00 equiv) and bis(pinacolato)diboron (9.05 g, 35.63 mmol, 1.20 equiv) in dioxane (300 mL) were added $Pd(dppf)Cl_2$ (1.09 g, 1.49 mmol, 0.05 equiv) and KOAc (8.74 g, 89.07 mmol, 3.00 equiv) at room temperature under nitrogen atmosphere. The resulting mixture was stirred for 2 h at 100° C. under nitrogen atmosphere. The mixture was allowed to cool down to room temperature. The resulting mixture was filtered, the filter cake was washed with EtOAc (3×100 mL). The filtrate was concentrated under reduced pressure. The residue was purified by gel column chromatography, eluted with PE/EtOAc (10% to 40% gradient in 30 min) to afford methyl 4-(4,4,5,5-tetramethyl-1,3,2-dioxaborolan-2-yl)-2,5-dihydrofuran-3-carboxylate (4.20 g, 55.6%) as a light yellow oil. LC-MS: (ES+H, m/z): [M+H]$^+$= 255.1. $^1$H NMR (300 MHz, CDCl$_3$) δ 4.93 (td, J=5.2, 4.8, 1.0 Hz, 2H), 4.83 (td, J=5.2, 1.0 Hz, 2H), 3.78 (s, 3H), 1.36 (s, 12H).

Step 3: Preparation of
4-chloro-2-fluoro-6-nitroaniline

A mixture of 2-fluoro-6-nitroaniline (2.00 g, 12.81 mmol, 1.00 equiv) and NCS (1.80 g, 13.45 mmol, 1.05 equiv) in DMF (20 mL) was stirred overnight at room temperature under nitrogen atmosphere. The resulting mixture was diluted with EtOAc (300 mL). The organic layer was washed with water (3×100 mL), dried over anhydrous Na$_2$SO$_4$. After filtration, the filtrate was concentrated under reduced pressure. The residue was purified by silica gel column chromatography, eluted with PE/EtOAc (0 to 20% gradient in 30 min) to afford 4-chloro-2-fluoro-6-nitroaniline (1.80 g, 73.7%) as a yellow solid. LC-MS: (ES-H, m/z): [M−H]$^-$= 189.1. $^1$H NMR (400 MHz, DMSO-d$_6$) δ 7.85 (t, J=2.2 Hz, 1H), 7.68 (dd, J=11.0, 2.5 Hz, 1H), 7.45 (s, 2H).

Step 4: Preparation of
2-bromo-5-chloro-1-fluoro-3-nitrobenzene

A mixture of CuBr$_2$ (3.99 g, 17.84 mmol, 2.00 equiv) and tert-butyl nitrite (5.35 mL, 44.61 mmol, 5.00 equiv) in MeCN (15 mL) was stirred for 10 min at 60° C. under nitrogen atmosphere. To the above mixture was added 4-chloro-2-fluoro-6-nitroaniline (1.70 g, 8.92 mmol, 1.00 equiv) in MeCN (10 mL) dropwise at 60° C. The resulting mixture was stirred for an additional 2 h at 60° C. The mixture was allowed to cool down to room temperature. The resulting mixture was diluted with water (100 mL). The resulting mixture was extracted with EtOAc (3×100 mL). The combined organic layers were washed with brine (3×100 mL), dried over anhydrous Na$_2$SO$_4$. After filtration, the filtrate was concentrated under reduced pressure. The residue was purified by silica gel column chromatography, eluted with PE/EtOAc (0 to 5% gradient in 30 min) to afford 2-bromo-5-chloro-1-fluoro-3-nitrobenzene (1.70 g, 74.8%) as a white solid. $^1$H NMR (400 MHz, DMSO-d$_6$) δ 8.19-8.13 (m, 1H), 8.05 (ddt, J=8.5, 2.3, 0.9 Hz, 1H).

Step 5: Preparation of methyl 4-(4-chloro-2-fluoro-6-nitrophenyl)-2,5-dihydrofuran-3-carboxylate To a stirred mixture of 2-bromo-5-chloro-1-fluoro-3-nitrobenzene (700 mg, 2.75 mmol, 1.00 equiv) and methyl 4-(4,4,5,5-tetramethyl-1,3,2-dioxaborolan-2-yl)-2,5-dihydrofuran-3-carboxylate (699 mg, 2.75 mmol, 1.00 equiv) in dioxane (20 mL) and H$_2$O (1 mL) were added Pd(dppf)Cl$_2$·CH$_2$Cl$_2$ (112 mg, 0.14 mmol, 0.05 equiv) and K$_2$CO$_3$ (1141 mg, 8.25 mmol, 3.00 equiv). The resulting mixture was stirred overnight at 80° C. under nitrogen atmosphere. The mixture was allowed to cool down to room temperature. The resulting mixture was diluted with water (200 mL). The resulting mixture was extracted with EtOAc (3×200 mL). The combined organic layers were washed with brine (3×200 mL), dried over anhydrous Na$_2$SO$_4$. After filtration, the filtrate was concentrated under reduced pressure. The residue was purified by silica gel column chromatography, eluted with PE/EtOAc (0 to 20% gradient in 30 min) to afford methyl 4-(4-chloro-2-fluoro-6-nitrophenyl)-2,5-dihydrofuran-3-carboxylate (300 mg, 36.1%) as a yellow solid. $^1$H NMR (400 MHz, DMSO-d$_6$) δ 8.22 (t, J=18 Hz, 1H), 8.13 (dd, J=9.2, 2.0 Hz, 1H), 4.91 (s, 4H), 3.55 (s, 3H).

Step 6: Preparation of 7-chloro-9-fluoro-3,5-dihydrofuro[3,4-c]quinolin-4(1H)-one To a stirred mixture of methyl 4-(4-chloro-2-fluoro-6-nitrophenyl)-2,5-dihydrofuran-3-carboxylate (300 mg, 1.00 mmol, 1.00 equiv) and Fe (245 mg, 4.31 mmol, 10.00 equiv) in EtOH (10 mL) was added CaCl$_2$) (662 mg, 5.97 mmol, 6.00 equiv). The resulting mixture was stirred for 2 h at 90° C. under nitrogen atmosphere. The mixture was allowed to cool down to room temperature. The resulting mixture was diluted with water (100 mL). The resulting mixture was extracted with EtOAc (3×100 mL). The combined organic layers were washed with brine (3×100 mL), dried over anhydrous Na$_2$SO$_4$. After filtration, the filtrate was concentrated under reduced pressure. The residue was purified by trituration with MeCN (3 mL) to afford 7-chloro-9-fluoro-3,5-dihydrofuro[3,4-c]quinolin-4(1H)-one (170 mg, 71.3%) as a white solid. LC-MS: (ES+H, m/z): [M+H]$^+$=240.1. $^1$H NMR (400 MHz, DMSO-d$_6$) δ 12.15 (s, 1H), 7.28 (dd, J=10.4, 1.9 Hz, 1H), 7.24 (dd, J=2.0, 0.9 Hz, 1H), 5.30 (td, J=4.3, 2.2 Hz, 2H), 4.92 (t, J=4.2 Hz, 2H).

Step 7: Preparation of 9-fluoro-7-(hydroxymethyl)-3,5-dihydrofuro[3,4-c]quinolin-4(1H)-one To a stirred mixture of 7-chloro-9-fluoro-3,5-dihydrofuro[3,4-c]quinolin-4(1H)-one (190 mg, 0.79 mmol, 1.00 equiv) and 2nd Generation XPhos Precatalyst (62 mg, 0.08 mmol, 0.10 equiv) in dioxane (6 mL) was added (Tributylstannyl)methanol (509 mg, 1.59 mmol, 2.00 equiv). The resulting mixture was stirred for 2 h at 100° C. under nitrogen atmosphere. The mixture was allowed to cool down to room temperature. The resulting mixture was diluted with water (50 mL). The resulting mixture was extracted with CH$_2$Cl$_2$/MeOH (10:1)(3×50 mL). The combined organic layers were washed with brine (2×50 mL), dried over anhydrous Na$_2$SO$_4$. After filtration, the filtrate was concentrated under reduced pressure. The residue was purified by silica gel column chromatography, eluted with CH$_2$Cl$_2$/MeOH (0 to 10% gradient in 30 min) to afford 9-fluoro-7-(hydroxymethyl)-3,5-dihydrofuro[3,4-c]quinolin-4(1H)-one (80 mg, 42.9%) as a white solid. LC-MS: (ES+H, m/z): [M+H]$^+$= 236.1. $^1$H NMR (400 MHz, DMSO-d$_6$) δ 12.06 (s, 1H), 7.22 (s, 1H), 6.95 (d, J=11.3 Hz, 1H), 5.51 (t, J=5.7 Hz, 1H), 5.32 (tt, J=3.9, 1.8 Hz, 2H), 4.93 (t, J=4.2 Hz, 2H), 4.57 (d, J=5.7 Hz, 2H).

Step 8: Preparation of 7-(chloromethyl)-9-fluoro-3,5-dihydrofuro[3,4-c]quinolin-4(1H)-one To a stirred mixture of 9-fluoro-7-(hydroxymethyl)-3,5-dihydrofuro[3,4-c]quinolin-4(1H)-one (60 mg, 0.26 mmol, 1.00 equiv) and DMF (2 mg, 0.03 mmol, 0.10 equiv) in CH$_2$Cl$_2$ (4 mL) was added SOCl$_2$ (0.06 mL, 0.77 mmol, 3.00 equiv) dropwise at 0° C. under nitrogen atmosphere. The resulting mixture was stirred overnight at room temperature under nitrogen atmosphere. The resulting mixture was concentrated under reduced pressure to afford 7-(chloromethyl)-9-fluoro-3,5-dihydrofuro[3,4-c]quinolin-4(1H)-one (50 mg, crude) as a yellow solid. LC-MS: (ES+H, m/z): [M+H]$^+$=253.9.

Step 9: Preparation of 6-fluoro-5-(4-((9-fluoro-4-oxo-1,3,4,5-tetrahydrofuro[3,4-c]quinolin-7-yl)methyl)piperazin-1-yl)-N-methylpicolinamide To a stirred mixture of 7-(chloromethyl)-9-fluoro-3,5-dihydrofuro[3,4-c]quinolin-4(1H)-one (45 mg, 0.18 mmol, 1.00 equiv) and 6-fluoro-N-methyl-5-(piperazin-1-yl)picolinamide hydrochloride (73 mg, 0.27 mmol, 1.50 equiv) in MeCN (3 mL) were added KI (6 mg, 0.04 mmol, 0.20 equiv) and DIEA (115 mg, 0.89 mmol, 5.00 equiv). The resulting mixture was stirred for 2 h at 80° C. under nitrogen atmosphere. The mixture was allowed to cool down to room temperature. The resulting mixture was concentrated under reduced pressure. The residue was purified by silica gel column chromatography, eluted with $CH_2Cl_2$/MeOH (0 to 10% gradient in 30 min) to afford crude product (70 mg). The crude product (70 mg) was purified by Prep-HPLC with the following conditions (Column: Xselect CSH C18 OBD Column 30*150 mm, 5 μm; Mobile Phase A: Water (0.1% HCOOH), Mobile Phase B: MeCN; Flow rate: 60 mL/min mL/min; Gradient: 4% B to 15% B in 8 min; Wave Length: 254 nm/220 nm nm; RT1 (min): 12.82). The pure fraction was concentrated under reduced pressure and lyophilized to afford 6-fluoro-5-(4-((9-fluoro-4-oxo-1,3,4,5-tetrahydrofuro[3,4-c]quinolin-7-yl)methyl)piperazin-1-yl)-N-methylpicolinamide (28.0 mg, 34.2%) as a white solid. LC-MS: (ES+H, m/z): [M+H]$^+$=456.10. $^1$H NMR (300 MHz, DMSO-$d_6$) δ 12.03 (s, 1H), 8.41 (q, J=4.7 Hz, 1H), 7.85 (dd, J=8.0, 1.5 Hz, 1H), 7.57 (dd, J=10.6, 8.1 Hz, 1H), 7.22 (s, 1H), 7.03 (d, J=11.2 Hz, 1H), 5.32 (d, J=5.1 Hz, 2H), 4.93 (t, J=4.2 Hz, 2H), 3.62 (s, 2H), 3.26-3.11 (m, 4H), 2.77 (d, J=4.7 Hz, 3H), 2.57 (t, J=4.6 Hz, 4H). $^{19}$F NMR (282 MHz, DMSO-$d_6$) δ−72.508, −118.241.

Comparative Example 4 (Example 4 in CN115232129A)

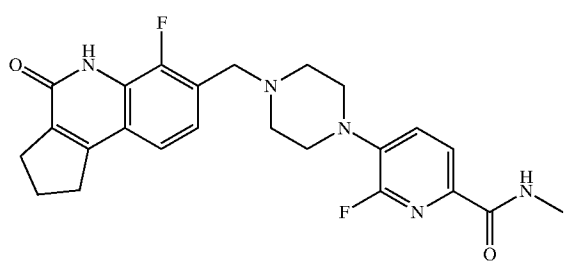 [SMILES: CNC(=O)c1ccc(N2CCN(Cc3ccc4c5c(c(=O)[nH]c4c3F)CCC5)CC2)c(F)n1]

Example A: Cell Growth Inhibition Assay

The objective of this study is to evaluate the effect of compound disclosed herein on cell proliferation through the cell viability assay in DLD-1 BRCA2(−/−) and parental isogenic pair and MDA-MB-436 (mutated BRCA1) cell lines. The CellTiter-Glo (CTG) based cell viability assay is designed to determine the number of viable cells in the culture because of compound effect, by quantifying ATP, which indicates the presence of metabolically active cells.

DLD-1 BRCA2(−/−) and parental isogenic pair were cultured in RPMI 1640 supplemented with 10% fetal bovine serum (FBS), and MDA-MB-436 cells were cultured in DMEM supplemented with 10% FBS. Both are culture at 37° C. with 5% $CO_2$. Invention compounds were distributed to the 384 well plate (Corning, 3764) using Echo acoustic liquid handler to form a 1:3 serially diluted final concentration with top dose of 10 or 30 μM. The cells were seeded into the plate in the density of 50 cells/well (DLD-1 parental), 200 cells/well (DLD-1 BRCA2−/−), or 500 cells/well (MDA-MB-436). After a short spun, the cells were cultured in a well moisturized incubator at 37° C. with 5% $CO_2$ for 7 days without disturbance. The cell viability was measured by CellTiter Glo 2.0 assay kit (Promega, G9243), and growth inhibition rate was calculated and plotted against final compound concentration, and the data were fitted in Xfit to generate IC$_{50}$.

Example B: Biochemical (FP) Assay

Assays based on fluorescent polarization (FP) have been widely utilized in drug discovery due to the homogenous format, robust performance and lack of interference seen in other assays. To characterize our compounds, we utilized an assay measuring the displacement of a commercially available fluorescently labeled PARP 1/2 inhibitor (PARPi-FL, Tocris Biosciences, #6461) as exemplified in assays performed in WO2014/064149 and WO2021/013735A1. The assay was performed utilizing the following method:

Compounds were dissolved in DMSO an Echo550 liquid handler was utilized to make serial dilations in the desired concentration range in Optiplate-384F plates. 100% DMSO was used for the high (with protein) and low (without protein) control samples. 20 nL of compound or DMSO alone was added to individual assay plate wells.

PARP1 and PARP2 protein were expressed, purified, and diluted in assay buffer containing 50 mM Tris pH 8.0, 0.001% Triton X-100, 10 mM $MgCl_2$, 150 mM NaCl to a final concentration of 20 nM. The PARPi-FL was then added at a final concentration of 3 nM.

The assay plate is centrifuged at 1000 rpm for 1 min and incubated for 4 h at room temperature.

The fluorescent polarization is read using an Envision plate reader using the following settings:
Excitation filter—FITC FP 480-Ex Slot 3
Emission filter—FITC FP P-pol 535-Em Slot4
2nd Emission filter—FITC FP S-pol 535-Em Slot 3
Mirror module—FITC FP Dual Enh-Slot 1

The inhibition rate is calculated using the percentage of permuted Mahalanobis distances greater than the control samples (mP value) following the equation below:

mP$_c$: the mP value of compounds
mP$_L$: the mP value of Low controls
mP$_H$: the mP value of High controls $$\text{Inhibition (\%)} = \left(1 - \frac{mP_C - mP_L}{mP_H - mP_L}\right) \times 100\%$$

XLFit (equation 201) is used to calculate a reported IC$_{50}$ for each compound.

The data from examples A and B are provided in Table 2.

TABLE 2

| Ex. | $EC_{50}$ DLD-1 BRCA2(-/-) μM | $EC_{50}$ DLD-1 parental μM | $EC_{50}$ MDA-MB-436 μM | $IC_{50}$ FP PARP1 μM | $IC_{50}$ FP PARP2 μM |
|---|---|---|---|---|---|
| 1 | 0.0041 | >30 | 0.0029 | 0.0081 | >100 |
| 2 | 0.1 | | 0.068 | 0.1 | >100 |
| 3 | 0.0091 | | 0.0043 | 0.022 | >100 |
| 4 | 0.0021 | | 0.0012 | 0.016 | >100 |
| 5 | 0.0042 | | 0.0029 | 0.041 | >100 |
| 6 | 0.0038 | | 0.0021 | 0.021 | >100 |
| 7 | 0.0021 | | 0.0013 | 0.018 | >100 |
| 8 | 0.0018 | | 0.00094 | 0.019 | >100 |
| 9 | 0.0032 | >30 | 0.0016 | 0.0058 | >100 |
| 10 | 0.00064 | | 0.0003 | 0.010 | >100 |
| 11 | 0.0011 | | 0.00086 | 0.014 | >100 |
| 12 | 0.0016 | | 0.0009 | 0.0094 | >100 |
| 13 | 0.0014 | | 0.0012 | 0.025 | >100 |
| 14 | 0.0012 | | 0.00068 | 0.010 | >100 |
| 15 | 0.0019 | | 0.00075 | 0.012 | >100 |
| 16 | 0.0051 | | 0.0031 | 0.027 | >100 |
| 17 | 0.0015 | | 0.0013 | 0.014 | >100 |
| 18 | 0.0019 | >30 | 0.0012 | 0.0062 | >100 |
| 19 | 0.057 | | 0.031 | 0.100 | >100 |
| 20 | 0.0062 | | 0.004 | 0.011 | >100 |
| 21 | 0.0013 | | 0.00066 | 0.0087 | >100 |
| 22 | 0.0066 | >30 | 0.0049 | 0.013 | >100 |
| 23 | 0.0047 | | 0.0027 | 0.026 | >100 |
| 24 | 0.0038 | | 0.003 | 0.0076 | >100 |
| 25 | 0.0018 | | 0.0014 | 0.009 | >100 |
| 26 | 0.0075 | | 0.006 | 0.013 | >100 |
| 27 | 0.021 | | 0.014 | 0.052 | >100 |
| 28 | 0.00084 | | 0.00057 | 0.010 | >100 |
| 29 | 0.0043 | | 0.0021 | 0.017 | >100 |
| 30 | 0.0065 | | 0.0046 | 0.056 | >100 |
| 31 | 0.0077 | | 0.0069 | 0.055 | >100 |
| 32 | 0.0054 | | 0.0092 | 0.064 | >100 |
| 33 | 0.00096 | | 0.00079 | 0.011 | >100 |
| 34 | 0.00099 | | 0.0011 | 0.040 | >100 |
| Comp. Ex. 1 | 0.002 | | 0.0006 | 0.0037 | >100 |
| Comp. Ex. 2 | 0.0017 | | 0.0007 | 0.004 | >100 |
| Comp. Ex. 3 | 0.0016 | | 0.0004 | 0.0043 | >100 |
| Comp. Ex. 4 | 0.001 | | 0.0011 | 0.0088 | >100 |

Example C: In Vitro Human Transporter Efflux

Example C1: MDR1 and BCRP

Madin-Darby canine kidney (MDCKII) cells expressing either MDR1 or BCRP were seeded onto Corning HIS Transwell® 96-well polycarbonate permeable (0.4 m pore) supports at a density of 545,000 cells/cm². Cells were incubated for 4-8 days prior to assay, and monolayer integrity was assessed by measuring transepithelial electrical resistance (TEER). Test and reference compounds were diluted with the transport buffer (HBSS HEPES pH7.4) to concentrations of 10 and 1 μM, respectively. The final organic solvent concentration was 0.5% (v/v). Bidirectional (apical-to-basolateral and basolateral-to-apical) flux of the test and reference compounds was determined over a 2-hour incubation at 37° C. and 5% $CO_2$ with a relative humidity of 95%. At the end of the incubation, samples from the apical and basolateral side were taken and then precipitated with acetonitrile containing internal standard. After centrifugation at 3200×g, supernatants were diluted 1:1 (v/v) with water and subjected to analysis via HPLC-MS/MS. The integrity of the cell monolayers during the assay was confirmed by using the marker Lucifer yellow at a final concentration of 100 μM.

Example C2: Caco-2

Following a 1-hr. equilibration period in cell culture medium maintained at 37° C. in an incubator containing a 5% $CO_2$ atmosphere at 95% relative humidity, Corning 96-well HTS Transwell® permeable support plates were seeded with 34,300 Caco-2 cells (ATCC) per well. Following seeding, plates were cultured for 14-18 days with cell culture medium replacement every other day beginning no later than 24 hr. after plating. Monolayer barrier integrity was monitored during the culture period using transepithelial electrical resistance (TEER) measurements taken with a Millicell Epithelial Volt-Ohm system. Caco-2 monolayers were considered ready for use when the TEER value >230 ohm·cm². Working stocks of individual test articles were prepared at a concentration of 5 μM by diluting 1 mM stocks prepared in DMSO into 10 mM HEPES. Prior to conducting the assay, Caco-2 plates were washed twice with prewarmed 10 mM HEPES and then equilibrated in 10 mM HEPES for 30 min. at 37° C. Following equilibration, test article flux was tested bidirectionally (in both the apical-to-basolateral and basolateral-to-apical directions) by adding test article working stocks to either the apical or basolateral chambers. Blank 10 mM HEPES was added to the opposite sides. Plates were then incubated at 37° C. for 2 hours. At the end of the incubation, aliquots from both sides of each monolayer were quenched with 4 volumes of ACN containing internal standards. Following a centrifugation step, supernatants were diluted with pure water prior to analysis via LC-MS/MS.

Apparent permeability ($P_{app}$, ×10$^{-6}$ cm/s) was calculated for all transport assays using the following equation:

$$P_{app} = \frac{dQ/dt}{A \times D_0}$$

Where: $P_{app}$ is apparent permeability (×10$^{-6}$ cm/s).
dQ/dt is the rate of drug transport (pmol/s).
A is the surface area of the membrane (cm$^2$).
$D_0$ is the initial donor concentration (nM; pmol/cm$^3$).

Efflux ratio was determined by calculating the ratio of the $P_{app}$ in the basolateral-to-apical direction to the $P_{app}$ in the apical-to-basolateral direction using the following equation:

$$\text{Efflux Ratio} = \frac{P_{app\,(B-to-A)}}{P_{app\,(A-to-B)}}$$

Where: $P_{app\,(B-to-A)}$ is the apparent permeability in the basolateral-to-apical direction.
$P_{app\,(A-to-B)}$ is the apparent permeability in the apical-to-basolateral direction.

The data from example C1 and C2 is provided in Table 3.

by either addition of blank plasma to buffer samples or the addition of blank buffer to plasma samples. Subsequently, 400 µL (4 volumes) of acetonitrile containing internal were added to all samples to precipitate proteins prior to analysis by UPLC-MS/MS to determine the relative concentrations of test articles. The unbound fractions in plasma were calculated using the concentrations of test articles in buffer and plasma samples according to the following equation:

Percentage unbound (%) =

$$\frac{\text{Analyte to }IS\text{ Peak Area Ratio (buffer chamber)}}{\text{Analyte to }IS\text{ Peak Area Ratio (plasma chamber)}} \times 100$$

Determination of Fraction Unbound in Brain Homogenate (Bu)

The equilibrium dialysis method was used to investigate the in vitro binding of test articles and reference compounds to rodent brain homogenate. Brains collected from naïve animals were weighed and homogenized in 4 volumes of PBS, pH 7.4. Brain homogenate samples containing 1 µM test article or blank dialysis buffer solution (PBS, pH 7.4) were added to separate chambers of the dialysis wells of the High Throughput equilibrium Dialysis (HTD) device. The dialysis plate was sealed and placed in an incubator at 37° C. with 5% $CO_2$ with shaking at approximately 100 rpm for 6 hours. All experiments were performed in duplicate.

TABLE 3

MDR1, BCRP and Caco-2

| Ex. | MDCK-MDR1 Papp AB | MDCK-MDR1 Papp BA | MDCK-MDR1 Ratio | BCRP Papp AB | BCRP Papp BA | BCRP Ratio | Caco-2 AB | Caco-2 BA | Caco-2 Ratio |
|---|---|---|---|---|---|---|---|---|---|
| 1 | 15.9 | 29.6 | 1.87 | 21.7 | 20.4 | 0.95 | | | |
| 4 | 4.4 | 8.6 | 1.96 | | | | | | |
| 5 | 10.3 | 21.2 | 2.06 | | | | | | |
| 9 | 19.4 | 31.4 | 1.6 | 26.7 | 24.3 | 0.91 | 20.5 | 28.1 | 1.4 |
| 18 | 15.2 | 22.7 | 1.5 | 21.1 | 18.2 | 0.87 | | | |
| 22 | 15.1 | 23.3 | 1.55 | 28.2 | 23.6 | 0.85 | | | |
| 24 | 16.3 | 32.9 | 2.07 | 22.9 | 24.4 | 1.07 | | | |
| Comp. Ex. 1 | 7.5 | 39.8 | 5.3 | | | | 2.5 | 26.2 | 10.4 |
| Comp. Ex. 2 | 5.7 | 29 | 5.1 | | | | 2.4 | 21.9 | 9.3 |
| Comp. Ex. 3 | 6.6 | 32.3 | 5 | | | | 0.8 | 5.5 | 7.3 |
| Comp. Ex. 4 | 16.3 | 20.6 | 1.3 | | | | 11.5 | 14.5 | 1.2 |

Example D: In Vivo Determination of Rat Kp,uu

Determination of Fraction Unbound in Plasma (Pu)

The equilibrium dialysis method was used to investigate the in vitro binding of test articles and reference compounds to plasma proteins. Plasma samples containing 5 µM test article or blank dialysis buffer solution (PBS, pH 7.4) were added to separate chambers of the dialysis wells of the High Throughput equilibrium Dialysis (HTD) device. The dialysis plate was sealed and placed in an incubator at 37° C. with 5% $CO_2$ with shaking at approximately 100 rpm for 6 hours. All experiments were performed in duplicate. Ketoconazole (5 µM) was used as the reference compound. After incubation, the seal was removed, and 50 µL, of post-dialysis samples were pipetted from both buffer and plasma chambers into fresh 96-well plates. Samples were equimatrilyzed Telmisartan (5 nM) was used as the reference compound. After incubation, the seal was removed, and 50 µL of post-dialysis samples were pipetted from both buffer and brain homogenate chambers into fresh 96-well plates. Samples were equimatrilyzed by either addition of blank homogenate to buffer samples or the addition of blank buffer to homogenate samples. Subsequently, 400 µL (4 volumes) of acetonitrile containing internal were added to all samples to precipitate proteins prior to analysis by UPLC-MS/MS to determine the relative concentrations of test articles. The unbound fractions in diluted brain homogenate were calculated using the concentrations of test articles in buffer and homogenate samples according to the following equation:

Percentage unbound homogenate (%) =

$$\frac{\text{Analyte to } IS \text{ Peak Area Ratio (buffer chamber)}}{\text{Analyte to } IS \text{ Peak Area Ratio (homogenate chamber)}} \times 100$$

Correction to Percentage Unbound in Undiluted Brain was Achieved with the Following Equation:

Percentage unbound brain (%) =

$$100 \times \frac{1/5}{\left(\frac{1}{\text{Percentage unbound homogenate}/100} - 1\right) + 1/5}$$

Determination of the Drug Brain-to-Plasma Partition Coefficient (Kp) and Drug Unbound Kp (Kp,uu) in Rat Compounds were formulated either individually or in a cassette (as a mixture) at a concentration of 0.1 mg/mL/compound in sterile water containing 0.5% (w/v) methylcellulose 400 cP and administered to male Sprague-Dawley rats via oral gavage at a dose volume of 10 mL/kg. One animal was sacrificed at each of the following time points: 0.5, 1, 2, 4, 8, and 24 hours post-dose, and brain and blood samples were collected. Plasma was prepared from blood via refrigerated centrifugation, and plasma samples were stored frozen at −80° C. until bioanalysis. Brain samples were rinsed with saline to remove residual blood and blotted dry with a paper wipe. Brain samples were then weighed and homogenized with 3 volumes (v/w) of water and stored frozen at −80° C. until bioanalysis.

Prior to bioanalysis, plasma and brain samples were extracted with 4 volumes of acetonitrile containing internal standard and centrifuged for 15 minutes. Supernatants were diluted with 2 volumes of water and injected for analysis via HPLC-MS/MS. Plasma and brain homogenate drug concentrations were determined against calibration curves generated by spiking blank rat plasma or brain homogenate with drug across an appropriate concentration range. The brain homogenate concentration was corrected for the homogenization buffer dilution factor yielding total brain drug concentrations.

The brain-to-plasma partition coefficient (Kp) was determined for each compound, calculated as: AUCbrain:AUCplasma, provided tlast was identical in each matrix. If the drug concentration versus time profile for one matrix fell below the lower limit of quantification at a time point earlier than in the other matrix, then the brain Kp was calculated as the average of the ratios of total brain drug concentration to total plasma drug concentration measured at each time point where drug concentrations in both matrices were quantifiable.

The Kp,uu was then calculated from the Kp using the following equation: Kp,uu=Kp*(fraction unbound in brain homogenate/fraction unbound in plasma).

The data from example D is provided in Table 4.

TABLE 4

Kp, uu Data

| Ex. | Rat Kpuu |
|---|---|
| 1 | 1.0 |
| 9 | 0.65 |
| 24 | 0.81 |

Example E: HLM and hHEP Assays

HLM

Working stocks of individual test articles were prepared at a concentration of 100 µM by diluting 10 mM stocks prepared in DMSO 100-fold (v:v) into ACN. Thawed hepatic microsomes were suspended in 100 mM potassium phosphate buffer, pH 7.4 to a microsomal protein concentration of 0.562 mg/mL. Diluted microsomes were combined with a solution of 10 mM NADPH, and the mixture was pre-warmed to 37° C. for 8 min. Reactions were initiated by addition of the test article working stocks to achieve a final test article concentration of 1 µM. Final microsomal protein and NADPH concentrations were 0.5 mg/mL and 1 mM, respectively. Incubations containing NADPH were run in duplicate. Test article losses mediated by non-CYP mechanisms were evaluated in a parallel set of incubations run in the absence of NADPH. Incubations lacking NADPH consisted of 1 replicate per test article. Following incubation in a 37° C. water bath, aliquots of individual reactions were quenched with cold ACN containing internal standards at 0.5, 15-, 30-, 60-, 90-, and 120-min. Precipitated protein was pelleted via refrigerated centrifugation. Supernatants were diluted into an equal volume of pure water and mixed well prior to analysis via LC-MS/MS. In vitro intrinsic clearances ($CL_{int}$) in µL/min/mg were determined for each incubation from calculated in vitro half-lives determined using a standard log-linear regression approach. In vitro $CL_{int}$ values were scaled up using the following physiological scaling factors: 40 mg microsomal protein/g human liver and 25.7 g human liver/kg body weight. Scaled intrinsic clearance values were finally introduced to the well-stirred liver model for the purpose of calculating predicted human hepatic clearance ($CL_{hep,pred}$) in mL/min/kg assuming a human liver blood flow of 21 mL/min/kg and making no corrections for test article binding to red blood cells, plasma proteins, or components of the incubation system.

hHEP

Working stocks of individual test articles were prepared at concentrations of 100 µM by diluting 10 mM stocks prepared in DMSO 100-fold (v:v) into ACN/$H_2O$ (50/50, v:v). Human cryopreserved hepatocytes were thawed in a 37° C. water bath in <2 min., suspended in thawing media, and then centrifuged at 100×g for 10 min. Thawing media was aspirated, and pelleted hepatocytes were resuspended into incubation media at $1.5 \times 10^6$ cells/mL. Cell viability was determined using an Acridine Orange/Propidium Iodine stain, and hepatocytes were further diluted with incubation media to $0.5 \times 10^6$ viable cells/mL. Hepatocyte aliquots of 198 µL were added to wells of a 96-well plate, and test article incubations were initiated by the addition of 2 µL of 100 µM working stocks. Plates were incubated at 37° C. in a 5% $CO_2$ atmosphere at 95% relative humidity on an orbital shaker at 300 rpm. Incubations were performed in duplicate. Following incubation, aliquots of individual reactions were terminated by addition of ACN containing internal standards at 0, 30-, 60-, 90-, 120-, and 240-min. Precipitated protein was pelleted via refrigerated centrifugation Supernatants were diluted into an equal volume of pure water and mixed well prior to analysis via LC-MS/MS. In vitro intrinsic clearances ($CL_{int}$) in µL/min/$10^6$ cells were determined for each incubation from calculated in vitro half-lives determined using a standard log-linear regression approach. In vitro $CL_{int}$ values were scaled up using the following physiological scaling factors: $99 \times 10^6$ cells/g human liver and 25.7 g human liver/kg body weight. Scaled intrinsic clearance values were finally introduced to the well-stirred liver model for the purpose of calculating predicted human hepatic clearance ($CL_{hep,pred}$) in mL/min/kg assuming a human liver blood flow of 21 mL/min/kg and making no corrections for test article binding to red blood cells, plasma proteins, or components of the incubation system.

The data from example E is provided in Table 5.

TABLE 5

| | HLM and HHEP Data | |
| --- | --- | --- |
| Ex. | HLM Clh (mL/min/kg) | HHEP Clh (mL/min/kg) |
| 9 | <4 | <3.3 |
| Comp. Ex. 1 | <4 | <3.3 |
| Comp. Ex. 2 | 4.2 | 6.6 |
| Comp. Ex. 3 | 7.2 | 7.1 |
| Comp. Ex. 4 | 11.5 | 14.5 |

What is claimed is:

1. A compound:

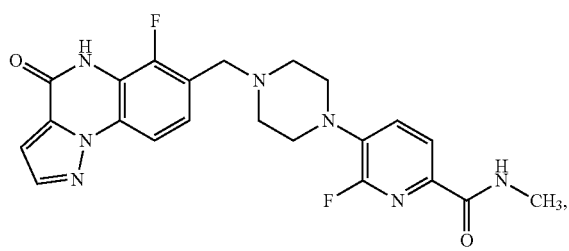 [SMILES: CNC(=O)c1ccc(N2CCN(Cc3ccc4c([nH]c(=O)c5ccnn54)c3F)CC2)c(F)n1]

or a pharmaceutically acceptable salt or tautomer thereof.

2. The compound of claim 1, wherein the compound is:

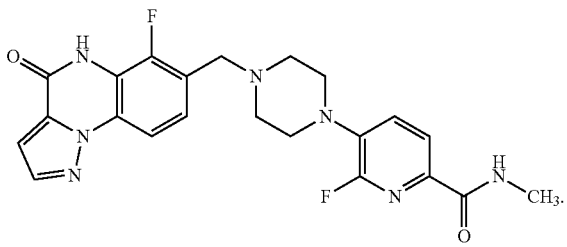 [SMILES: CNC(=O)c1ccc(N2CCN(Cc3ccc4c([nH]c(=O)c5ccnn54)c3F)CC2)c(F)n1]

3. A pharmaceutical composition comprising a pharmaceutically acceptable excipient and the compound of claim 1, or a pharmaceutically acceptable salt or tautomer thereof.

4. A pharmaceutical composition comprising a pharmaceutically acceptable excipient and the compound of claim 2.

* * * * *